(12) United States Patent
Wasson et al.

(10) Patent No.: US 8,762,173 B2
(45) Date of Patent: Jun. 24, 2014

(54) METHOD AND APPARATUS FOR INDIRECT MEDICAL CONSULTATION

(75) Inventors: David S. Wasson, Alexandria, LA (US); Paul A. Guillory, Alexandria, LA (US); John A. Dolak, Elwood, IL (US); Matthew A. Goldman, Carlsbad, CA (US)

(73) Assignee: Red Stick Ventures L.L.C., Alexandria, LA (US)

( * ) Notice: Subject to any disclaimer, the term of this patent is extended or adjusted under 35 U.S.C. 154(b) by 617 days.

(21) Appl. No.: 12/270,357

(22) Filed: Nov. 13, 2008

(65) Prior Publication Data

US 2009/0125326 A1   May 14, 2009

Related U.S. Application Data

(60) Provisional application No. 60/987,658, filed on Nov. 13, 2007.

(51) Int. Cl.
*G06F 17/10* (2006.01)
*G06Q 50/00* (2012.01)
*G06Q 10/00* (2012.01)
*G06Q 40/00* (2012.01)
*G07F 19/00* (2006.01)

(52) U.S. Cl.
USPC .................................. 705/3; 705/2

(58) Field of Classification Search
USPC .......................................................... 705/3
See application file for complete search history.

(56) References Cited

U.S. PATENT DOCUMENTS

| | | | |
|---|---|---|---|
| 5,911,687 A | 6/1999 | Sato et al. | |
| 6,849,045 B2 * | 2/2005 | Iliff | 600/300 |
| 7,058,584 B2 * | 6/2006 | Kosinski et al. | 705/2 |
| 7,860,725 B2 * | 12/2010 | Gopinathan et al. | 705/2 |
| 2002/0062230 A1 | 5/2002 | Morag et al. | |
| 2004/0116785 A1 | 6/2004 | Bulat | |
| 2006/0173708 A1 | 8/2006 | Vining et al. | |

FOREIGN PATENT DOCUMENTS

KR    2001-0088639    9/2001

\* cited by examiner

*Primary Examiner* — Hiep V Nguyen
(74) *Attorney, Agent, or Firm* — Garvey, Smith, Nehrbass & North, L.L.C.; Brett A. North

(57) ABSTRACT

A method and apparatus is provided comprising a technology engine designed to facilitate indirect medical consultation with health care providers and create a medical record of this indirect consultation event. In one embodiment is provided a method and apparatus for capturing electronically one or more of the following: (a) patient complaints; (b) health care provider's impression/review; (c) health care provider/patient discussion of complaint symptoms following which a treatment plan is formulated regarding health care strategy; (d) any prescription issued by the health care provider; and/or (e) a set of follow-up visits by the patient.

37 Claims, 24 Drawing Sheets

13M

16M

Physician Talk To Pharmacy

18M

Review of Medical Professional Encounter

METHOD AND APPARATUS FOR INDIRECT MEDICAL CONSULTATION

CROSS-REFERENCE TO RELATED APPLICATIONS

Priority of U.S. provisional patent application Ser. No. 60/987,658, filed 13 Nov. 2007, is hereby claimed, and this application is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND

Medical professionals are increasingly faced with growing demands for services by their patients with limited time to provide these services. This is especially true during after-office-hours time periods. Current alternatives to handle this issue primarily include using answering services and out-sourcing to after-hours telephone call centers. Answering services typically initiate a follow-up process that is rarely documented and very time intensive for health care providers. Health care providers responding to calls forwarded by answering services rarely receive any compensation for their services (or these health care providers attempt to spread the cost to all of their patients by increased "office visit fees" regardless of whether such patients taking advantage of an office visit actually use after-hours services). After-hours telephone call centers, while more time efficient, are a costly alternative (to answering services) for health care providers. Another disadvantage of these call centers is the patient is not receiving medical consultation from their health care provider, but receiving medical consultation from a third party health care provider, which can cause inconsistent treatment plans, or cause the patient to decide to go to an emergency room or after hours urgent care facility thereby increasing the overall cost of medical services.

As an example, one set of health care providers, pediatricians, practice more medicine over the phone than any other health care provider. It is believed that at least 70 percent of contact with patients occurs outside of the health care providers normal business hours. It is also believed that 80% of after-hours care is delivered via the telephone. Although current procedural terminology ("CPT") codes exist and are accepted by the American Academy of Pediatrics ("AAP") which would allow insurance reimbursement to pediatricians for such after-hours care using a telephone, few pediatricians charge for these services. Lack of billing for these types of services is due to the non-existence of a practical/workable mechanism to capture call information, along with an inability to meet minimum documentation requirements (e.g., patient records, documentation of services, and prescriptions) for reimbursement by insurance companies.

The American Medical Association ("AMA") and the AAP have recommended that health care providers be paid for services which are supplied after hours or outside of normal business hours. For example, one set of services which can be charged includes telephone calls during and after hours for physician management of a new problem, including consultation, medical management, and coordination of care which do not result in an office visit within a period of 24 hours. Another set of services includes calls for physician management about an existing problem for which a patient was seen in a face-face encounter within a period of seven (7) days. Another set of services includes calls related to care plan oversight (which can be charged per month).

There are many good reasons why these after-hours services should be charged. These include: (1) answering calls requires medical skill and expertise; (2) telephone calls in many cases are actually more cost effective compared with "face-to-face" office visits (calls are believed to increase productivity and access to health care providers, along with increasing patient satisfaction with fast access to health care providers); (3) charges for calls are associated with particular patients who take advantage of these services (and thereby prevents these costs from being spread over all patients—even those who do not use telephonic services); (4) charging for these indirect consultation (e.g., calls) services will actually improve patient documentation along with quality of care by forcing the billing health care provider to compile a more "complete" medical record of the patient (to satisfy insurance company billing requirements of the after hours patient encounter), and ultimately reduce the cost of care for patients not using the indirect consultations (e.g., telephonic care—because the non-using patients are not required to pay the costs of the indirect consultation services—as such costs will no longer need to be spread throughout the entire patient population); and (5) increases access to indirect medical consultation which lowers the amount of usage of emergency room and urgent care facilities (along with the overall cost of health care for such emergency care facilities) for those patients who would go to emergency care facilities if indirect medical consultation was not provided because health care providers could not bill for such indirect consultation.

Indirect (e.g., telephone) consultation can be considered the providing of "health care services" and a patient encounter, and liability may occur from: (a) lack of documentation for the encounter; (b) inefficient documentation of the encounter; (c) medical advice that is typically based on the patient's family member's assessment of the type and severity of the complaint; (d) medical advice limited by lack of opportunity to re-examine the patient, or ensure follow-up; (e) encounter which can involve a prescription; and (f) encounter could require a follow-up visit that must be scheduled. A good risk management strategy for health care providers should include patient notification and education regarding telephone consultations.

It is believed that the following minimum documentation will be required by insurance companies from health care providers to allow billing of telephone consultations: (a) date and time of call; (b) patient's name and date of birth; (c) reason for the call; (d) relevant patient history and medical decision (e.g., HPI, PMH, PE, Impression, and/or Plan); (e) type of service and recommended treatment plan (which can include prescription(s)); (f) total amount of time spent during telephone consultation; and/or (g) applicable CPT codes. It is also believed that insurance companies will require access/submission to charts or telephone logs. Therefore, these items should be retrievable.

Various advantages exist for addressing indirect medical (e.g., telephonic) consultation events regarding health care providers.

Capturing indirect medical (e.g., telephonic) consultation events provides more complete medical records for patients thus avoiding previous gaps in medical records for patients. Another advantage of various embodiments is to provide full documentation for telephonic consultations thereby providing reduced exposure for health care providers for liability claims where part of the medical record is missing. Because the medical record of the telephonic consultation is captured, retained, and provided to the health care provider, such can be used by the health care provider in future care for the patient, or also used if a dispute arises regarding what was actually discussed during the telephonic consultation.

Another advantage of one embodiment of the method and apparatus is the ability to document and track indirect medical consultations so that regulations limiting such indirect consultations can be more easily tracked and complied with. One embodiment of the method and apparatus provides a record which can be compiled and checked against face to face medical consultations to determine whether regulations have been complied with, even if done after the fact.

One advantage of various embodiments of the method and apparatus of the present invention is an increase in productivity of health care providers for indirect medical consultation (e.g., telephonic) by compressing consultation time (e.g., call time) between patient and health care provider, while capturing telephonic encounters, prescriptions, and/or scheduling follow-up visits. Actual consultation time is compressed because various portions of information solicitation from patients is automated (and this part of the process does not actually take up the time of health care providers).

Another advantage of various embodiments is to actually increase the availability of face-to-face access to health care providers. This is because a percentage of patients using indirect (e.g., telephonic) consultation services will actually avoid the need to schedule face-to-face visits with health care providers, who otherwise would have scheduled face-to-face visits consuming valuable face-to-face appointment slots. This reduction of patients scheduling face-to-face appointments is expected to free up space for other patients who need face-to-face appointments with health care providers. In one embodiment health care providers can set a system of prioritizing medical consultations where low acuity type consultations are handled/prioritized for indirect consultations and high acuity are handled/prioritized for face-to-face office visits. Such will increase the amount of face to face high acuity consultations available for patients.

Another advantage of various embodiments is to actually increase the ability to consult directly or indirectly with the patient's chosen health care provider. Because indirect medical consultation is believed to take less time (and be more efficient) than face-to-face consultation, the health care provider is believed to be able to handle a larger volume of total consultations when more indirect medical consultations are used.

Another advantage of various embodiments is to increase revenue of health care providers by actually billing for indirect (e.g., telephonic) consultation events. These embodiments elevate indirect (e.g., telephonic) consultations to true medical events (i.e., an event which can be billed for insurance purposes). Billing for telephonic medical consultation allows health care providers to directly bill patients taking advantage of indirect (e.g., telephonic) consultations and not spread the cost of such services to all patients, including those patients who do not take advantage of indirect consultations. This is a "pay for play" philosophy and should be beneficial in reducing escalating health care costs for patients who do not use and will not have to absorb part of the costs of indirect (e.g., telephonic) consultations.

Another advantage of various embodiments is an overall higher quality of care because patients are receiving more medical consultation from their health care provider, and not resorting to third party health care providers such as emergency room care, or after hours urgent care facilities. This is believed to provide a better consistency in medical care by reducing the overall number of health care providers participating in the patient's care along with increasing overall patient satisfaction regarding the health care provided by their health care provider.

Another advantage of various embodiments is that they are believed to increase the quality of care from health care providers by increasing the amount of medical documentation for all medical events, especially medical events involving indirect medical consultations. It will capture a complete record of the complaint, the recommended plan including required therapy and/or the prescription and/or follow up visit.

Another advantage of various embodiments is to provide a complete medical record for health care provider protection. For example, should the patient not perform the health treatment plan, complete the therapy, and/or attend a recommended follow-up visit, complete documentation will be available for the event removing the problem of faulty memories and thereby protecting the health care provider and confirming the entire medical event. A complete medical record will be available to protect the health care provider, where the health care provider is later challenged to the effect that inadequate medical care was provided.

Another advantage of various embodiments is to provide more complete records for insurance companies to perform surveys on different protocols which can increase the ability of insurance companies to analyze protocols for input to setting premiums. The method and apparatus can also allow better analysis of treatment protocols to determine the efficacy of such treatment protocols. For example, the tracking of the indirect medical consultation with treatment plans, and follow up visits can be used to statistically determine the efficacy of specific treatment plans (e.g., whether the treatment plans actually worked for patients with specific complaints).

An advantage to health care providers using this method and apparatus is an increase in patient satisfaction because patients do not have to use emergency room or face to face urgent care facility visits to receive medical consultations in many instances. In general people desire to have access to their own (i.e., previously selected and used) health care providers and various embodiments of the method and apparatus allow such access. Without the method and apparatus, patients needing urgent cart are more likely to go to an emergency room facility where the patients will not see their own health care providers, but new health care providers who the patients are not familiar with.

Patients today are unaware that indirect medical consultations (e.g., telephonic consultations) are generally not documented. In the future patients will want the ability to switch health care providers and have complete medical records to facilitate a switch. Additionally, as medical records are converted more and more to pure electronic records, the complete record will allow a higher quality remote care, if needed by the patient. For example, the patient may be away from home and need quick care and quick access to the medical record, and various embodiments of the method and apparatus will allow quick access to the complete record. Various embodiments of the method and apparatus allow medical events occurring outside of the health care provider's office (which were an earlier gap) to be fully documented. Accordingly, health care providers not having complete medical records may lose patients because they cannot offer the same level of ability to switch to new health care providers.

In this application the term "health care provider" includes an individual or organization providing medical consultation and/or treatment. It can include, but not be limited to a medical doctor, surgeon, or other individual licensed to provide medical consultation and/or treatment.

In this application the term "indirect medical consultation" includes a person seeking medical consultation which is not given in a face-to-face office visit with a health care provider.

In this application the term "patient" also includes a person seeking indirect medical consultation on behalf of another individual. In this application the person seeking indirect medical consultation can include the patient, or another individual assisting the patient in the seeking of medical care. For example, the parent of a sick child may be the person seeking indirect medical consultation. As another example, a heath care professional may be the person seeking indirect medical consultation (such as by an emergency room doctor seeking to consult with the patient's primary doctor).

In this application the term "capture" is intended to include, but not be limited to, the electronic recording of, storage of, and/or transmission of information for future review.

Conventional practice is time-consuming, requiring multiple telephone calls involving the patient, the health-care provider, pharmacy, and third-party answering services or nurse-triage call-centers. Additionally, conventional practice generally does not adequately document telephone consultations.

Lack of documentation can result in: (a) less-than-ideal medical care; and that, in turn, leading to increased practice costs due to increased liability and (b) making it difficult, if not impossible, for physicians to bill for these services.

There is a need to provide health care providers with the capability of compiling electronic medical records (EMRs), and collecting sufficient information to charge for these encounters.

Conventional Ad-Hoc Approach

Conventional practice has indirect medical consultation with health care providers being performed on an ad-hoc basis: (1) patient dialing the health care provider's telephone number; (2) message being taken by the heath care provider's answering service which can collect identifying information, telephone number, and a description of the patient's complaint; (3) answering service providing health care provider with the information about the patient's call; (4) If necessary, the health care provider telephoning patient; (5) If necessary, the health care provider issuing a prescription by telephoning or faxing patient's pharmacy; (6) The health care provider may telephone office personnel and leave instructions on contacting the patient to schedule an office visit; and (7) The health care provider may telephone a medical-transcription system and dictate a note for the patient's chart.

There are various disadvantages of the ad hoc approach.

(1) It is expensive: Every telephone call from a patient requires human intervention, at least by the health care provider's answering service. Some practices use nurse-triage centers, which substantially elevates the cost of handling these calls.

(2) It is time-consuming: The health care provider may have to make multiple telephone calls: to the call center, to the patient, to the patient's pharmacy, to his/her office to schedule an office visit or note information in the patient's medical record.

(3) It may be not be accurate: The health care provider's initial contact with the patient is through the call-center operator, who may or may not present the patient complaint and contact information accurately.

(4) There is no "record" about the contact. The contact may not be noted in the patient's chart. Likewise, medications prescribed for the patient may not be recorded, resulting an incomplete medical record for this patient.

(5) Such contacts are rarely billed by a health care provider. This is despite the fact that they are a professional service that the health care provider provides to his/her patients, and that properly documented telephone consultations are eligible for reimbursement by insurers.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

BRIEF SUMMARY

The method and apparatus of the present invention solves the problems confronted in the art in a simple and straightforward manner. In one embodiment is provided a method and apparatus for seeking and providing indirect medical consultation services. In one embodiment is provided a telephone-based service for capturing items to be included by health care providers in their medical records which is set up for health care providers to assist the providers in telephone consultation, evaluation, and treatment planning, along with an record of the consultation, prescription, follow-up, and/or treatment plan.

In one embodiment is provided a method and apparatus to manage telephone consultations between heath care providers and patients.

In one embodiment is provided a method and apparatus comprising a technology engine designed to address unique requirements associated with indirect (or non-face-to-face) consultations with health care providers, such as medical consultations using a telephone. In one embodiment is provided a method and apparatus for capturing electronically one or more of the following: (a) patient disclosure/complaint/history/background; (b) health care provider's impression/review; (c) health care provider/patient plan regarding health care strategy; (d) any prescription issued by the health care provider; (e) billing information for indirect consultation; and/or (f) scheduling of follow-up visit(s) by the patient.

In one embodiment is provided a method and apparatus for capturing electronically the indirect (e.g., non-face-to-face or telephonic) medical consultation event. In one embodiment this record of such consultation is transmitted to the health care provider. In one embodiment this record can be of a multi-media type such as text, graphic, and/or sound electronic files for documenting the telephonic event.

In one embodiment a data storage service is provided where various parts of the indirect consultation (e.g., telephonic event) are stored for the health care provider for later access and/or transcription.

In one embodiment a transcription option can be provided for creating an electronic text file from other types of records. For example, recorded messages can be transcribed to be available in a searchable text file (or word processing file). In one embodiment the transcription service can be selected where the sound portion of the telephonic event is recorded.

In one embodiment is provided a method and apparatus to capture a substantial portion of an indirect (e.g., non-face-toface such as telephonic) medical consultation. For example, the following portions of a medical consultation can be captured: (a) information provided by the person seeking indirect medical consultation before contact with the health care provider; (b) information provided by the person seeking indirect medical consultation during contact with the health care provider; (c) information provided by person seeking indirect medical consultation while in contact with the health care provider and/or, after the initial complaint by the person, information provided by such person responding to a health care provider's request for additional information; (d) information provided by health care provider to person seeking indirect medical consultation; (e) any diagnosis(es) by health care provider; (f) any treatment plan(s) issued by the health care provider; (g) any prescription(s) issued by health care provider; and/or (h) any supplemental information provided by the health care provider. In one embodiment one or more of the above items are captured or recorded by the method and apparatus. In one embodiment one or more of the above items can be captured/recorded by the method and apparatus, and sent to the health care provider. In one embodiment one or more of the above items of information can be captured/recorded by the method and apparatus, and stored in a data storage device for future access by the health care provider.

In one embodiment certain information can be captured from a patient before the patient is placed in contact with a health care provider. In one embodiment one or more of the below referenced items are captured from the patient before the patient (or the person seeking medical consultation) is placed in contact with the health care provider: (a) at least a portion of the patient's social security number (e.g., entering the last 4 digits of social security number); (b) the name of caller; (c) patient name; (d) patient birth date; (e) approximate the date of last visit; (f) telephone number for a callback; (g) reason for the call/type of medical consultation being sought; (h) medical history; (i) drug allergies; (j) preferred pharmacy; (k) pharmacy city; and/or (l) pharmacy address or street. In one embodiment voice recognition technology can be used for capturing one or more of the above listed items.

In one embodiment is provided a method and apparatus having an automated approach for health care providers who provide telephonic medical consultations to their patients while improving the quality of medical care, increasing productivity of the health care providers, reducing liability of the health care providers, generating revenue streams for medical services rendered, but not previously billed, and reducing the overall cost of health care by reducing the amount/frequency of emergency/urgent care facility used by patients.

In one embodiment health care providers providing telephone medical consultation services, primarily during, but not limited to, after hours care can take advantage of the method and apparatus.

In one embodiment a telephonic and systematic platform is provided allowing health care providers the ability to efficiently diagnose, create, and initiate a treatment plan; and bill for patient reported medical problems.

In one embodiment the person seeking medical consultation is notified by the method and apparatus that the information provided by such person will be forwarded to the health care provider, and the health care provider will be requested to contact the person seeking medical consultation.

In one embodiment of the method and apparatus, a health care provider is notified that an indirect medical consultation has been requested and is waiting for a response. In one embodiment a health care provider selected by the method and apparatus is notified. The health care provider selected can be based on a list of health care providers provided to the method and apparatus for health care providers taking advantage of the method and apparatus. For example, database calendar of "on call" health care providers can be used by the method and apparatus.

As another example, the health care provider can customize the method and apparatus to randomly select from a specified database of health care providers, a responding health care provider for persons seeking indirect medical consultation. In one embodiment a specific order of responding health care providers can be specified by a primary health care provider. As another example, the person seeking the indirect medical consultation from a practice group of health care providers can be responded to by a specific health care provider individual who is selected by the health care provider practice group based on customized procedures for this practice for responding to indirect medical consultations.

In various embodiments, the method and apparatus places the patient in indirect medical consultation with the patient's previously selected primary health care provider. In one embodiment this selection of the primary health care provider is by the patient telephoning the telephone number of the health care provider.

In one embodiment the selected health care provider is notified of the requested event for indirect medical consultation, and that this request is waiting for a response. In one embodiment the selected health care provider is notified by one or more the following notification means: phone, facsimile, texting, paging, email, internet, personal notice, etc.

In one embodiment the notified health care provider can access the method and apparatus to access the information captured by the method and apparatus.

In one embodiment access can be provided by a secure log in process with security protocols. For example, the health care provider can phone into the method and apparatus using a secure sign-on process: (a) dials in using phone number established for office; (b) enters an individual identifying indicia (such as for individual identification for groups of health care providers); and (c) enters a user defined password.

In one embodiment by accessing the method and apparatus, the captured information is made available to the health care provider. For example, a compiled message of the information supplied by the person seeking indirect medical consultation can be played to the health care provider. In one embodiment, at this point, the health care provider makes a decision regarding whether enough information has been gathered for a diagnosis.

If the health care provider decides that there is enough information to adequately diagnose the patient's condition giving rise to the request for indirect medical consultation, the health care provider can diagnose the condition, formulate a treatment plan, issue a prescription, schedule an office visit with the patient (such as through the health care provider's office staff), and/or instruct the patient to schedule an office visit. In one embodiment the method and apparatus can electronically capture the health care provider's diagnosis, such as by electronically recording a health care provider's oral statement of diagnosis.

In one embodiment the health care provider is provided with a series of options for the capture of his diagnosis which can include: typing, handwritten/scanned, email, internet, etc. all of which can be electronically captured by the method and apparatus. In one embodiment a multiple of options/means for redundantly electronically capturing the health care provider's diagnosis are provided to the health care provider.

If the health care provider decides that there is not enough information to adequately diagnose the patient's condition giving rise to the request for indirect medical consultation, the health care provider is given the option of using the method and apparatus to contact the patient. If the health care provider elects to make contact, the method and apparatus can automatically attempt to make contact such as by using the contact information supplied by the person seeking indirect medical consultation. In one embodiment, if the first attempt at contact is not successful, the method and apparatus can be used to make a plurality of attempts to contact the person seeking indirect medical consultation while the health care provider does other activities and, when contact is finally made, notice can be sent to the health care provider for direct contact. As with other embodiments notice to the health care provider of obtaining contact with the person seeking indirect medical consultation can be sent to the health care provider through phone, facsimile, texting, paging, email, internet personal notice, etc. Once the person seeking indirect medical consultation is contacted, contact with such person can be maintained by the method and apparatus until the health care provider is also contacted by the method and apparatus, so direct (although non-face-to-face) communication between the health care provider and person seeking indirect medical consultation can begin.

In one embodiment an option for the health care provider to have the method and apparatus use recorded messages for additional information from the person seeking indirect medical consultation can be provided. This option may be useful where the health care provider cannot be available for immediate contact with the person seeking indirect medical consultation, and/or the patient is not available. Here, the health care provider can record a series of questions and/or requests, and have the method and apparatus contact the person seeking indirect medical consultation, with the method and apparatus capturing the responses, and then transmitting the responses back to the health care provider. Here, the patient can listen to the series of questions/statements by the health care provider and respond to same with the responses being recorded, and then transmitted to the health care provider.

In one embodiment a substantial portion of the direct contact between the health care provider and the person seeking indirect medical consultation can be electronically captured by the method and apparatus such as by recording of oral statements, recording of texted messages, recording of typed messages, and/or recording of other types of communication between the health care provider and the person seeking indirect medical consultation. Once the health care provider decides that enough information has been obtained, the health care provider can make a diagnosis. Optionally, the health care provider can decide that a diagnosis should not be made at this time, but some other form of medical consultation should be pursued. For example, the health care provider can recommend that a follow-up visit be scheduled. In one embodiment a message is sent to the health care provider's office that a follow-up appointment needs to be scheduled and the health care provider's office can initiate the scheduling of the follow-up appointment. In one embodiment, the follow-up visit can be automatically scheduled by the method and apparatus. As another example, the health care provider can recommend that the patient be taken to an emergency care facility (such as a hospital emergency room).

In one embodiment the health care provider can decide on a treatment plan. In one embodiment the method and apparatus can electronically capture the treatment plan from the health care provider. The electronic capturing of the treatment plan can be by oral recordation of statements from the health care provider, or by storing a text of the treatment plan obtained from the health care provider.

In one embodiment the health care provider can issue a prescription. In one embodiment the method and apparatus can electronically capture the prescription. In one embodiment voice recognition technology can be used with the health care provider stating the prescribed drug(s) name and the method and apparatus checks it against a predefined database. Once the proper prescribed drug is identified this information related to the prescribed drug (along with its National Drug Code "N-D-C" number) can be sent to the selected pharmacy. In one embodiment the method and apparatus can transfer/send the prescription to a pharmacy. In one embodiment the prescription can be sent to the pharmacy selected in the first step of electronic data capture from the person seeking indirect medical consultation. In one embodiment the prescription can be sent to a pharmacy selected by the health care provider. In one embodiment the prescription can be sent to a pharmacy selected by the method and apparatus, such as from a database of pharmacies within a preset limit from a preselected geographical point (such as the location of the patient). In one embodiment the method and apparatus can perform a check with the pharmacy to ensure that the pharmacy in which the prescription is being sent is an approved pharmacy for the medical insurer of the patient.

In one embodiment even though a prescription and/or health treatment plan has been issued/created, the health care provider can recommend that a follow-up visit be scheduled. In one embodiment a message is sent to the health care provider's office that a follow-up appointment needs to be scheduled and the health care provider's office can initiate the scheduling of the follow-up appointment. In one embodiment, the follow-up visit can be scheduled by the method and apparatus. As another example, the health care provider can recommend that the patient be taken to an emergency care facility (either a hospital emergency room or after hours care facility).

In one embodiment the option is provided to the health care provider to record additional information related to the person seeking indirect medical consultation, patient, diagnosis, treatment plan, and/or follow up visits.

In one embodiment the heath care provider is provided with the option to delete, modify, add to, and/or supplement one or more of the types of data captured (e.g., patient information, diagnosis, treatment plant, and/or prescription) by the method and apparatus.

In one embodiment the method and apparatus can notify the person seeking medical care (and/or patient) of certain actions by the health care provider. For example, notice can be given to the person seeking indirect medical consultation that a prescription was sent to a specified pharmacy. In one embodiment, an option to obtain directions to the pharmacy (or a map of the pharmacy) can be provided by the method and apparatus to the person seeking indirect medical consultation. As another example, the method and apparatus can send the person seeking indirect medical consultation information (or a message) from the health care provider such as relevant follow-up steps. In one embodiment such post contact information is also captured by the method and apparatus for future access by the health care provider and/or patient.

In one embodiment the method and apparatus provides a notification to the health care provider of certain follow-up activities. For example, the method and apparatus can notify the health care provider of a required treatment follow-up or that a follow-up appointment should be scheduled. In one embodiment the method and apparatus provides a notification to the office/staff of the health care provider of a required follow-up appointment. For example, the method and apparatus can notify the staff that a follow-up appointment for this patient should be made and the staff can contact the patient/original person seeking indirect medical consultation for scheduling the follow-up appointment.

In one embodiment all data in compiling a medical record of the medical consultation event is electronically captured by method and apparatus and transmitted electronically to the health care provider. In one embodiment the information is stored and the health care provider can access and/or retrieve such electronically stored information at a later point in time. In one embodiment the entire recorded event is captured electronically (such as by a WMV file) and sent to the health care provider for record retention and billing.

In one embodiment a real-time electronic prescription service can be provided. In this embodiment a prescription database customized to the health care provider can be provided. In one embodiment a plurality of field specific prescription databases related a plurality of fields of health care can be provided. In one embodiment one or more of these specific databases can be individually customized for a particular health care provider at the option of the health care provider. Additionally, access to one or more of these individually customized databases (for selection, addition, deletion, and/or correction) can be through speech recognition algorithms.

In one embodiment a follow up visit to the telephonic event is scheduled with the health care provider. In one embodiment a message is sent to the health care provider's office that a follow-up appointment needs to be scheduled and the health care provider's office can initiate the scheduling of the follow-up appointment. In one embodiment this follow up visit is electronically scheduled by the method and apparatus.

In one embodiment a health care provider can establish a service and configure a customized automated call system via an electronic interface, such as a web-interface. A patient can initiate a telephone consultation by calling into the automated system and responding to a set of pre-defined prompts. The automated system can then contact the health care provider through various means, such as through an electronic signal (e.g., web-interface, email, radio, telephone, pager, facsimile, infrared, etc.) notifying the health care provider of the patient event. The health care provider can review the patient input (and in one embodiment a medical history for the patient) via a call-in system and diagnose the event or, optionally, contact the patient for additional information (which contact can be facilitated and captured automatically through the method and apparatus).

In one embodiment, after diagnosing and determining the treatment plan, the health care provider can use the method and apparatus to automatically call the patient and/or a pharmacy selected by the patient (for submitting a prescription order if deemed appropriate by the health care provider).

In various embodiments one or more steps of the method can be simplified by the health care provider using customized voice recognition options.

In one embodiment a portion or all events can be recorded and electronically sent to the health care provider for data retention/documentation and billing (if applicable).

In one embodiment, if a follow-up visit is required, the health care provider's office can be notified to schedule the appointment.

In one embodiment a proprietary prescription database can be updated by the method and apparatus.

Although certain information may be automatically obtained by the method and apparatus from the person seeking indirect medical consultation, nothing in this method and apparatus is intended to restrict and/or prevent the health care provider from directly contacting such person or seeing such person in a face to face office visit where the health care provider deems this necessary or preferable.

In one embodiment is provided an automated solution to the problem of managing telephone contacts between patients and health care providers focusing on after-hours care. In one embodiment telephony features can be used to automate the handling of patient encounters: (1) in one embodiment a plurality of pre-recorded messaging or scripts can be used to handle inbound calls and make outbound calls; (2) in one embodiment information about the encounter is recorded for a record compilation; (3) in one embodiment voice recognition technology can be used to transform speech into text; (4) in one embodiment Text-to-speech technology can be used to recite information or messages to the patient and the health care provider when recorded prompts are not available, or are not practical; (5) in one embodiment interactions with databases and other remote sources of data can be used; (6) In one embodiment one or more of the following computing features can be used: (a) relational databases, to hold metadata used to run the method and apparatus, and to hold information about the telephone calls generated during the encounter, and information specific to the patient and his treatment, (b) reporting system, to extract information from the database, organize it, and make it available to authorized parties.

In one embodiment the method and apparatus includes one or more of the following features: (1) eliminating the need for a human operator; (2) using pre-established databases to validate the accuracy of the collected data, as well as increasing the efficiency of call-handling whenever possible; (3) collecting or recording information from the patient: identification information, contact information, preferred pharmacy, and chief complaint. Improve efficiency by using pre-established databases to validate the names of patients and pharmacies whenever possible; (4) presenting patient information to the health care provider; (5) recording instructions from the health care provider for the patient; (6) recording instructions from the health care provider to practice's personnel concerning a follow-up appointment, should one be needed; (7) recording notes from the health care provider, to be transcribed for the patient's medical record; (8) collecting prescriptions, if necessary, from the health care provider. The method of collecting this information is discussed at greater length below; (9) transmitting instructions to the patient, the pharmacy, the health care provider, the appointment system, and the medical-record system; (10) managing errors in the collection and transmission of information: from the patient, to the health care provider, to the pharmacy, to the patient, to the appointment system, or to the medical-record system; (11) storing a complete, detailed set of information about the encounter; and (12) reporting the patient encounter to the health care provider.

In one embodiment the method and apparatus can be multiuser and able to support multiple health care providers, from multiple practices, representing multiple specialties. In one embodiment the method and apparatus can handle thousands of health care providers, and millions of patient contacts per year. In one embodiment the method and apparatus can be easily administered. In one embodiment it is easy to add new health care providers and practices, and modify existing health care providers and practices. In one embodiment the method and apparatus can work with practices of varying levels of sophistication. In one embodiment a minimum level of technological sophistication is specified to use the method and apparatus. In one embodiment the method and apparatus can be easy to use for patients, health care providers, and pharmacists.

In one embodiment the method and apparatus handles various forms of "operational data" which can include data that describe one or more of the following: (1) Practices; (2) Medical specialties; (3) Health care providers, and the practices and specialties they are associated with; (4) Patients, including identifying information; (5) Pharmacies: their name, their location, and contact information; and (6) Drugs: their names dosages, and, possibly, their formulary validation.

In one embodiment the method and apparatus can handle various forms of "collected data" which can include data for one or more of the following: (1) Description of calls from medical professionals to the health care provider: (a) Calls associated with a patient encounter managed by the method and apparatus and (b) Calls associated with a patient encounter other than one managed by Method and apparatus; (2) Descriptions of calls from patients that initiate a patient encounter; (3) Descriptions of calls from patients that follow up a patient encounter (a) patient call-backs in response to a message from the method and apparatus and (b) Patient call-backs to check on the progress of an encounter; (4) Information elicited from the patient during the call, including: (a) Identifying information (e.g., name, gender, SSN, date of birth, or other identifiers), (b) The patient's location, based on ZIP code, (c) The patient's preferred pharmacy, (d) The telephone number at which the patient can be contacted, and (e) The recording of the patient's complaint; (5) Calls dialed to the health care provider, (6) Calls received from the health care provider; (7) Information elicited from the health care provider about a given encounter: (a) Instructions to the patient, if any, (b) Prescriptions for the patient, if any, (c) Instructions for follow-up appointment for patient, if any, and (d) health care provider's notes for patient's medical record, if any; (8) Record of contact dialed to patient; (9) Record of contact with pharmacy to deliver prescriptions; (10) Record of contact with the health care provider's appointment method and apparatus, to deliver the health care provider's instructions concerning a follow-up appointment; and (11) Record of contact with the health care provider's medical-record method and apparatus, to deliver the health care provider's notes.

In one embodiment the method and apparatus can perform various data management tasks that can include one or more of the following issues: (1) Importing data from other information systems such as: (a) information about practices (for each practice that is participating, the following information can be included (i) a description of the practice: name, physical address, telephone number, (ii) a description of the information systems used by the practice, and how to interact with them, (iii) a list of the health care providers who are associated with the practice; (b) Information about health care providers which can include one or more of the following: (i) Demographic information: name, address, telephone number, (ii) Specialty, (iii) Schedule: hours available in office, hours available for telephone consultation, and (c) Information about specialties including (i) Description, (ii) Medications usually prescribed via telephone consultation, (d) Information about medications including (i) Name, (ii) Generic name, (iii) Usual range of dosages, (iv) Usual regimens, and (v) Drug interactions; (d) Information about patients, for confirmation, constructing electronic records, notifying office-scheduling method and apparatus, and constructing messages for automated prescription-fulfillment method and apparatus; (e) Information about pharmacies including (i) Name, (ii) Affiliation, (iii) Location, (iv) Hours of operation, (v) Contact information, and (vi) Method of uploading prescriptions; (f) Contact information about health care providers such as name, physical address(es), telephone number(s)s, email address(es); (2) Storing data; (3) Reporting data; and (4) Exporting data to health care providers and other systems.

In one embodiment the method and apparatus is portable and usable on various platforms and providers, application-specific data—both metadata that control the operation of the method and apparatus, and data generated in the course of executing patient encounters—can be stored in tables that are written specifically for this application, rather than in the general-purpose tables.

In one embodiment one or more of the following sets of reports can be generated: (1) Automated reports sent to health care provider offices. These can describe each patient encounter, the steps taken, and the overall outcome of the encounter; (2) Reports generated on request. For example, summary reports can give counts and outcomes of patient encounters, broken down in a variety of ways; (3) Reports used internally, for auditing, method and apparatus maintenance, and billing; and (4) Tools, preferably using the internet and/or world-wide web, to administer the method and apparatus. In particular, tools will be needed to set up and administer health care provider accounts, and to enter and update personal and family data about patients.

In one embodiment the method and apparatus can be HIPAA-compliant. In one embodiment the following security issues can be addressed: (1) Platform security. The platform must be guarded scrupulously against "hacking". This is to prevent interception of confidential information, and to stop intruders from using the method and apparatus to generate fraudulent transactions; (2) Database security. Access to the database must be tightly controlled, to prevent access to confidential patient data by unauthorized persons; (3) User identification. Identification information will gathered from users, both health care providers and patients. This information will be verified against information either stored in a local database or retrieved interactively from a remote source; (4) Online security. Users' connections to update data within the method and apparatus (e.g., health care providers telephone numbers) must at least be password protected, and encrypted protocols used. (e.g., https); and (5) Report security. Reports being emailed to health care providers and administrators must be encrypted, using public keys that are stored on the platform.

In one embodiment the method and apparatus can assist health care providers in performing telephone consultations with their patients. In one embodiment the method and apparatus can provide patients with an improved standard of care, and help health care providers both to make more efficient use of their time, and to be compensated for these consultations.

In one embodiment is provided an option where an assistant to the health care provider (such as a nurse practitioner) can first be notified of an encounter from a patient or medical professional, and allowed to pre-screen such encounter before sending the particular encounter on to the health care provider. In this embodiment it is envisioned that the screening assistant can reduce the workload of the health care provider for encounters which may be relatively easily addressed and within the screening assistant's area of competency. To take advantage of this option, the health care provider (e.g., doctor) has the option of enabling patient and/or medical professional encounter-screening queues to be managed by a screening assistant (e.g., nurse practitioner)—which screening assistant can be selected by the health provider. The screening assistant can be notified by the method and apparatus of encounters via the screening assistant's selected method of notification (e.g., phone, text, pager, email, fax, etc). In one embodiment the screening assistant can connect to the method and apparatus through a secure, password protected, sign-on method and select the encounter queue to be reviewed (where there is more than one possible encounter queue for the screening assistant—e.g., patient encounters and/or medical professional encounters). The options for the screening assistant when reviewing encounters can be similar to the described options provided to the health care providers when reviewing encounters. If the screening assistant can handle the encounter without involving the health care provider, the screening assistant will handle and close such encounter. With encounters handled by the screening assistant, after triaging the encounter or responding to the medical professional, the screening assistant can close the encounter so that the encounter is closed and reported similar to encounters closed by the health care provider (but without requiring the time of the health care provider). However, if the screening assistant determines that the encounter should be handled by the health care provider, the screening assistant will have an option (such as by hotkey or voice recognition) to send such encounter to the health care provider's queue or respective queue (e.g., where there are multiple health care provider queues, such as patient or medical professional complaint queues). If sent to the health care provider, the encounter will be handled by the health care provider as described for encounters not having a pre-screening option.

The drawings constitute a part of this specification and include exemplary embodiments to the invention, which may be embodied in various forms.

BRIEF DESCRIPTION OF THE SEVERAL VIEWS OF THE DRAWINGS

For a further understanding of the nature, objects, and advantages of the present invention, reference should be made to the following detailed description, read in conjunction with the following drawings, wherein like reference numerals denote like elements and wherein.

DETAILED DESCRIPTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

Figure 1:
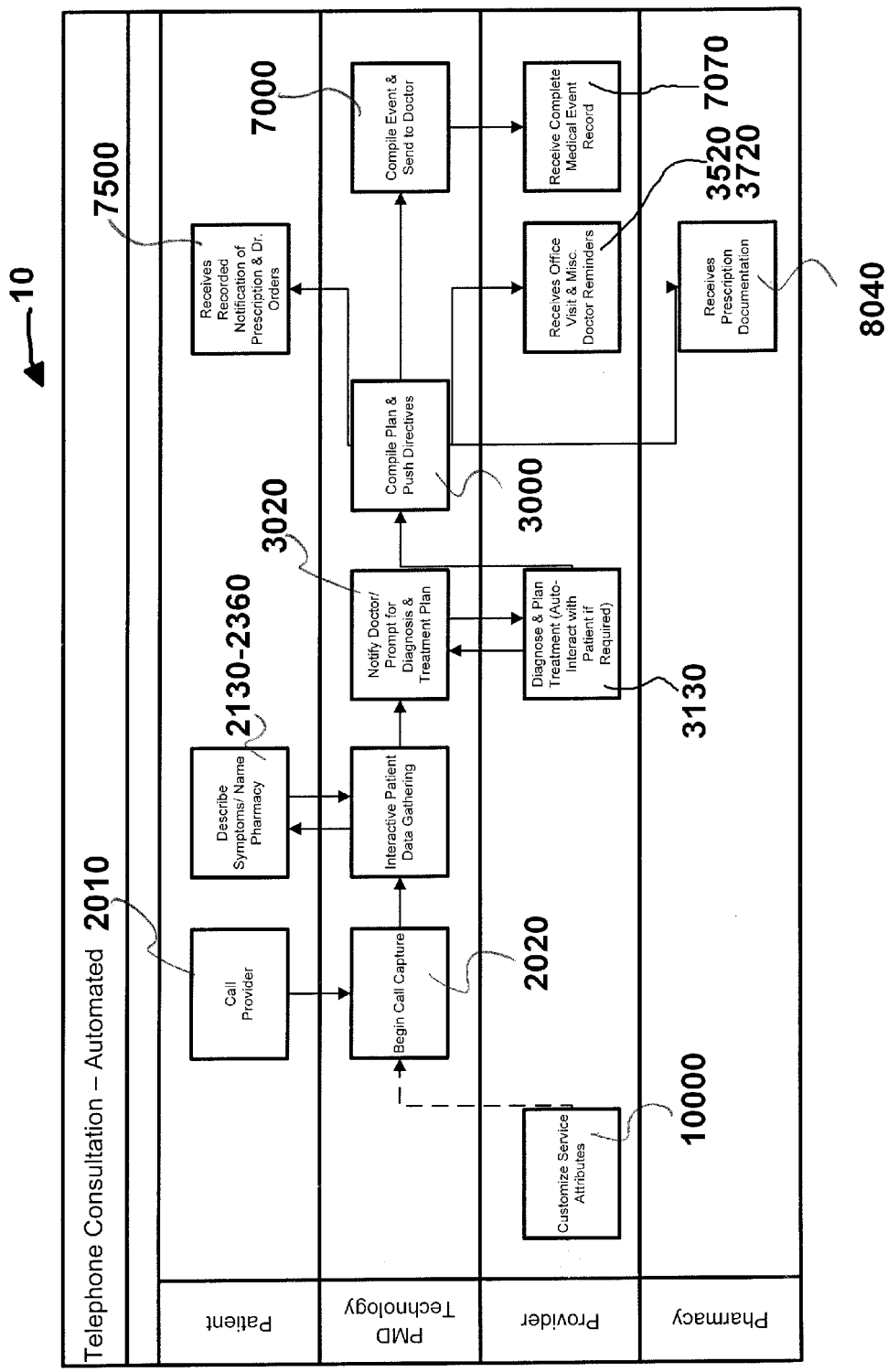
FIG. 1 is a high level flow chart of the method and apparatus.

FIG. 1 is an overall flow chart of the method and apparatus 10 addressing patients with consulting/contacting health care providers outside of providers' offices. Such consultation/contact can be outside of normal business hours for health care providers, or during normal business hours where the patient decides not to, or cannot come to the provider's office. When a need arises the patient can use the method and apparatus 10 to contact the health care provider in seeking medical consultation. The patient can call the health care provider's office and the method and apparatus 10 takes over the telephone call which method and apparatus enters a call data capture mode and starts recording patient input. Patient input can be both oral, selection (voice recognition/telephonic input), and/or other (e.g., there can be a web interface where persons seeking indirect medical attention can contact a health care provider).

In one embodiment the patient responds to a plurality of pre-formatted questions set forth by the health care provider. Examples include name of patient, social security number, telephone number, address, preferred pharmacy, complaint (e.g., medical situation, such as a list of symptoms), and/or known allergies. In one embodiment, the patient can select from a menu of possible selections regarding one or more of the above listed items.

In one embodiment the method and apparatus notifies/contacts the health care provider and supplies at least part of the information obtained from the patient. In one embodiment this notification can be by telephone, email, fax, text, and/or pager.

In one embodiment the method and apparatus can comprise a computer, which can be a host computer, network computer, personal computer, and/or notebook computer.

In one embodiment the method and apparatus includes a display for the health care provider to supply input, receive output, operate, and/or supply commands to, with, and/or from the method and apparatus. In one embodiment the display can comprise a computer, telephone, and internet. In one embodiment the computer can be a host computer, network computer, personal computer, and/or notebook computer.

In one embodiment the method and apparatus includes a memory for recording and/or compiling one more items of information supplied to the method and apparatus and/or obtained from the method and apparatus. Such items of information can include information obtained from the person seeking indirect medical consultation. Such items of information can include information obtained from the health care provider. Items of information can be any item of information described in any step of the method and apparatus.

In one embodiment the method and apparatus can comprise a communication means such as the telephone, internet, radio, etc. along with a data storage device. In one embodiment the communication means can be a computer. In one embodiment the data storage device can be a computer. In one embodiment the method and apparatus facilitates consultation with a health care provider such as a doctor. In one embodiment the method and apparatus electronically captures a conversation between a health care provider and a patient communicating electronically, such as through the telephone, internet, text messaging, radio, etc.

In one embodiment the health care provider can issue a diagnosis and/or treatment plan or optionally contact the patient, consult, and then issue a diagnosis and/or treatment plan.

In one embodiment the conversation between the health care provider and patient is saved in a database for future reference. In one embodiment the conversation between the health care provider and patient can be subsequently accessed by the health care provider, such as by being downloaded in electronic format by the health care provider. In one embodiment the conversation between the health care provider and patient is electronically sent to the health care provider.

In one embodiment the method and apparatus compiles a plurality of encounters for a health care provider to address, and the health care provider can access same through the method and apparatus.

In one embodiment the method and apparatus compiles a plurality of encounters for a plurality of health care providers to address, and each health care provider can access his plurality of encounters through the method and apparatus.

In one embodiment a plurality of health care providers are provided with unique identifying indicia.

Figure 2A:
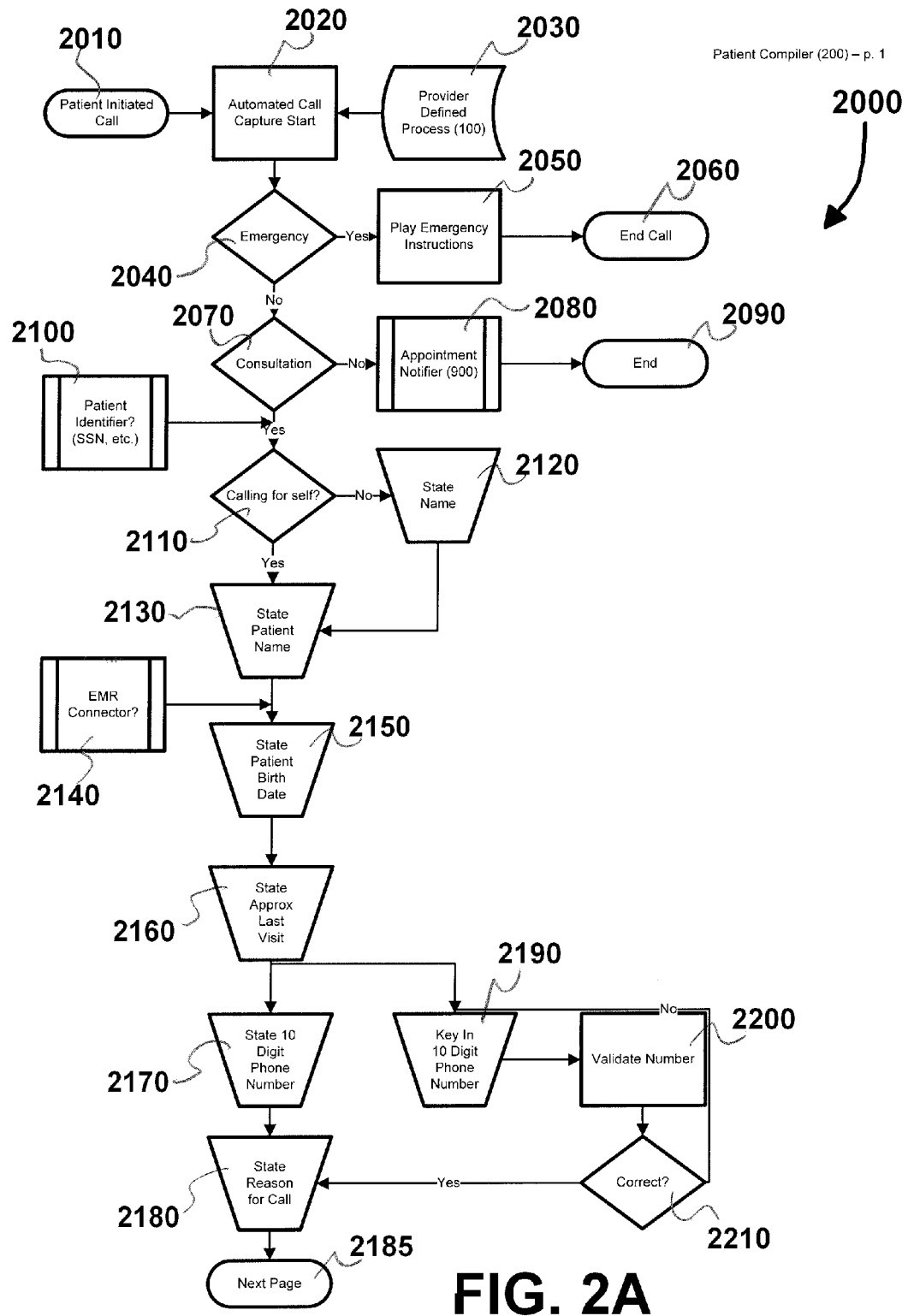
FIGS. 2A and 2B are a flow chart of the patient compiler portion of the method and apparatus.
Figure 2B:
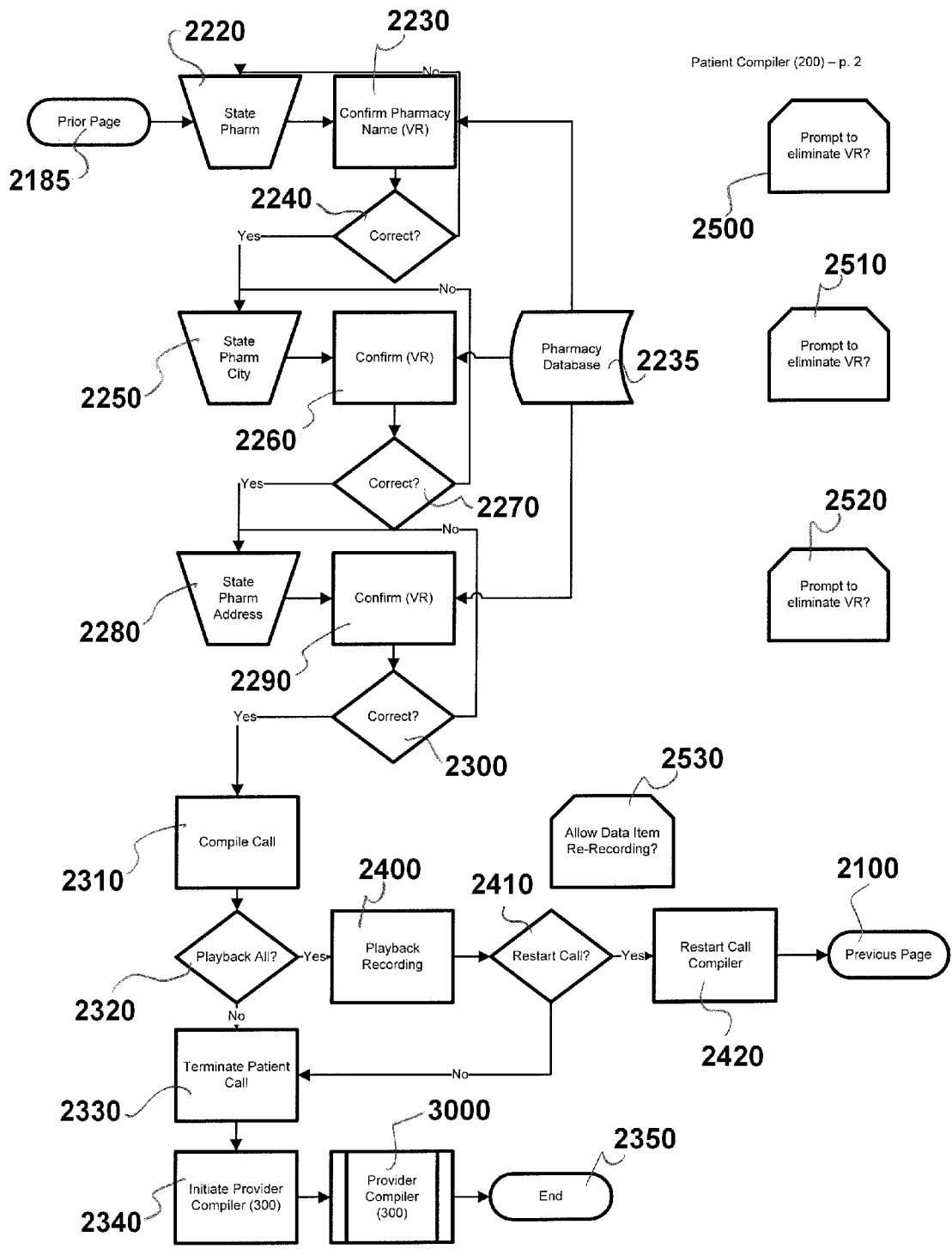

FIGS. 2A and 2B are a flow chart 2000 of the patient compiler (200) portion of method and apparatus 10.

In step 2010 patient initiates a call to a health care provider. Step 2020 indicates that an automatic call capture starts where information from the patient can be captured and recorded for the health care provider and medical records. Step 2030 indicates that call capture can be from a provider defined process 100. The provider defined process indicates that a health care provider can customize the data capture portion from the patient such as by requiring that specified information be obtained from the patient, or specified questions asked.

Step 2040 indicates that a query is made regarding whether the call has been initiated as an emergency. If the call is specified as being an emergency, then in step 2050 emergency instructions are played for the caller. Such instructions can typically recommend that the caller call an emergency service such as 911 or go to the emergency room of a hospital.

If the call is not indicated as being an emergency, then in step 2070 a query is made regarding whether an indirect consultation is being sought or whether an office appointment is desired. If an office appointment is desired, in step 2080 the Appointment Notifier 900 is activated and in step 2090 the call is ended.

If indirect consultation is selected, then in step 2100 patient identifying information is solicited such as name, social security number, etc. In step 2110 the caller is queried regarding whether the consultation is for himself or for another. If the answer is that the consultation is not for himself, in step 2120 the caller is requested to identify his name, and in step 2130 the caller is requested to identify the patient's name. If the consultation is for the caller, then step 2120 is skipped and step 2130 is proceeded to.

Once the patient's name is identified, step 2140 provides the option for a database of electronic medical records for the identified patient, to be associated with the data captured with the method and apparatus. This associating of the electronic medical records can allow the health care provider (who can electronically review these records) to have a more complete medical record when diagnosing the case or preparing a treatment plan later on in the process.

In step 2150 the patient's birth date is provided. In Step 2160 the date of the last office visit is provided, or at least an approximate date of the last office visit. In step 2170 a return telephone number for the person soliciting indirect medical consultation is orally provided and captured/recorded. Alternatively, in step 2190 the return phone number can be keyed in by the person making the call and in steps 2200 and 2210 this provided telephone number can be validated as correct.

Next, in step 2180 the reason for the telephone call is provided. This could be the reason for seeking the indirect medical consultation such as my child is running a fever of 101 degrees and has stomach cramps.

In step 2220 a pharmacy is selected by the caller. This selection can occur by the caller's response to a question such as "please state your preferred pharmacy." Alternatively, this section can occur by the caller selecting a pharmacy from a database of pharmacies provided by method and apparatus 10. This database of pharmacies provided may be compiled from a database of pharmacies stored in the method and apparatus which are located within a predefined geographical radius from the caller's location. This database of pharmacies provided can be from various other criteria, such as pharmacies which are within the network of the patient's medical insurance (if the patient has medical insurance).

In steps 2230 through 2300 a confirmation process is used to validate the pharmacy selected in step 2220. In one embodiment this validation can be through voice speech recognition technology. In steps 2230 and 2240 the caller is requested to confirm the pharmacy name selected in step 2220. Pharmacy database 2235 can be a database of pharmacy information which includes pharmacy names associated with addresses, hours of operation, along with other information, and can be provided in the method and apparatus 10 where the caller's confirmation is checked against the pharmacy names included within database 2235. In step 2250 the caller is asked to state the pharmacy city, and in steps 2260 and 2270 the caller is requested to confirm the pharmacy city. Pharmacy database 2235 can be used by method and apparatus 10 to confirm that the pharmacy city provided in step 2250 matches the city associated with the pharmacy name in database 2235 which name matches the pharmacy name provided in step 2220 matches. In step 2280 the caller is asked to state the pharmacy address (preferably the street address), and in steps 2290 and 2300 the caller is requested to confirm the pharmacy address. Pharmacy database 2235 can be used by method and apparatus 10 to confirm that the pharmacy address provided in step 2280 matches the address associated with the pharmacy name in database 2235 which name matches the pharmacy name provided in step 2220 matches.

In step 2310 the information from the call can now be compiled in a format suitable for future access by the health care provider.

In step 2320 the option of playing back various items of information to the caller in a form that the health care provider will hear such information. If this option is not selected the initial call is terminated and the method and apparatus proceeds to step 2330.

In step 2330 the initial call is terminated, which causes the method and apparatus 10 to proceed to step 2340 (initiating the provider compiler 300), step 2350 (activating the provider compiler 300—flow chart 3000), and step 2350 ending the patient compiler 200.

Steps 2320, 2400, and 2410 provide the person seeking indirect medical consultation with the option to confirm, and/or change various items of information which were compiled in step 2310. In step 2400 various items of information can be played back to the caller in a form that the health care provider will hear such information. In one embodiment the caller is provided with the option(s) to individually change one or more items which were previously compiled without having to start from the beginning of the compilation process.

Step 2420 provides the caller with the option of terminating the call (going to step 2330) or restarting the call compilation process (going back to step 2100).

In various of the above steps voice recognition technology can be used to check, validate, and/or receive input from the caller. Steps 2500, 2510, and 2520 show options for the caller to decline the use of voice recognition technology. In one embodiment the method and apparatus 10 has a maximum number of attempts to validate, or check one or more of the selections from the user before the selection is merely recorded without validation. In one embodiment the maximum number of times are 2, 3, 4, 5, 6, 7, 8, 9, or 10 times. In one embodiment the health care provider can customize the maximum number of selections.

Figure 3A:
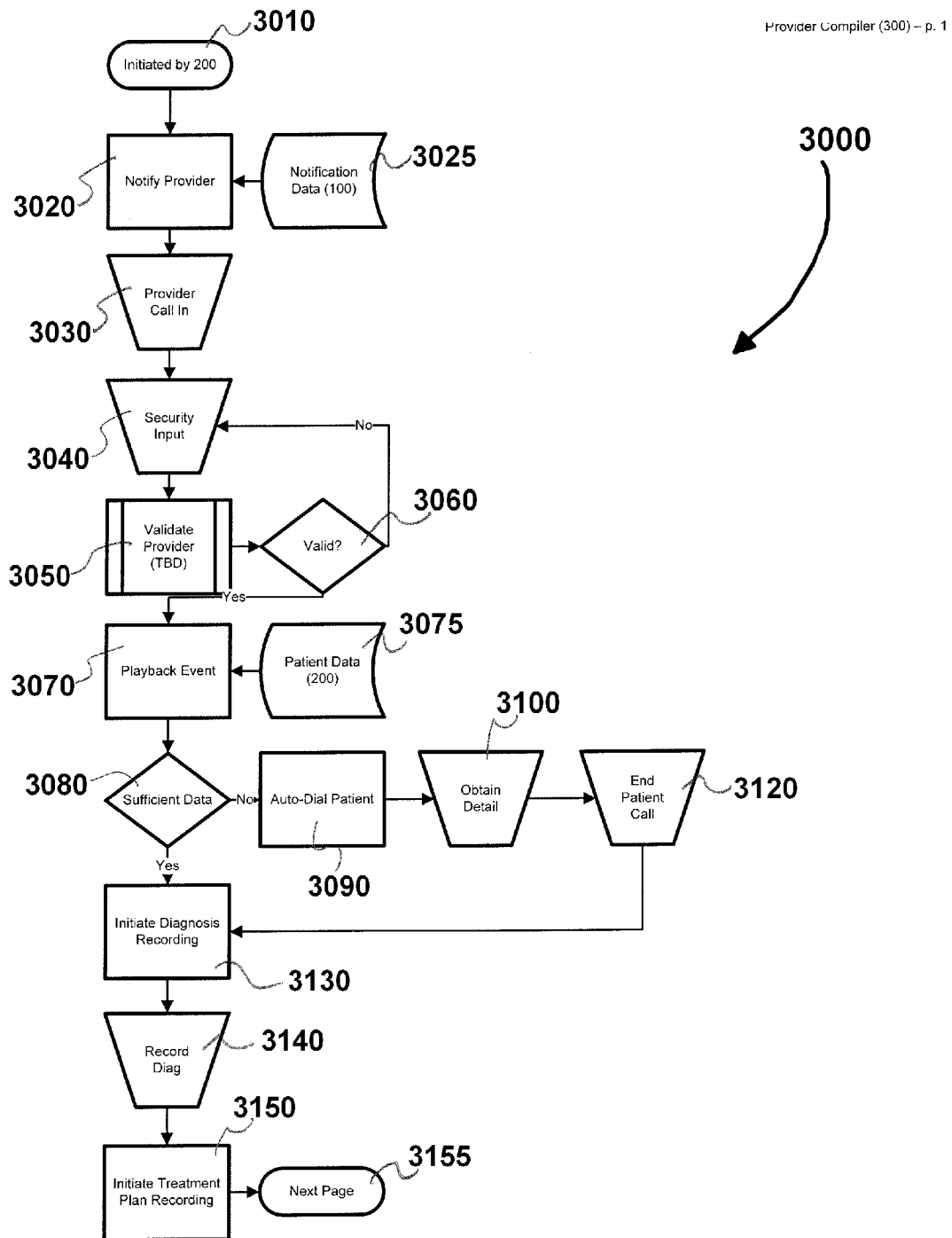
FIGS. 3A, 3B, and 3C are a flow chart of the provider compiler portion of the method and apparatus.
Figure 3B:
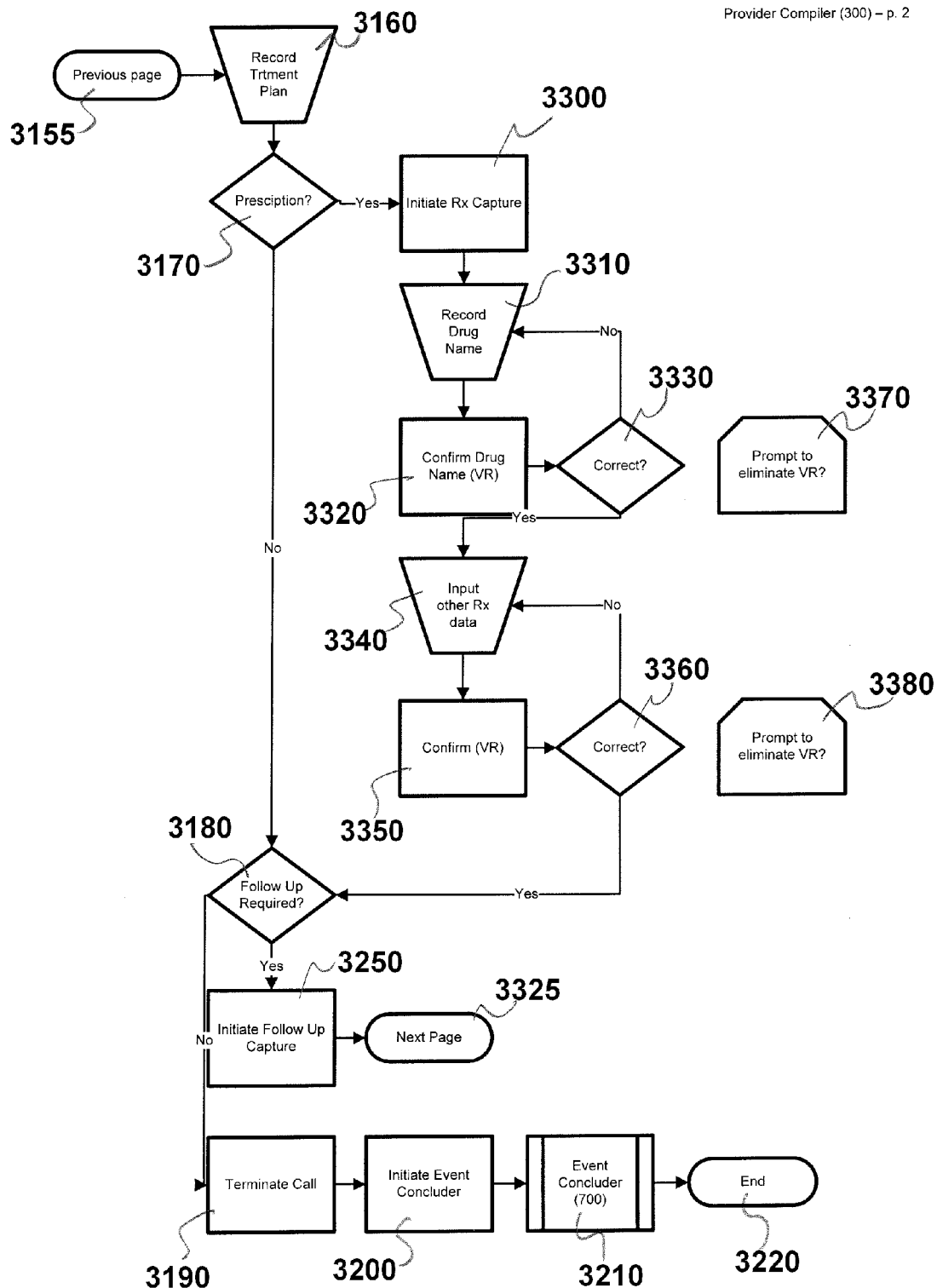
Figure 3C:
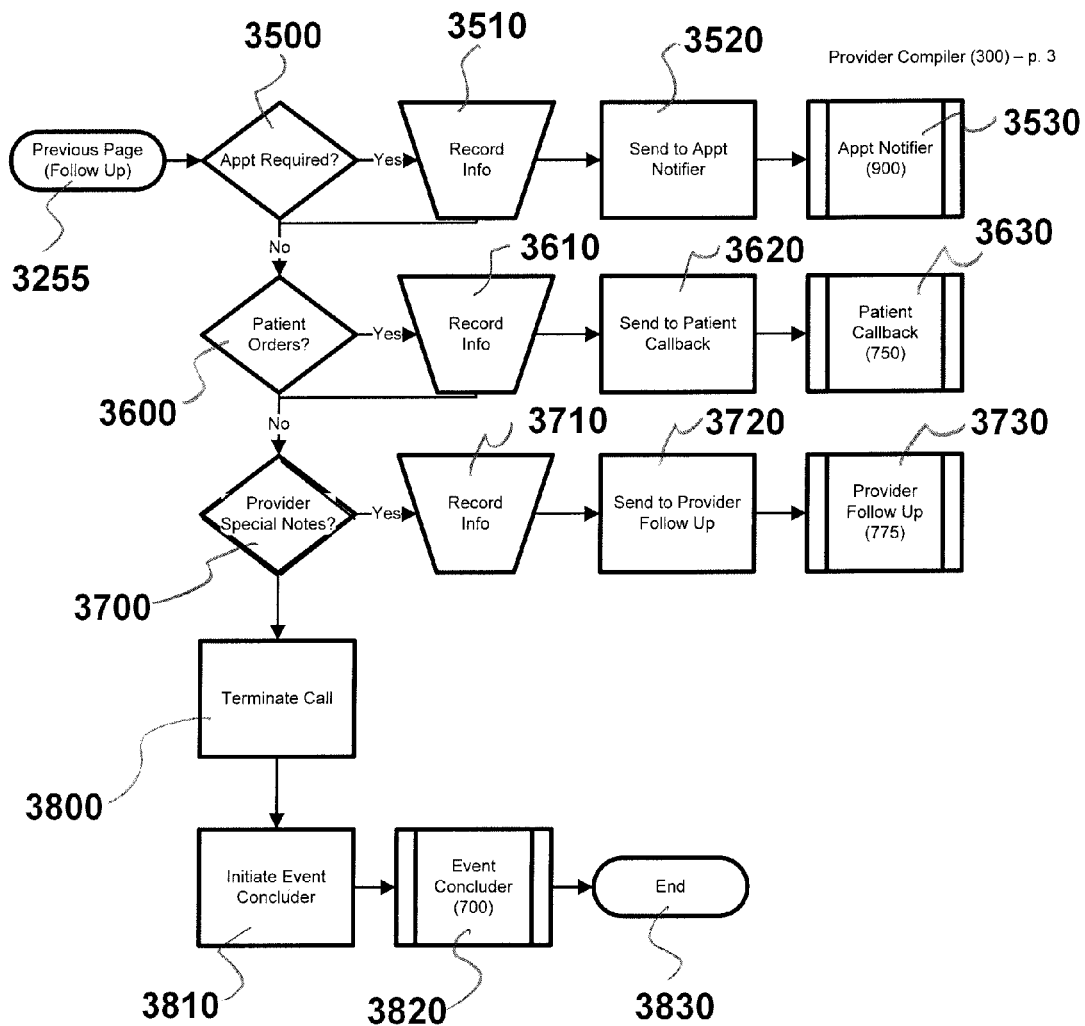

FIGS. 3A, 3B, and 3C are a flow chart 3000 of the provider compiler (300) portion of the method and apparatus 10.

Step 3010 is initiated by the patient compiler 200. In step 3020 a health care provider is notified of the compiled event. Step 3025 indicates that various notification data (established in health care provider defined process 100) can be included in this notification to the health care provider. In one embodiment the health care provider can customize the type and amount of information which will be included in this notification.

After receiving the notification of step 3020, the health care provider in step 3030 accesses the method and apparatus 10, such as by calling in. Steps 3040, 3050, and 3060 provide a method of validating access by the health care provider. Step 3040 requires a security input from the health care provider. For example, a user identification and password may be required. As another example, the notification in step 3020 may include a unique event number which can allow access by the health care provider. Step 3050 validates the input of the health care provider and if validation cannot be made step 3060 sends the process back to step 3040 for new security input. If validation is made, step 3060 moves to step 3070.

In step 3070 the health care provider has access to information which was captured by the patient compiler. Step 3075 indicates that information on patient data (200) is provided. This information can be provided in the form of oral messages, multimedia (such as text, graphics, and oral), or other forms of information.

In step 3080 the health care provider decides whether he has enough information to proceed with a diagnoses and/or treatment plan. If the health care provider decides that not enough information is provided he can contact the individual seeking indirect medical consultation. In step 3090 the method and apparatus 10 can auto dial the individual seeking indirect medical consultation. In step 3100 the health care provider can obtain additional information/detail on information from the person seeking indirect medical consultation and/or patient. In one embodiment this additional information is also recorded by the method and apparatus 10 for compilation as part of the medical record of the indirect medical consultation. In step 3120 this contact (e.g., telephone call) seeking additional information by the health care provider is ended.

In step 3130 the health care provider can make a diagnosis and capture this diagnosis with the method and apparatus 10. In step 3140 the diagnosis is recorded by the method and apparatus 10.

In step 3150 the health care provider can initiate a treatment plan. In step 3160 the treatment plan can be captured by the method and apparatus 10, such as by recordation.

In step 3170 the health care provider has the option of issuing a prescription. If the health care provider decides to issue prescription, next in step 3300 the method and apparatus enters a mode where the prescription is captured. The prescription can be captured through a database of prescription drugs available to the health care provider and accessible to the method and apparatus 10. Voice recognition technology can be used to capture the prescription.

In step 3310 the health care provider provides the name of the prescription drug to be prescribed and the method and apparatus 10 captures this name. The name can be orally provided and voice recognition technology used to capture this name by comparing the name to database of prescription drugs available to the health care provider and accessible to the method and apparatus 10. The database can include identifying items for the prescription drugs such as the N-D-C number, drug descriptions, manufacturers, images, etc. so that the health care provider can be sure that the proper drug is selected. Step 3320 requires that the health care provider confirm the name of the prescription drug. If not confirmed step 3310 is repeated. If confirmed step 3340 is next. One example of confirmation is the name of the drug selected from the database by voice recognition technology is orally played for the health care provider. In other embodiments additional information from the database can also be orally provided to the health care provider for this confirmation. In other embodiments the health care provider has access to an electronic portal (such as the internet) which can display images, text and other information for confirmation of the proper prescribed drug. In one embodiment, beyond the proper prescribed drug name, other information related to the prescribed drug such as dosage and type (which can be obtained from the N-D-C number) is also confirmed with the health care provider. In one embodiment the health care provider is given the option of prescribing the drug through use of the N-D-C number. In step 3370 the health care provider is provided the option of not using voice recognition technology for confirming the prescription drug.

In step 3340 additional prescription information is supplied by the health care provider and captured by the method and apparatus. Step 3350 requires that the health care provider confirm the additional prescription information related to the prescription drug. If not confirmed step 3340 is repeated. If confirmed step 3180 is next. In step 3380 the health care provider is provided the option of not using voice recognition technology for confirming the prescription drug. In one embodiment the method and apparatus 10 has a maximum number of attempts to validate, check one or more of the selections from the user before the selection is merely recorded without validation. In one embodiment the maximum number of times are 2, 3, 4, 5, 6, 7, 8, 9, or 10 times. In one embodiment the health care provider can customize the maximum number of selections.

In step 3180 the health care provider is provided the option of determining whether follow up to the treatment plan and/or prescription is desired. If follow up is selected, next in step 3250 the method and apparatus 10 moves to the mode of capturing initial follow up and step 3500. If follow up is not selected, next in step 3190 the method and apparatus terminates contact with the health care provider (such as by terminating the call), and proceeds to step 3200 where the event concluder (700) is initiated. After initiating the event concluder (700), the provider compiler (300) is ended in step 3220.

Where the health care provider selects to initiate follow up care, in step 3500 the method and apparatus 10 provides the provider with the option of selecting a follow up appointment. If a follow up appoint is selected, the health care provider in step 3510 records an appointment message for the person seeking indirect medical consultation. In step 3520 an appointment notification is sent to the appointment notifier (900). Additionally, the method and apparatus moves to step 3600 where the method and apparatus provides the option for the health care provider to issue patient orders.

If an appointment is not selected by the health care provider, in step 3600 the method and apparatus provides the option for the health care provider to issue patient orders.

In step 3600 the method and apparatus 10 provides the health care provider with the option of issuing customized patient orders. In one embodiment, the health care provider is provided the option of selecting various patient orders which already exist in a database of patient orders. In one embodiment the health care provider is provided the option of customizing a database of possible patient orders. If patient orders are selected, the health care provider in step 3610 issues patient orders, and the method and apparatus 10 can electronically capture/record these patient orders. For example, the method and apparatus can record the oral patient orders of the health care provider. To send these captured patient orders, in step 3620 the patient callback (750) can be initiated. The patient orders are sent to the person seeking indirect medical consultation by the method and apparatus 10. This can be by a return telephone call to the person seeking indirect medical consultation and playing the recorded patient orders. Additionally, the method and apparatus moves to step 3700 where the provider is given the option to issue special notes.

If the health care provider declines to issue special notes, in step 3800 the method and apparatus 10 terminates contact with the health care provider (such as by terminating the call), and proceeds to step 3810 where the event concluder (700) is initiated. After initiating the event concluder (700), the provider compiler (300) is ended in step 3830.

In step 3700 the method and apparatus 10 provides the health care provider with the option of issuing special notes. In one embodiment, the health care provider is provided the option of selecting various special notes in a database of special notes. In one embodiment the health care provider is provided the option of customizing a database of possible special notes. If special notes are selected, the health care provider in step 3710 issues special notes, and the method and apparatus 10 can electronically capture/record these special notes. For example, the method and apparatus can record the oral special notes of the health care provider. To send these captured special notes in step 3720 the provider follow up (775) can be initiated. Additionally, the method and apparatus moves to step 3800 to terminate contact with the health care provider.

Figure 4:
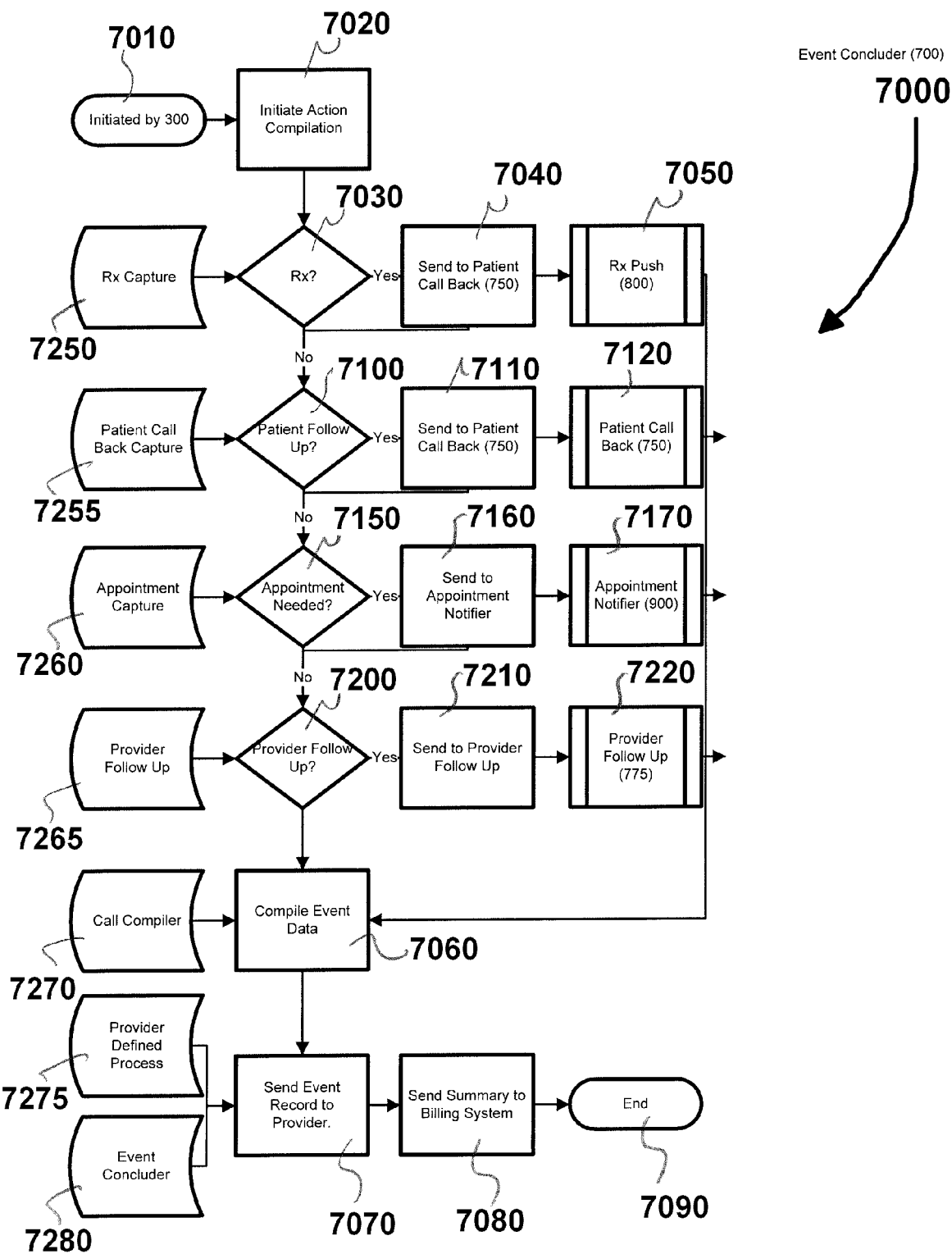
FIG. 4 is a flow chart of the event concluder portion of the method and apparatus.

FIG. 4 is a flow chart 7000 of the event concluder (700) portion of the method and apparatus 10.

Step 7010 indicates that the event concluder (700) is initiated by provider compiler (300). In step 7020 is the initiation of compilation.

If there is no prescription, then the next step is step 7100 to determine if there is a patient follow-up.

If there was a prescription in step 7030, the prescription would have been stored in step 7250. In step 7040 this prescription will be transmitted via the patient call back (750). Step 7050 indicates that the prescription will be sent to the pharmacy via the prescription push. The next step is step 7100 to determine if there is a patient follow-up.

If there is no patient follow up, then the next step is step 7150 to determine if there is a follow-up appointment.

If there was patient follow-up in step 7100, the patient follow-up would have been stored in step 7255. In step 7110 this patient follow-up will be transmitted via the patient call back (750). The next step is step 7150 to determine if there is an appointment to be scheduled.

If there is no appointment to be scheduled, then the next step is step 7200 to determine if there is health care provider follow-up.

If there was an appointment to be scheduled in step 7150, the appointment information would have been captured/stored in step 7260. In step 7160 this appointment information will be sent to the appointment notifier (900) and the appointment notifier activated. The next step is step 7200 to determine if there is health care provider follow-up.

If there is not health care provider follow-up, then the next step is 7060 to compile the data related to the indirect medical consultation event.

If there is follow-up for the health care provider in step 7200, the health care provider follow-up would have been stored in step 7200. In step 7210 this health care provider follow-up will be transmitted via provider follow-up (750). The next step is step 7060 to compile the data related to the indirect medical consultation event.

Step 7270 indicates that the call compiler transmits information for step 7060 in order to compile the data related to the indirect medical consultation event. In step 7070 the compiled information can create a record and transmit this record to the health care provider. In one embodiment the compiled information can include identifying information regarding the indirect consultation event such as patient name, date of event, and/or individualized event indicia. Alternatively, the compiled information can be stored by the method and apparatus and this compiled information accessed by the health care provider at a later point in time.

Steps 7275 and 7280 indicate that the health care provider can customize the manner and type of information which is sent to the provider by the method and apparatus 10 from the event concluder (700).

In step 7080 the method and apparatus 10 can prepare and transmit a summary of the indirect medical consultation event, such as a billing summary. Alternatively, this can be stored for future access by the health care provider. This summary can be sent to the health care provider, or to another entity specified by the health care provider (such as an insurance company).

Step 7090 ends the event concluder (700).

Figure 5:
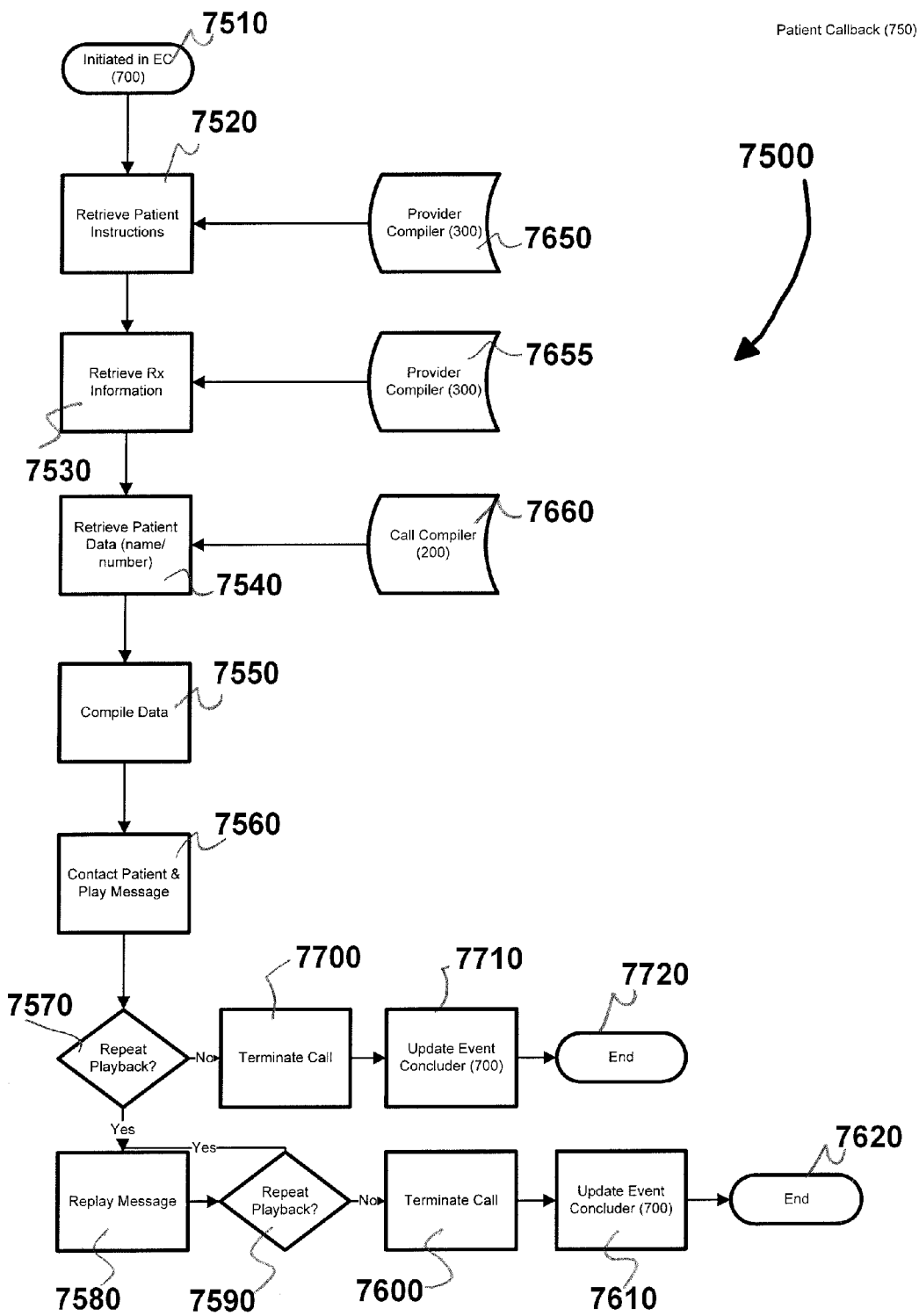
FIG. 5 is a flow chart of the patient call back portion of the method and apparatus.

FIG. 5 is a flow chart 7500 of the patient call back (750) process of the method and apparatus 10. In step 7510 the patient call back (750) process is initiated by the event compiler (700) process.

In step 7520 patient instructions are retrieved. Step 7650 indicates that the provider compiler (300) portion supplies the information for retrieving patient instructions.

In step 7530 prescription information is retrieved. Step 7655 indicates that the provider compiler (300) portion supplies the information for retrieving patient instructions.

In step 7540 patient information is retrieved. Step 7660 indicates that the patient compiler (200) portion supplies the patient data.

In step 7550 the retrieved information/data is compiled for a message/transmission to the person seeking indirect medical consultation. In step 7560, contact is made with the person seeking indirect medical consultation and the compiled information/data is transmitted. For example, a compiled oral message can be played on the phone to the person seeking indirect medical consultation. In another embodiment, an email message can be sent. In another embodiment, a message is transmitted to the person, and the person can retrieve the information/data at a later point.

The following steps will assume that an oral message is played for the person seeking indirect medical consultation. In step 7570 the option is given to playback the oral message. If playback is not selected then step 7700 terminates the call and step 7710 updates the event concluder (700) with the additional information that the patient call back was made. Step 7720 indicates that the patient callback (750) is concluded at this point.

If playback is chosen, in step 7580 the message is replayed, and in step 7590 an additional playback option is provided. If playback is selected, step 7580 is repeated playing back the message again, and step 7590 again provides the option to playback the message. If playback is not selected then step 7600 terminates the call and step 7610 updates the event concluder (700) with the additional information that the patient call back was made. In one embodiment the number of repeat times that the message was replayed can also be updated in the event concluder (700). Step 7620 indicates that the patient callback (750) is concluded at this point.

Figure 6:
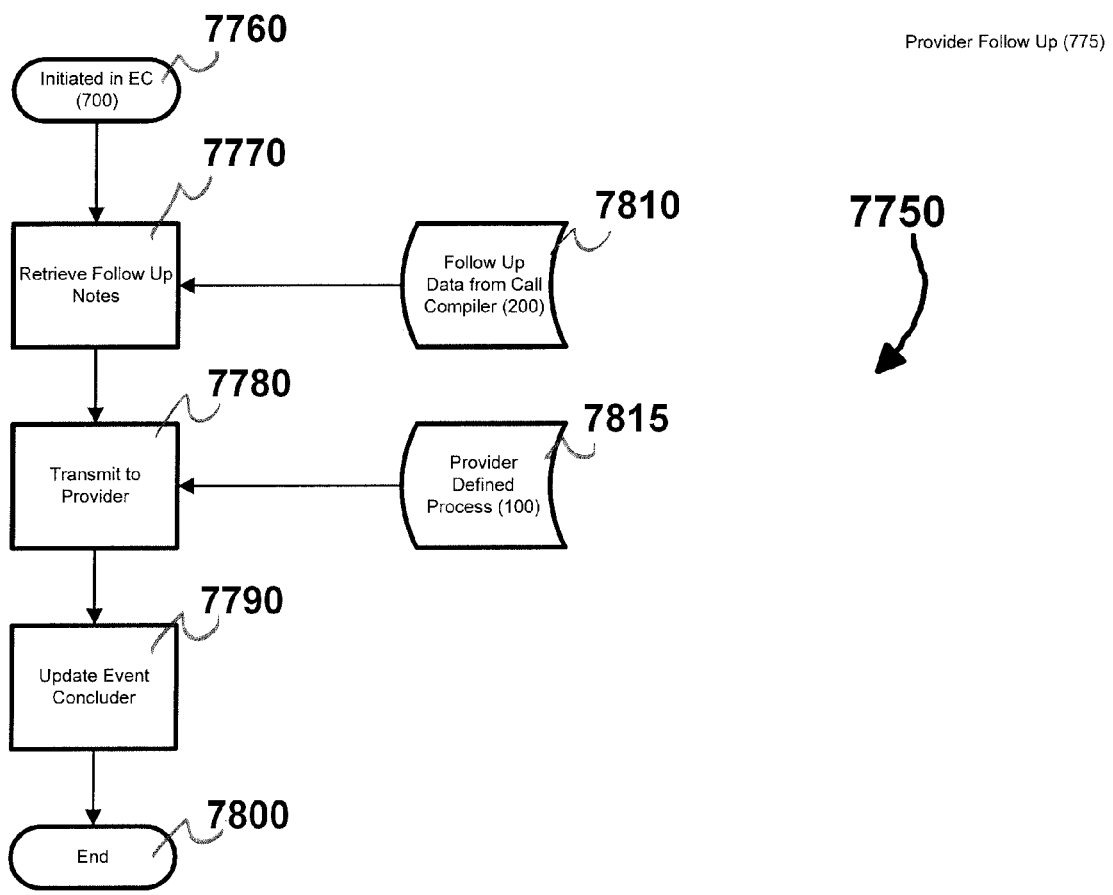
FIG. 6 is a flow chart of the provider follow-up portion of the method and apparatus.

FIG. 6 is a flow chart 7750 of the provider follow-up (775) portion of the method and apparatus 10.

In step 7760 the provider follow-up (775) is initiated by the event concluder (700). In step 7770 health care provider follow up notes are retrieved and/or compiled. These notes can be retrieved in step 7810 from data captured in the provider compiler (300) portion.

In step 7780 the retrieved follow-up notes are transmitted to the health care provider. Step 7815 indicates the option of the health care provider customizing the transmission of the follow-up notes. For example, the health care provider can specify that follow-up notes be sent to a particular place (such as the health care provider's email address, office email, or third party service, and also whether duplicate transmissions should be sent). Additionally, customization can be of the method of transmission, form/content, and type of transmission of the follow-up notes to the health care provider. For example, the follow-up notes can be transmitted in a particular format, such as a pdf file, or word processing file. In one embodiment the follow-up notes are stored by the method and apparatus and the health care provider can later access and/or retrieve same.

In step 7790 the event concluder (700) is updated with the additional information that the follow up notes were transmitted to the health care provider. Step 7800 indicates that the provider follow-up (775) is concluded at this point.

Figure 7:
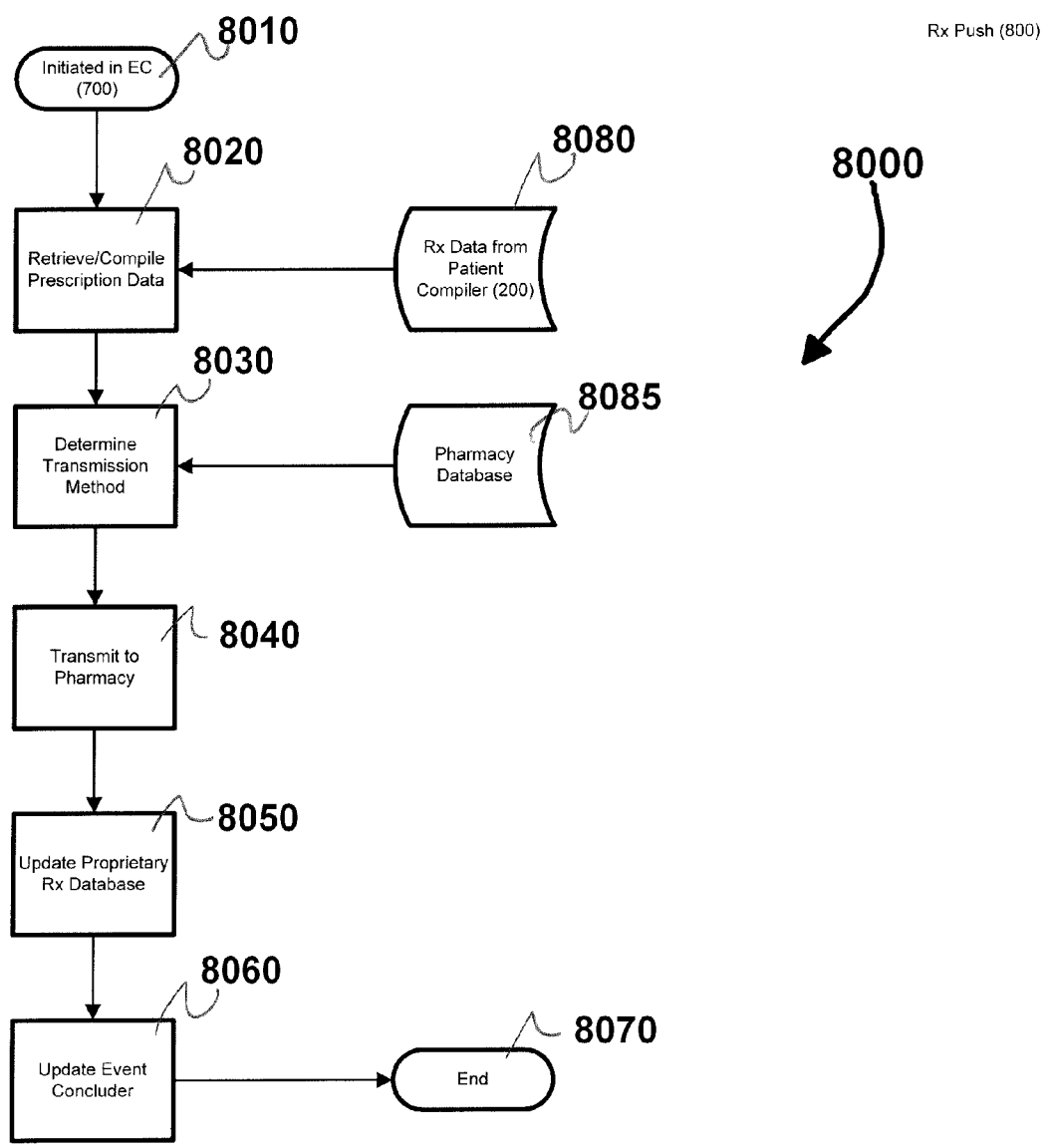
FIG. 7 is a flow chart of the prescription portion of the method and apparatus.

FIG. 7 is a flow chart 8000 of the prescription transmission (800) portion of the method and apparatus 10.

In step 8010 the prescription transmission (800) is initiated by the event concluder (700). In step 8020 prescription information is retrieved and/or compiled. This prescription information can be retrieved in step 8080 from data captured in the provider compiler (300) and/or patient compiler (200) portion.

In step 8030 a transmission method is determined for a pharmacy selected to receive the prescription. In step 8085 information about the selected pharmacy (e.g., location, address, email address, facsimile number, etc.) can be accessed and used for transmitting the prescription to the proper pharmacy. In step 8040 the prescription is transmitted to the selected pharmacy.

In step 8050 a prescription database is updated with information related to the prescription. In one embodiment the database is proprietary to the method and apparatus. In one embodiment the database is proprietary to the health care provider.

In step 8060 the event concluder (700) is updated with the additional information that the prescription was sent to the selected pharmacy. Step 8070 indicates that the prescription transmission (800) is concluded at this point.

Figure 8:
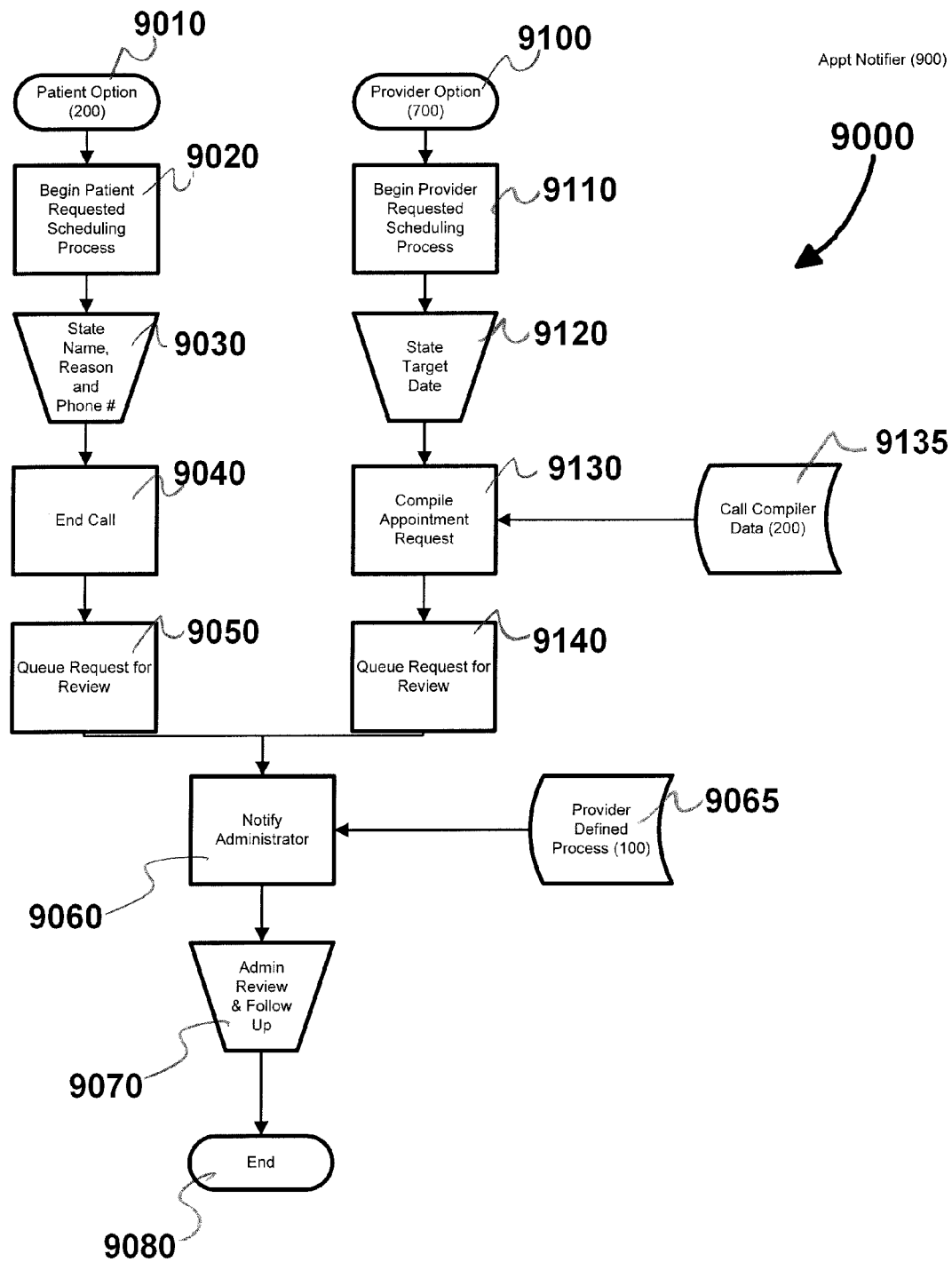
FIG. 8 is a flow chart of the appointment notifier portion of the method and apparatus.

FIG. 8 is a flow chart 9000 of the appointment notifier (900) portion of the method and apparatus 10.

In step 9100 the appointment notifier (900) is activated by the health care provider in step 7150 of flowchart 7000. In step 9110 a request is made for the health care provider to begin follow-up appointment scheduling process. In step 9120 a target date is stated. In step 9130 an appointment request is compiled. Information for this compilation can be obtained in step 9135 from data/information received by the patient compiler (300). In step 9140 a request for review is queued. In step 9060 there is notification of an administrator. Step 9065 indicates that this step can be customized by the health care provider. In step 9070 there is administrative review and follow up regarding the appointment. In step 9080 the appointment process is ended.

In step 9010 the appointment notifier (900) is activated by the patient, such as by a specific request during step 2070 of flowchart 2000. In step 9020 a request is made to begin the patient scheduling process. In step 9030, the name of the patient, reason for appointment, and phone number are provided. In step 9040 the call with the person seeking indirect medical consultation is ended. In step 9050 a request is placed in line or queued for the health care provider to schedule an appoint with the patient. In step 9060 there is notification of an administrator. Step 9065 indicates that this step can be customized by the health care provider. In step 9070 there is administrative review and follow up regarding the appointment. In step 9080 the appointment process is ended.

Figure 9:
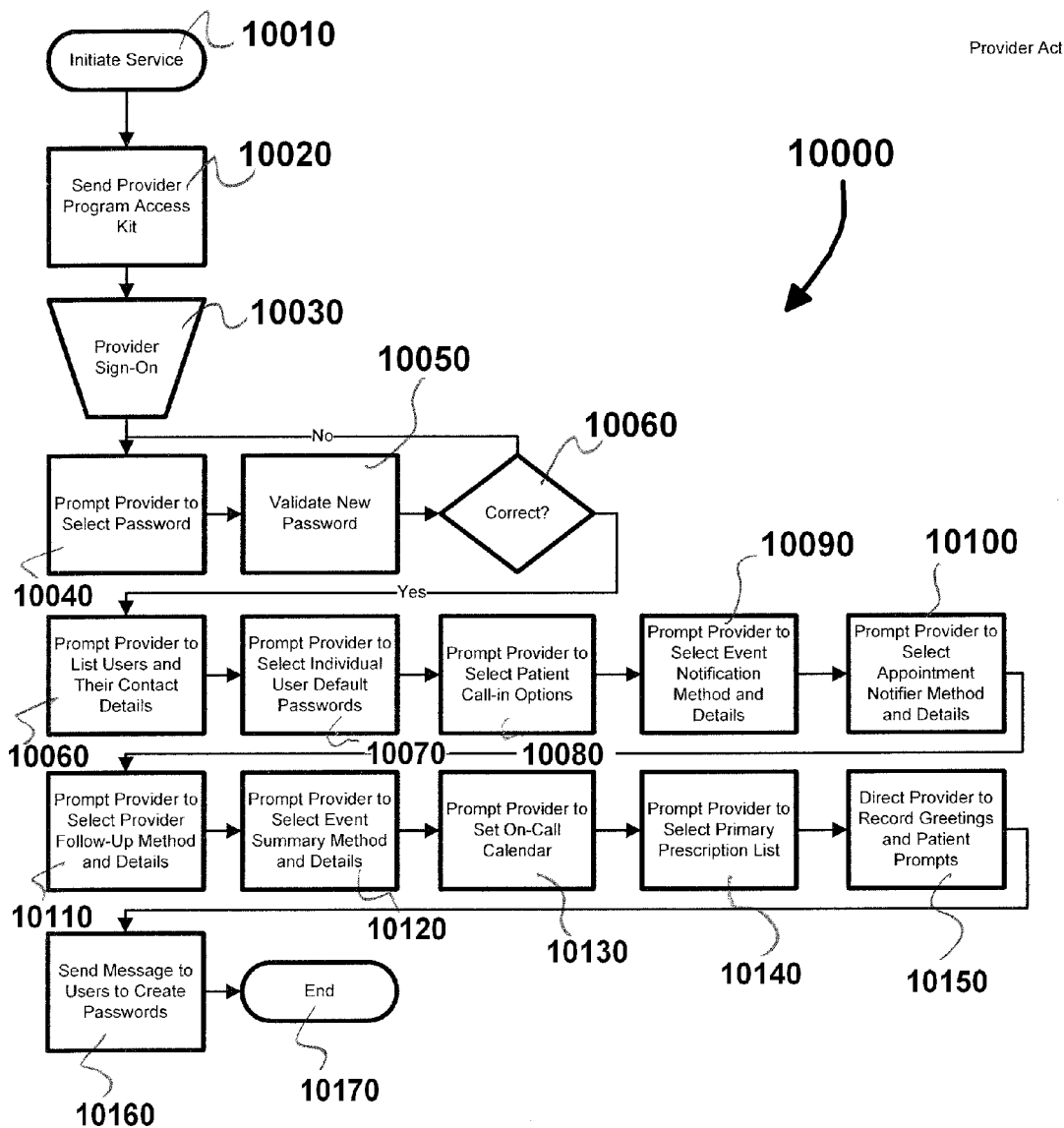
FIG. 9 is a flow chart of the health care provider activation portion of the method and apparatus.

FIG. 9 is a flow chart 10000 of the activation process for a health care provider for the method and apparatus 10.

In step 10010 service is initiated. In step 10020 is sent to the provider a program access kit. In step 10030 the health care provider signs on with the method and apparatus. In step 10040 the health care provider is prompted to select a password. Steps 10050 and 10060 check to validate the selected password.

In step 10060 the health care provider is prompted to list authorized users (authorized on behalf of the health care provider in using the method and apparatus) and their contact details. In step 10070 the provider is prompted to select individual user default passwords. In step 10080 the provider is prompted to select patient call-in options. In step 10090 the provider is prompted to select event notification methods and details provided for notification. In step 10100 the provider is prompted to select appointment notifier methods and details. In step 10110 the provider is prompted to select provider follow-up methods and details. In step 10120 the provider is prompted to select event summary methods and details. In step 10130 the provider is prompted to set "on-call" calendar. In step 10140 the provider is prompted to select a primary prescription list. In step 10150 the provider is directed to record a greeting for persons seeking indirect medical consultation, along with patient prompts for various information to be solicited in the patient compiler (200) portion. In step 10160 is sent a message by the method and apparatus 10 to all users to create individualized passwords. In step 10170 the provider activation portion is ended.

In one embodiment a plurality of information tiers can be provided, and different authorized users can be authorized for different tiers of information access.

The following is one embodiment of steps in seeking indirect medical consultation using a telephone with sample messages and questions.

Phone Consultation:

(1) A patient initiates the telephone consultation by calling into the health care provider's pre-configured telephone answering service. Patients can select from the options configured in "Health Care Provider Activation": (a) Emergency—hang up and dial 911 or go to the emergency room; (b) Urgent—need immediate consultation (see 2); and (c) 12-24 hour follow-up—leave message for callback during business hours.

(2) Upon selecting the option for consultation the patient responds to a series of questions established by the heath care provider. Data is captured in a level of detail that allows it to be parsed for multiple uses throughout the consultation process. Patient is instructed to press "#" key upon completion of each response: (a) Enter last four digits of social security number; (b) State name of caller; (c) State patient name; (d) State patient birth date; (e) State approximate month of last visit; (f) System callback number for patient is ###-###-####, if incorrect press *; (g) If "*", Enter correct 10 digit number; (h) Key in your ten digit phone number; (i) You entered (ten digit number). If this is correct press "#", otherwise press "*"; (j) Cycle steps "h" & "i" (or "f" & "g") until "#" pressed; (k) State your reason for the call; (l) State your preferred pharmacy (voice recognition can be used, unless opted out by caller); (m) State pharmacy city (voice recognition can be used, unless opted out by caller); (n) State pharmacy street/ (address) (voice recognition can be used, unless opted out by caller); (o) Would you like to verify all above via playback? If yes press "*", otherwise press "#"; (p) If you are ready to complete your call press "#". If you would like to start over press "*". (Or step patient through each data element for option to change?); (q) Thank you. Your information will now be forwarded to Dr. X (health care provider). You will be contacted at the number you provided.

(3) The system notifies the health care provider on call via the health care provider-selected method (phone, text, email) that a patient event is in queue or waiting to be responded to.

(4) The health care provider phones into the service using a secure sign-on process: (a) Dials in using phone number established for office; (b) Enters unique health care provider identification number (for individual identification in multi-health care provider office); (c) Enters user defined password.

(5) The system plays the compiled message for the health care provider.

(6) If the health care provider has enough information to diagnose the reported problem, the diagnosis is recorded: (a) If no additional information needed press "#", otherwise press "*"; (b) If "*", system notifies health care provider that patient is being called and tells health care provider to press "#" at end of discussion with patient; (c) System calls patient at number provided and begins recording; (d) Upon completion of gathering additional information health care provider presses "#"; (e) To record diagnosis press "#"; (f) heath care provider states diagnosis and presses"#"

(7) System prompts health care provider to begin treatment plan recording: (a) State treatment plan; (b) If prescription required press "*", otherwise press "#"; (c) If a prescription is required (i) Health care provider states the drug name and the system checks it against a predefined database for that health care provider using voice recognition software and verifies what it heard with the health care provider, (ii) The remainder of the prescription data is gathered; (d) If follow-up (appointment scheduling, patient orders, health care provider reminders) is required press "*", otherwise press "#"; and (e) Any additional information that is relevant is recorded.

(8) Upon completing the diagnosis and treatment plan the health care provider hangs up.

(9) The system then transmits the prescription to the patient selected pharmacy electronically.

(10) The patient is notified by recording that the prescription was sent and of any relevant follow-up treatment steps. For example, the method and apparatus can contact the patient by telephoning the telephone number captured when the initiating call came in.

(11) The health care provider is notified of any treatment follow-up required. This notification can be sent by the method and apparatus to the address and in the manner specified by the health care provider through a health care provider activation option and/or directives (which can be selectively modified by the health care provider as deemed necessary).

(12) The health care provider's administrative staff is notified of any appointment required. See step (11).

(13) The entire recorded event is captured as a wave file (or "WMV" file) and sent to the health care provider for record retention and billing. See step (11).

Health Care Provider Activation:

The following is a list of steps which can be used by a health care provider for signing on or activating the method and apparatus 10: (1) Health care provider (e.g., doctor/ clinic) is provided with a unique user identification and password to access method and apparatus; (2) User signs on to website using the provided information; (3) User is prompted to create a unique password to continue; (4) User is then instructed to set up sub accounts based on number of health care providers at office/clinic; (5) User selects phone number to be used (800 or local number); (6) User selects initial hours of application use; (7) User selects patient event notification method (email, text, page, call); (8) User selects top 100 drugs prescribed (for use with voice recognition set up); and (9) User inputs appropriate numbers/email accounts for follow up notification, appointment scheduling, and delivery of recorded event.

ALTERNATIVE EMBODIMENT

The following provides an alternative embodiment.

"Process flow" means the flow of information through the method and apparatus.

"Data management" means the use of data: both metadata that the method and apparatus consumes during its course of operation, and data it collects as it manages encounters.

"Encounter" means an instance when a person, either a patient or a medical professional, telephones the method and apparatus to consult with a health care provider.

"Event" An encounter is comprised of one or more events. There are four basic types of events: (1) Person calling into method and apparatus; (2) Health care provider reviewing the encounter; (3) Method and apparatus forwarding a prescription to a pharmacy; and (4) Method and apparatus replying to patient.

"Task". An event is comprised of one or more tasks that must be executed. For example, the event of a health care provider review of an encounter with a patient is comprised of tasks that present the patient's recordings to the patient, the health care provider dictating one or more notes, possibly the health care provider telephoning the patient, and possibly the health care provider dictating a prescription.

"Broken Event." An event is "broken" if one or more tasks could not be completed. For example, a health care provider's cell connection may break while he is reviewing a call from a patient; this breaks the health care provider-review event. The method and apparatus notes the task at which the event broke, and uses that information to help the appropriate person complete the event.

"Fulfillment." An event is fulfilled when all of its tasks are completed. An encounter is fulfilled when all of its events are completed.

"Dead Calls." These are telephone calls that are not associated with any event. In most instances, these are calls in which the caller did not enter enough information to perform any positive action. Dead calls must be analyzed by method and apparatus administrators, to attempt to find patterns in them and, if possible, make the method and apparatus more robust.

A Call Is Received: Encounter Initiated

When a patient picks up the telephone and dials a telephone number linked to the method and apparatus, he initiates an encounter with the method and apparatus.

In one embodiment, after receiving the telephone call, the method and apparatus performs the following tasks: (1) Looks up the telephone number in the database to find the health care provider and practice associated with that number; and (2) Retrieves data that describe that health care provider and practice.

In one embodiment, the method and apparatus next does the following:

1. Plays a greeting that identifies the health care provider and practice.

2. Plays a message that instructs the caller to dial 911 if he is calling with a medical emergency.

3. If the telephone number is associated with multiple health care providers, the caller is prompted to choose the health care provider with whom he wishes to interact.

4. Asks the caller to select the type of caller from a set of types:

(a) Health care provider call to review messages.

(b) Medical professional calling to consult with the health care provider.

(c) A patient who wishes to make an appointment to see the health care provider.

(d) A patient who wishes to consult with the health care provider.

(e) An administrator who wishes to "ping" the health care provider. (This is usually done to notify a health care provider that he is on call with the method and apparatus).

5A. If the call is from the health care provider himself, the method and apparatus walks him/her through reviewed all queued encounters. This is described in detail in the following section.

5B. If the call is from a medical professional, the method and apparatus invites the caller to record his/her name, record a message, and enter a telephone number at which he can be contacted. The method and apparatus queues the message for the health care provider to review when he next dials into the method and apparatus.

5C. In one embodiment if the call is from a patient who is seeking an appointment, the method and apparatus plays an informational message, then terminates the call. In other embodiments the patient can be connected to a manual or automated appointment scheduling system.

5D. If the call is from a patient who wishes to consult with a health care provider, and the encounter is a new one, the method and apparatus takes the patient's information. The method and apparatus opens an encounter for the health care provider to fulfill, and spools the information and recordings left by the caller for review by the health care provider.

5E. If the call is from an administrator who wishes to "ping" the health care provider, the method and apparatus sends the health care provider a message to notify him/her that he is on call with the method and apparatus, then terminates the call.

6. Detailed Steps in Patient Consultation. If the caller is a patient who wishes to consult with a health care provider, the method and apparatus asks the caller for information about himself, then uses that information to attempt to identify the caller in the patient-profile data that it maintains.

If the method and apparatus can positively identify the caller, it checks whether that caller has an open encounter with that practice—that is, an encounter that the patient had telephoned earlier, and has not yet been reviewed by the health care provider.

If the caller has an open encounter with the health care provider, the method and apparatus asks the caller if he wishes to add an addendum to what was recorded for the earlier encounter. If the caller responds positively, the method and apparatus records the caller's addendum. However, if the caller responds positively, the method and apparatus informs the patient of the status of that encounter. In either case, the method and apparatus then terminates the call.

If the caller does not have an open encounter, or if the method and apparatus cannot positively identify the caller, then the method and apparatus opens a new encounter for the caller. When the method and apparatus opens an encounter, it inserts a record into the database to describe that encounter. In the course of fulfilling the encounter, the method and apparatus will link to that record all of the records of actions it took, such as recordings it made or telephone calls it dialed. It also informs the health care provider review manager that a new encounter has been spooled for the health care provider to fulfill. The health care provider review manager, in turn, informs the health care provider notification manager of the new encounter, so that manager can start the process of informing the health care provider that an encounter is awaiting his/her review.

When the method and apparatus's actions fulfill the encounter, the encounter is closed. The method and apparatus updates the record of the encounter to mark the encounter as closed, and removes it from the health care provider's review queues, and from his/her notification queue.

The Health Care Provider Responds: Encounters Fulfilled

When the health care provider dials into the method and apparatus to review his encounters, the method and apparatus finds all open encounters that are waiting in line for that health care provider, and presents them to the health care provider for review.

1. In one embodiment the method and apparatus manages two queues of encounters: one for calls from medical professionals, and the other for calls from patients: (a) If neither queue contains any encounters, the method and apparatus states so, then terminates the call; (b) If only one queue contains encounters, the method and apparatus presents that queue to the health care provider; and (c) If both queues contain encounters, then the method and apparatus asks the health care provider to choose the queue he wishes to review first.

2. Once a queue is chosen, the method and apparatus presents that queue's encounters to the health care provider, one after another, in the order in which they were received. The health care provider then responds to the encounter.

(a) In the case of an encounter with a medical professional, the health care provider may choose to telephone the professional at the call-back number he entered; or the health care provider may choose to close he encounter without telephoning (for example, if the health care provider has already spoken with the professional and has no need to speak with him/her again).

(b) In the case of an encounter with a patient, the health care provider has the option of entries for the medical record, instructions to appointment personnel, and prescriptions for the patient. If the health care provider needs to speak with the patient, he/she can instruct the method and apparatus to telephone the patient at the number the patient entered.

3. When the health care provider indicates that he has finished responding to the encounter, the method and apparatus attaches to the encounter the items of information that it collected from the health care provider, both recordings and text gleaned via voice recognition.

4. The method and apparatus then asks the health care provider to confirm that the encounter is closed. Once the health care provider has done that, the method and apparatus records that the health care provider has responded to the encounter. Finally, the method and apparatus removes the encounter from the appropriate review queue and the notification queue, and spools the events that will fulfill the health care provider's instructions.

Reporting: "Closing the Loop"

In one embodiment reports return information to administrators, health care providers, and practice personnel. The reports "close the loop" on the encounter, by ensuring that health care providers and administrators know what was done, and when it happened.

In one embodiment reports can be delivered via email and can be either HTML, for viewing on the screen; or CSV, for loading into a spreadsheet or database.

The following describes some reports that can be used to "close the loop".

1. Reports for Health Care Providers and Practices

The following reports are directed at personnel or health care providers within a practice, to report on individual patient encounters.

(a) Health Care Provider Instruction: Appointment

When a health care provider dictates an instruction for his practice's appointment personnel, the method and apparatus can executes a report that attempts to identify the patient. It then assembles an email that includes the information about the patient plus a copy of the recording the health care provider dictated it, encrypts it, and emails it to the email address that the practice's appointments clerk.

The method and apparatus records the report and the email as actions associated with this encounter.

(b) Health Care Provider Instruction: Medical Notes

When a health care provider dictates an instruction for the patient's medical record, the method and apparatus can execute a report that attempts to identify the patient. It then assembles an email that includes the information about the patient plus a copy of the recording the health care provider dictated it, encrypts it, and emails it to the health care provider's email address The method and apparatus records the report and the email as events associated with this encounter.

(c) Encounter Description Report

For each encounter with a patient, the method and apparatus generates a report that describes the encounter, as follows: (i) Date and time encounter began, (ii) Information that identify patient, (iii) Events associated with encounter: telephone calls received, telephone calls placed, dictations made, prescriptions dictated, prescriptions dispatched, and (iv) Ultimate disposition of encounter.

The method and apparatus assembles an email to hold this report, attached to the report the all recordings associated with the encounter, encrypts it, and dispatches it to the health care provider who provided the service.

(d) Encounter Error Report

If an error occurs during the execution of an encounter that "breaks" the encounter, a report of that event can be generated automatically. The report describes the encounter and the nature of the error. The report is then encrypted and emailed to the health care provider.

(e) Summary of Encounters

Summary reports of patient encounters are generated daily that summarize each encounter begun the previous day. One report can summarize each encounter, as follows: (i) Patient identifier, when available; (ii) Date and time of encounter; (iii) Health care provider handling encounter; (iv) Date and time that health care provider responded to the encounter; (v) Were prescriptions dispatched?; (vi) Errors, if any; and (vii) Ultimate disposition of the encounter.

In one embodiment reports can be assembled for each health care provider, and for each practice. Each report is then encrypted and emailed to the appropriate email address.

2. Reports for Administrators

In one embodiment, the following reports can be generated to assist administrators track activity on the method and apparatus, and to discover and deal with problems: (a) Count of Encounters which can include the number of encounters received, broken down by practice and by health care provider; (b) Counts of Interactions which can include the number of interactions of each type—outbound call, email, text message, electronic message—organized by practice, health care provider, and outcome; (c) Encounter Summary which (can be analogous to the Encounter Summary Report generated for health care providers and practices, except that administrators can view encounters across practices); and (d) Error Report which can summarizes each error that occurred in the requested period of time (analogous to the Error Report generated for health care providers and practices, except that administrators can assemble record across practices. The administrators' version of this report will also include information that is useful to method and apparatus administrators, such as ID of server on which the error occurred).

Data Management

1. Data Storage

The federal government places stringent requirements on the storage of data that contain confidential patient information. In one embodiment to address government requirements one or more of the following can be required: (a) No patient data can be stored in the database maintained by the operational telephony method and apparatus; (b) No indication that a medical consultation was requested or given can appear in the log files written by the operational telephony; (c) data must be written to, and read from, a secured database via a method and apparatus of messages. The "remote" database may, in fact, be in the same physical location as some or all of the voice servers, but it must reside behind a security firewall that meets Health Care Financing Administration (HCFA) standards; (d) Reports are be written by software that resides behind the database security firewall; and (e) Dissemination of reports are made by a secure channel, such as offered by Blue Tie Inc. and similar ISPs.

Data will be exchanged with the database via a method and apparatus of well-defined messages, rather than via ad hoc database queries.

2. Metadata

"Metadata" are the data that the method and apparatus consumes in the course of its operation. The following lists tables of metadata used, and the data elements in each table.

Data may be maintained in a normalized relational database. What follows is a conceptual overview of the tables, rather than a detailed design.

(a) Telephone Numbers

This table holds the telephone numbers that patients can dial to access the method and apparatus. The telephone number dialed will identify the patient and practice that the patient is contacting. This table holds the following data: (i) Ten-digit telephone number, (ii) ID of practice linked to this telephone number, and (iii) ID of health care provider who "owns" this telephone number.

Health care provider and practice are preferably identified separately, because each health care provider may be affiliated with more than one practice, and each practice may have more than one health care provider affiliated with it.

In one embodiment the table assigns an ID to a record. This is an internally generated number that has no significance other than to uniquely identify the record within the database. This ID should not be exported to other information method and apparatuses.

(b) Practices

In one embodiment this table describes each practice that uses the method and apparatus and can hold one or more of the following items of data: (i) Practice ID, (ii) Name, (iii) Street address, (iv) Suite, (v) City, (vi) State, (vii) ZIP code, (viii) Main telephone number, (ix) Name of grammar for voice recognition of practice's health care providers (if available), (x) Name of file that holds recording of practice's greeting, (xi) Name of script for accessing appointment method and apparatus (if available), and (xii) Name of script for accessing medical-record method and apparatus (if available).

(c) Personnel

This table gives the personnel, other than health care providers, who are affiliated with each practice. We assume that a person can be affiliated with one and only one practice. This table will hold one or more of the following items of data: (i) Personnel ID, (ii) Practice for which person works, (iii) First name, (iv) Middle initial, (v) Last name, (vi) Title, (vii) Telephone number, (viii) Email address, (ix) Encryption key, for public-key encryption of mail sent to this person, and (x) Role; e.g., nurse, appointment clerk, medical-record clerk, transcriptionist.

In one embodiment, a cross-reference table can link a practice with key personnel: e.g., the appointment manager, the manager of medical records, and the principal nurse.

(d) Specialties

This table lists medical specialties. It holds at least the Name of the specialty. A cross-reference table links health care providers with specialties. This will help manage the routing of telephone calls to other health care providers of the same specialty within the same practice. It also provide a general framework for identifying a possible drug listing for the health care provider when customizing the method and apparatus for the health care provider. For example, a drug list of 100 common drugs prescribed by pediatricians can be generated and the health provider add or delete from such list to create a customized list of drugs for the heath care provider.

(e) Pharmaceuticals

This table can include commonly prescribed drugs. It holds one or more of the following items of information: (i) US Pharmacopeia identifier, (ii) Proprietary name, (iii) Generic name, (iv) Normal minimum dose, (v) Normal maximum dose, and (vi) Normal regimen (e.g., "BID").

A cross-reference table can link each drug with the specialty that normally prescribes it.

(f) Health Care Providers

This table includes the health care providers using the method and apparatus and can include one or more of the following items of information: (i) Health care provider ID, (ii) First name, (iii) Middle initial, (iv) Last name, (v) Suffix (e.g., "Jr", "III"), (vi) Degree (e.g, "MD", "DO"), (vii) Mailing street address, (viii) Mailing suite number or post-office box, (ix) Mailing city, (x) Mailing state, (xi) Mailing ZIP code, (xii) Name of recording that names the health care provider, if one has been made, (xiii) Principal telephone number, (xiv) Cell phone number, (xv) Email address, (xvi) PIN for system, and (xvi) ID for electronic prescription service.

A cross-reference table can link each health care provider to each of his specialties. A cross-reference table can link each health care provider to each of his practices.

(g) Health Care Provider Unavailability

In one embodiment there can be an option for the health care provider being unavailable. The health care provider may not be available to handle patient encounters for selected periods of time—say, when the health care provider is on vacation, or is out of town on a conference. This table lists the periods when the health care provider will not be available, and identifies the health care provider who will cover for him. It can contain one or more of the following items of information: (i) Health care provider ID, (ii) Date/time the period of unavailability begins, (iii) Date/time the period of unavailability ends, and (iv) The identifier of the health care provider who will cover for this health care provider.

Encounters initiated during a period of unavailability can be queued or the health care provider who is covering for the unavailable health care provider. Likewise, encounters that opened before the period of unavailability but which are not yet closed will be routed to the covering health care provider. For example, if a pharmacist has a question about a prescription the health care provider wrote, but telephones the health care provider at a time when he is unavailable, the pharmacist will be routed to the health care provider who is covering for that health care provider.

The health care provider will be able to queue an indefinite number of periods of unavailability in the future.

(h) Pharmacy Chains

This table describes the major chains of pharmacies. Please note that there is minimum requirement for defining a chain of pharmacies: an independent pharmacy can, if necessary, be described as a chain of one. This table can contain one or more of the following items of information: (i) National Council for Prescription Drug Programs (NCPDP) identifier, (ii) Name, (iii) Corporate telephone number, and (iv) Script for navigating voice-mail method and apparatus.

(i) Pharmacies

This table describes pharmacies. It can contain one or more of the following information: (i) NCPDP identifier, (ii) Chain affiliation, if any, (iii) Voice telephone number, (iv) Voice-mail telephone number, (v) Voice-mail extension or mailbox number, (vi) Email address, (vii) Name, (viii) Street address, (ix) Suite, (x) City, (xi) State, (xii) ZIP code, (xiii) Vertical coordinate of locale (derived from ZIP code), (xiv) Horizontal coordinate of locale (derived from ZIP code), (xv) Opening time (one entry for each day of the week), and (xvi) Closing time (one entry for each day of the week), (j) ZIP Codes This table can include every ZIP code in the United States. It has at least the following information: (i) ZIP code, (ii) State in which it is located, (iii) Time zone in which it is located, (iv) Whether daylight savings time applies in that locale, (v) Vertical coordinate of center point of zone, (vi) Horizontal coordinate of center point of zone.

(k) USPS Locales

This table holds the locale identifiers used by the Postal Services. For the United States this table contains at least the following information: (i) USPS ID, (ii) Name, (iii) Type (e.g., city, military base, Indian reservation), (iv) State, (v) Time zone, (vi) Whether daylight savings time applies in that locale, (vii) Vertical coordinate of center point of zone (derived from ZIP codes), and (viii) Horizontal coordinate of center point of zone (derived from ZIP codes). A cross-reference table links each locale with the ZIP codes that it overlaps.

(l) Reports

This table names and describes reports that the method and apparatus can generate. It can contain one or more of the following items information: (i) ID of report, (ii) Name, (iii) Description, and (iv) File of code that generates report.

(m) Dictionary

The dictionary table defines symbols used throughout the database. It can be structured as follows: (i) Symbol being interpreted, (ii) Class of the symbol, (iii) Interpretation, suitable for use in reports, and (iv) Description of symbol, suitable for documentation The "class" of symbols organizes the symbols by types. For example, encounter outcomes are a class of symbols; likewise, types of recordings are defined by another class of symbols. The first class of symbols to be defined will be the class that defines the classes of symbols themselves. The dictionary table will be used principally by the method and apparatus's reports, but it will also be used to document the database itself. Also, by forcing method and apparatus programmers to use only a predefined set of symbols, it helps to keep the method and apparatus under control.

Data Collected From Patient Encounters

During the course of its operation, the method and apparatus collects information about patient encounters. The following describes these data, and the tables that hold them.

(a) Patient Profile

This table holds one record for each patient who has used the Method and Apparatus™ method and apparatus. This table is a hybrid: it holds data gathered during a patient encounter, but it can also hold data collected from an external source. It can contain one or more of the following items of information: (i) ID of most recent encounter, (ii) Most recently entered contact telephone number, (iii) Most recently entered ZIP code (if any), (iv) Most recently used USPS location ID (if any), (v) Most recently recited state, (vi) Most recently recited city, and (vii) Most recently selected pharmacy.

This table may also contain information required by the electronic prescription service system. These data will not have been gathered during the interaction with the patient; rather, it will have been retrieved from an outside source, most likely a practice's medical-record method and apparatus, either interactively or in batch form (to "seed" this table). These data include the following: (i) First name, (ii) Middle initial, (iii) Last name, (iv) Date of birth, (v) Social Security number, and (vi) Gender.

A cross-reference table links this patient to each unique combination of health care provider and practice with whom he has had an encounter via the method and apparatus. This cross-reference table will also give the patient's ID number for this practice, if known.

(b) Encounters

This table describes encounters with the patient and can include: (i) Encounter ID (generated by the method and apparatus), (ii) Practice ID, (iii) ID of health care provider selected, (iv) ID of health care provider handling encounter, (v) Encounter type: medical professional, or patient, (vi) Contact telephone number, (vii) Date and time encounter began, (viii) Date and time encounter ended, (ix) Status of encounter: open, closed, or reopened, and (x) State (if encounter is open, task awaiting performance; if closed, the encounter's disposition).

If the encounter is from a patient, a cross-reference table links this table to the patient.

(c) Events

This table records events executed to fulfill an encounter. It also holds records of pending events—events (or rather, the next event) that must be executed in the process of fulfilling the encounter. This table can contain at least the following information: (I) First name, (ii) Encounter ID, (iii) Event ID (generated by the method and apparatus), (iv) Event type (call from health care provider, call to patient, submission of prescription), (v) Event status: open, closed, (vi) Date/time event submitted, (vii) Date/time event last attempted, (viii) Date/time event fulfilled, and (ix) Outcome of attempt at fulfillment: success, failure.

The various "manager" modules read this table to look for events that they need to execute. This table also gives a running log of the fulfillment of an encounter.

Events can be locked while they are being executed, to ensure that they are not accidentally executed more than once.

(d) Prescriptions

This table lists the prescriptions written as part of a patient encounter. It contains one or more of the following items information: (i) ID of event, (ii) ID of recording that gives the prescription, (iii) Drug prescribed (if identified via voice recognition), (iv) Dosage prescribed (if recognized via voice recognition), (v) Regimen prescribed (if recognized via voice recognition), (vi) Date and time delivery was initiated, and (vii) Date and time delivery was completed.

A cross-reference table will link the prescription to the method or methods used to deliver it. More than one method may be used in the case of failure.

(e) Telephone Calls

Each telephone call is recorded here. This table contains one or more of the following items of information: (I) Call ID, as set by the method and apparatus, (ii) Call ID, as set by the telephony provider, (iii) Telephone number to which call was dialed, (iv) Telephone number from which call was dialed, (v) Date and time call initiated, (vi) Date and time call ended, (vii) Direction of call: inbound or outbound, (viii) Event ID, (ix) Type of call (for example, patient to method and apparatus; medical professional to method and apparatus; health care provider to method and apparatus; method and apparatus to patient; or method and apparatus to pharmacy voice mail), (x) Telephony outcome of call (for example, call answered by human, busy, no answer, operator intercept, or voice mail), and (xi) Business outcome of call: success, failure.

Not every telephone call is associated with an event. For example, if a person calls the method and apparatus, asks to consult with a health care provider, then hangs up before entering any information, that call will not be associated with any encounter, and therefore will not have an event identifier. These are "dead calls".

A given interaction may result in multiple telephone calls being run simultaneously. For example, a health care provider dials into the method and apparatus to listen to his queued encounters; during the course of reviewing one encounter, he instructs the method and apparatus to dial the patient. While the health care provider is talking with the patient, two telephone calls are running simultaneously: one from the health care provider to the method and apparatus, and a second from the method and apparatus to the patient.

(f) Recordings

This table describes recordings made in the course of a telephone call. Each record holds one or more of the following items of information: (I) Recording ID, as set by method and apparatus, (ii)

Recording ID, as set by telephony method and apparatus, (iii) Name of file that holds recording, (iv) Call ID, (v) Encounter ID, (vi) Recording type (e.g., prescription, patient instructions, patient's name), (vii) Status of recording (e.g., available, erased), (viii) Date/time that the recording will expire, (ix) Time that making of the recording started, and (x) Time that making of the recording ended.

(g) Text Messages

This table records text messages sent, usually to notify the health care provider that an encounter awaits his disposition. It contains one or more of following items of data: (i) Message ID, as set by method and apparatus, (ii) Event ID, and (iii) Date/time message sent.

(h) Electronic Messages Sent/Received

This table record the electronic messages that the Method and apparatus method and apparatus has sent and received to the electronic prescription service system in the course of executing a prescription. It contains one or more of the following items of information: (i) Prescription ID, (ii) Date/time encounter sent/received, (iii) Type of message, as defined by the electronic prescription service system, (iv) Body of message, and (v) Outcome of message transmission.

A cross-reference table will link each electronic message with the prescription that it is helping to fulfill.

(i) Reports Generated

This table records each report generated by the method and apparatus. It holds one or more of the following items of information: (i) Encounter ID, (ii) Type of report, (iii) Date and time generated, (iv) Method by which output of report was delivered (e.g., FTP, web, email), (v) File that holds output of report, and (vi) SQL from which report was generated.

If possible, each report's output should be preserved for some reasonable period of time.

(j) Emails Sent

This table describes the various emails that the Method and apparatus sends.

Maintenance Tasks For Tables

The following describes some tasks that can be performed to maintain these tables. The tables that hold information about encounters need no maintenance, other than what is usual for database administration. However, the tables that hold metadata will need continual update and tuning, because in most cases they hold information imported from outside the method and apparatus. The following list proposes how these tables should be maintained. The rules about who should update a given table is based on the principle of "first, do no harm" for the first pass, at least, the method that offers the fewest opportunities for having a careless mistake damage the method and apparatus should be the one used.

(a) Telephone Numbers

This table will be updated by authorized personnel, using information supplied by practices and health care providers.

(b) Practices

This table will be updated by authorized personnel, using information supplied by practices. Updates will be submitted by practices, then inserted by administrators.

(c) Personnel

This table will be initialized by authorized personnel, using information supplied by practices. After initialization, each practice will be able to use a web interface to maintain information about its personnel.

(d) Health Care Providers

When a practice is added to the method and apparatus, it will submit information about its health care providers to administrators. Administrators will be responsible for initially inserting information about health care providers into the method and apparatus. Once the method and apparatus is initialized, practices and health care providers themselves can maintain the information themselves, for example, via a web interface.

The reason for this division of work is to ensure that a health care provider who is already in the method and apparatus via another practice is handled correctly, and that discrepancies between the information submitted by the practice and the information already in the method and apparatus are resolved properly.

(e) Health Care Provider on Call

Health care providers or office personnel will enter these data via a web interface.

(f) Pharmacy Chains

These will be inserted by administrators, using data received from the electronic prescription service system.

(g) Pharmacies

These will be insert by method and apparatus administrators.

(h) Reports

These will be insert by method and apparatus administrators.

(i) Dictionary

These will be insert by method and apparatus administrators.

Importation Scripts

Importation scripts can read files of data and write them into the method and apparatus database. Scripts can be needed to import data at regular intervals from one or more of the following sources: (i) ZIP code data from a selected commercial source, (ii) Locale information from the US Postal Service, (iii) Information on drugs from the US Pharmacopeia, (iv) Information on specialties, and the drugs prescribed by those specialties, from authoritative sources that are to be identified, and (v) Information on pharmacies and pharmacy chains from the National Council for Prescription Drug Programs.

The following information can be needed to import whenever a new practice is added to the method and apparatus: (i) Information about health care providers and (ii) Information about personnel. Data about patients can also be imported and it can be updated regularly.

Administration Tools

Administration tools can fall into the following categories: (i) Tools to monitor method and apparatus performance, (ii) Tools to maintain the database, and (iii) Tools for resolving errors.

(a) Tools to Monitor Method and Apparatus Performance

Monitoring has been discussed in the section on Administration, above. Briefly, administrators will monitor the method and apparatus to ensure that both the platform and the method and apparatus are working correctly. A variety of tools will be available for this work, both reports and tools to monitor events in real-time.

The reports will be written using the same software as the other reports. Monitoring tools will be prepared using the tools available on the platforms' operating method and apparatus.

(b) Tools to Maintain the Database

Maintaining the database involves updating the contents of tables that hold metadata. Scripts will be prepared to maintain the following tables: (i) Telephone numbers, (ii) Practices, (iii) Practice Preferences, (iv) Personnel, (v) Health care providers, (vi) Health care provider Unavailability, (vii) Reports, and (viii) Dictionary.

Much of the work can be done through a web-based interface. Maintenance of personnel, health care providers, and health care provider availability can be turned over to the practices themselves to maintain; all other tables must be maintained by the method and apparatus administrators.

(c) Tools for Resolving Errors

Each class of error will require its own remedy, and therefore its own tools. Very few of them can be designed a priori. However, errors in call-handling are an exception: often, it will be possible to resolve such an error by creating a new event for a given encounter, then letting the method and apparatus do its work.

For example, if an administrator notices that, for whatever reason, a health care provider has failed to review a given patient contact, he can resolve the problem by generating a "call the health care provider" event for this encounter, which will force the method and apparatus to dial the health care provider and get him/her to review the encounter.

For the pilot method and apparatus, the principal tool for monitoring the method and apparatus will be a set of scripts that comb the database for error conditions and bring them to the attention of a method and apparatus administrator. The administrator will have a book of procedures on what to do in each situation, and that he will follow.

Call Management System

Figure 10:
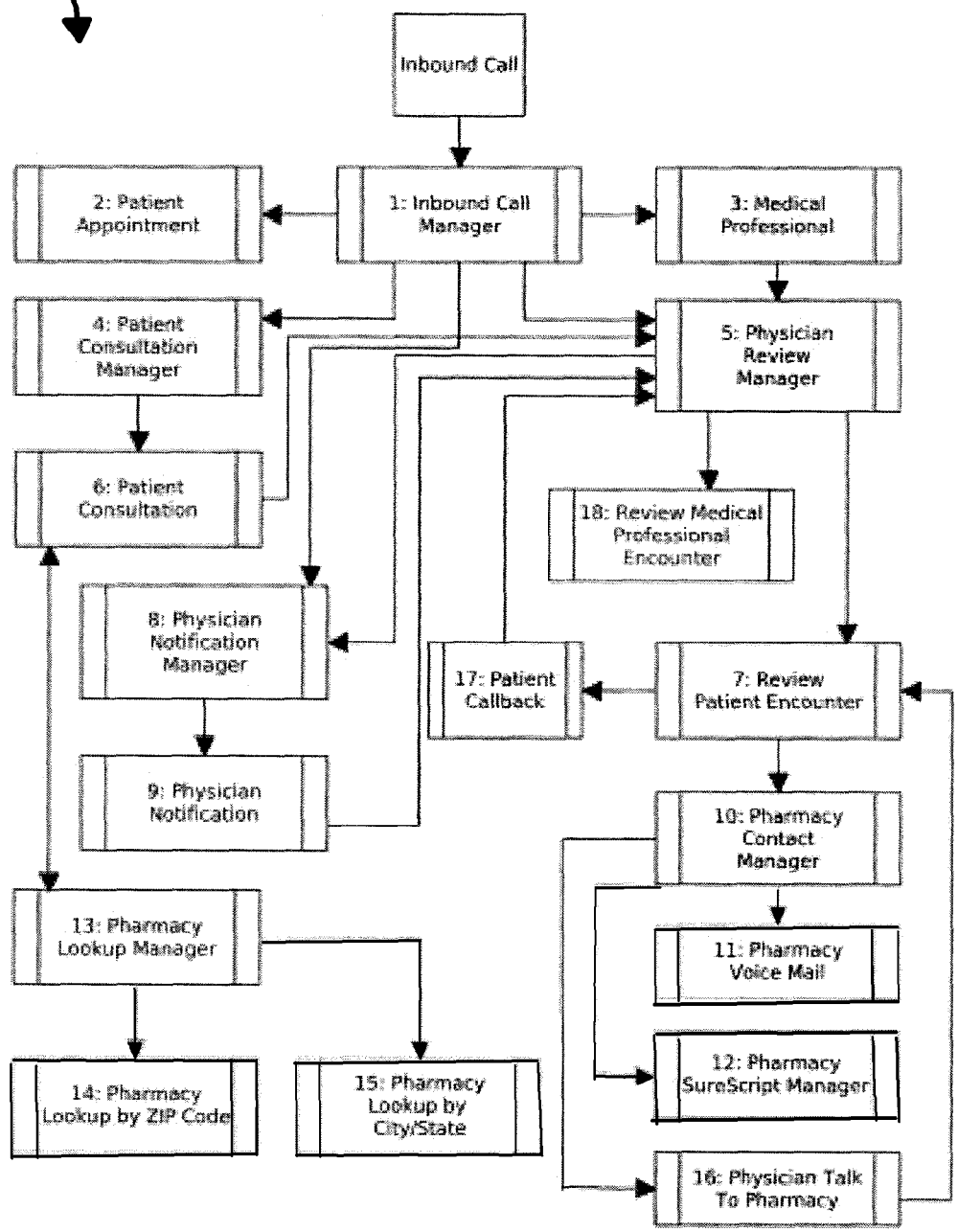
FIG. 10 is a flow chart of the overall system architecture for one embodiment.

A high-level design of the call management method and apparatus is provided herein. FIG. 10 provides a flow diagram of one embodiment of the method and apparatus for call management. In one embodiment the call management portion of the method and apparatus can include 18 modules, each module managing a particular phase of processing a call. Simple rectangles and diamonds in the flow diagrams define functions that themselves have details that are not shown for simplicity. Each of the modules are discussed in numerical order.

Module 1M: Inbound Call Manager

Figure 11:
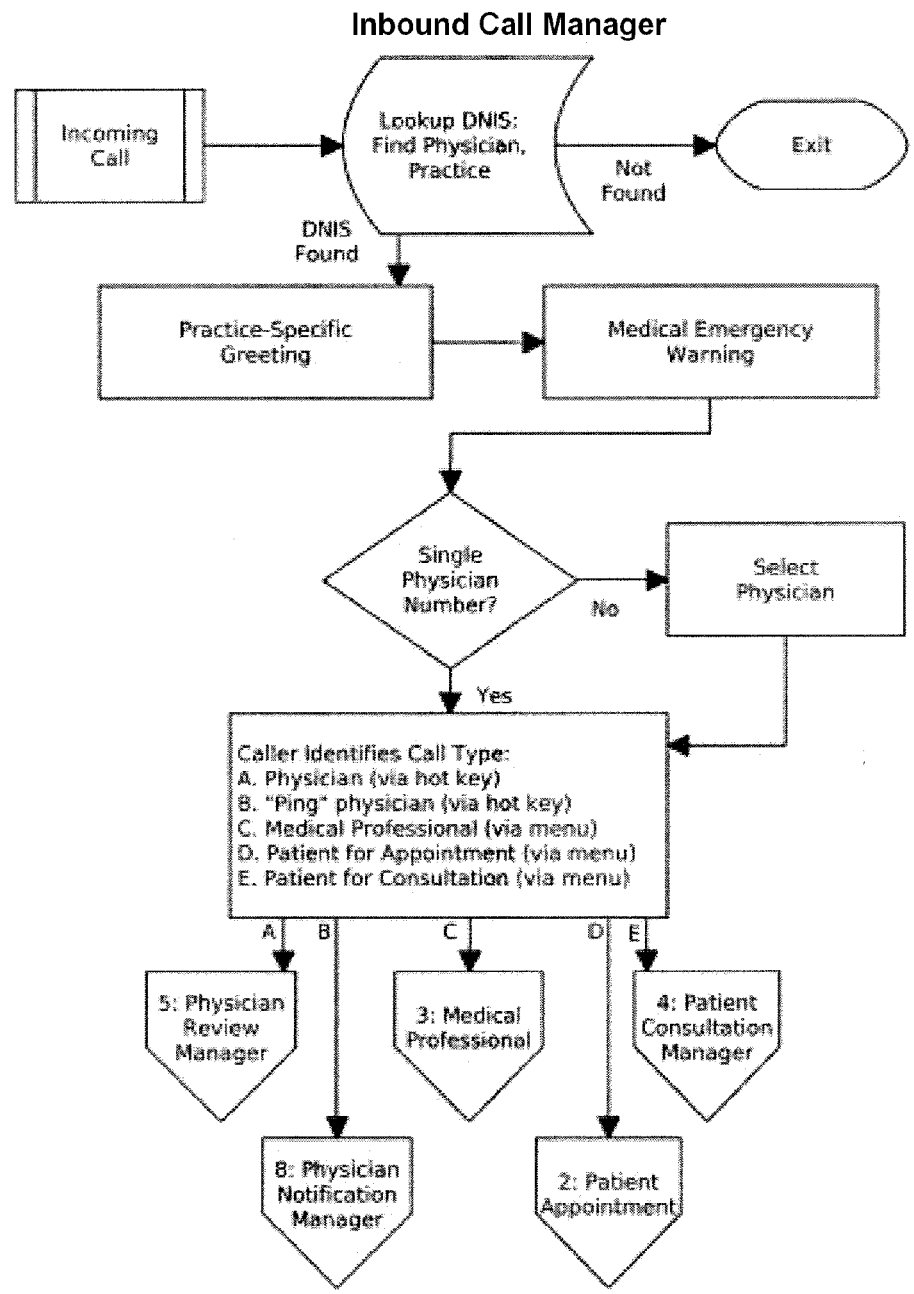
FIG. 11 is a flow chart for the Inbound Call Manager.

FIG. 11 schematically shows the Inbound Call Manager 1M which routes inbound calls. The inbound call manager has three principal tasks: (1) Determine the practice and health care provider to whom the inbound calls is being directed; (2) Determine the type of call; and (3) Direct the call down the appropriate path.

The practice can be determined by looking up the DNIS (the number dialed by the caller) in the database, and finding which practice "owns" the number at present. Module 1M can play a practice-specific greeting. It then plays a warning that persons calling for medical emergency should dial 911 or go to the nearest emergency room. If the number is associated with multiple health care providers, the caller can be asked to select the health care provider with whom he wishes to consult.

The module then asks the caller to select the type of call that he is making. A call can be one of five types: (1) A call from a health care provider who wants to review the calls he has received; (2) An administrator who wants to "ping" the health care provider to whom the phone is directed; (3) A call from a medical professional who wishes to speak with the health care provider; (4) A call from a patient who wishes to make an appointment; and (5) A call from a patient who wishes to consult with the health care provider.

The type of call can be indicated either by pressing a "hot key," or by selecting an item from a menu. Once the caller indicates what action he wants to take with the method and apparatus, the method and apparatus forwards the call to the module that is appropriate for that type of call.

Module 2M: Patient Appointments

Figure 12:
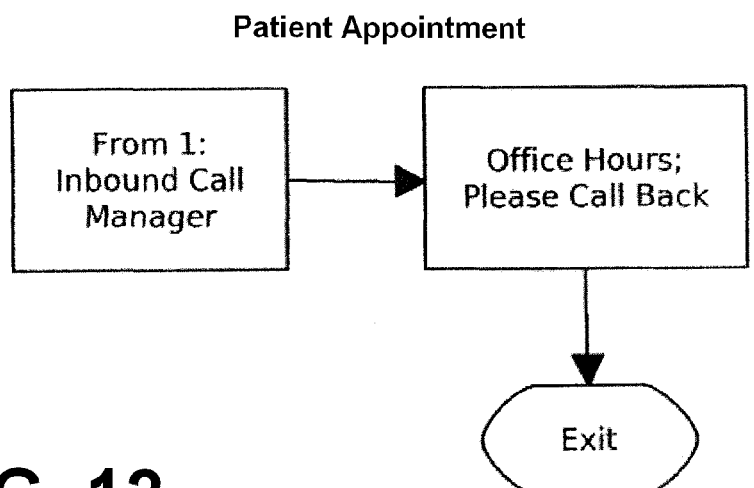
FIG. 12 is a flow chart for the Patient Appointment Manager.

The inbound call manager directs calls to this module 2M if the caller indicates that he is a patient who is interested in an appointment. FIG. 12 schematically shows the Patient Appointment Module 2M.

In one embodiment the module assumes that the method and apparatus 10 is always run in after-hours mode. Thus, with this assumption module 2M plays an informational message that gives the practice's office hours, and asks the patient to call back. In other embodiments module 2M can be run during hours and can direct calls to an appointment scheduler (which can be an automated scheduler, a live person, or an answering service).

Module 3M: Medical Professional

Figure 13:
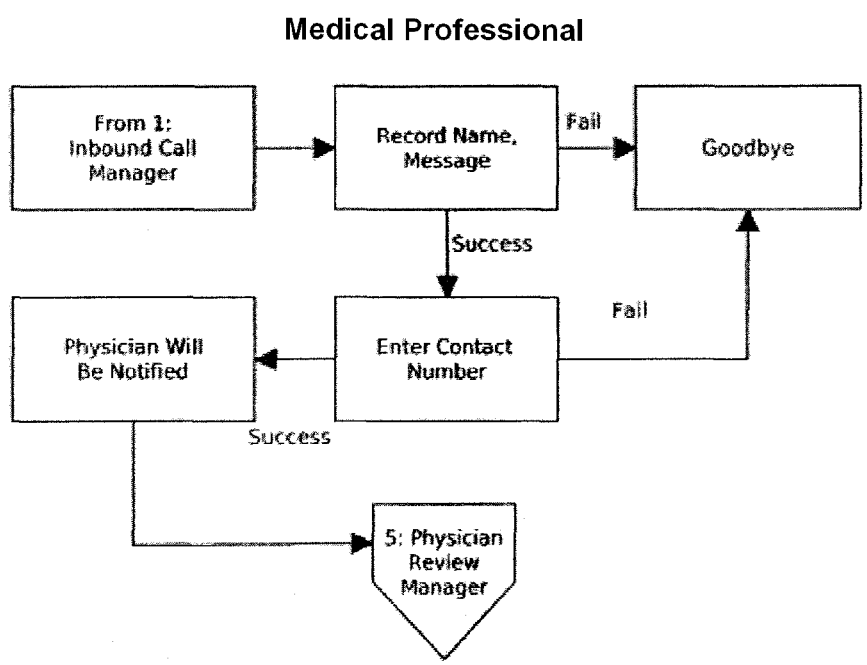
FIG. 13 is a flow chart for the Medical Professional Manager.

Calls are directed to this module if the caller indicates that he is a medical professional who wants to speak with the health care provider. FIG. 13 schematically shows the Medical Professional Module 3M. The method and apparatus 10 has the medical professional record his name and enter the contact telephone number. Once the recordings are made, the method and apparatus 10 adds that message to the appropriate queue of messages for the health care provider to review.

Module 4M: Patient Consultation Manager

Figure 14:
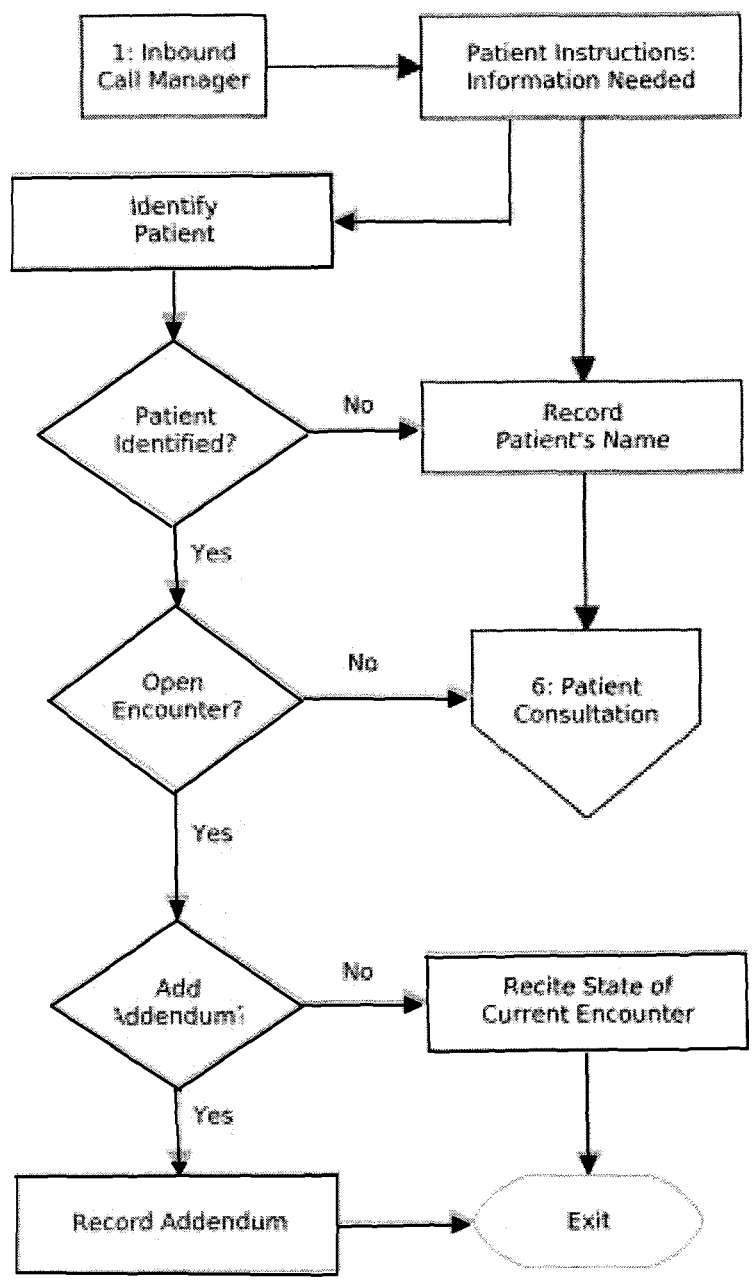
FIG. 14 is a flow chart for the Patient Consultation Manager.

The patient consultation manager 4M manages the patient's automated consultation with the health care provider. FIG. 14 schematically shows the Patient Consultations Manager Module 4M. The patient consultation manager 4M first tells the caller what the information he must have in order to arrange a consultation with the health care provider.

The module 4M then attempts to identify the patient. Identification can be done by having the patient enter one or more items of demographic information, such as first name and date of birth. Identifying the patient depends on the method and apparatuses 10 database maintaining a profile of the patients who use the method and apparatus, and then comparing demographic information entered by the patient with information in the database. For example, the combination of ANI, date of birth (as entered on the telephone keypad), plus first name (as returned by voice recognition) may well identify the patient with a high degree of confidence.

In one embodiment Module 4M can then checks whether the patient has an "open encounter"—an encounter with the health care provider that is the result of a call the patient made earlier, and that is not yet fulfilled. If the patient already has an open encounter, this means that the health care provider has not yet reviewed the encounter; therefore, module 4M asks the patient whether he wishes to record an addendum to what he has already said. If the patient does wish to record an addendum, the method and apparatus 10 records it and adds it to the recording of the patient's chief complaint. If the patient does not wish to record an addendum, the module informs the patient of the state of the encounter. In either case, module 4M then terminates the call.

Once the patient is identified, module 4M asks the patient to record his name. It then turns control of the call over to module 6M, which performs the body of the patient consultation. In this embodiment recording of the patient's name can be done in module 4M rather than module 6M so that recording and analysis of the name will be part of the patient-identification function.

Module 5M: Health Care Provider Review Manager

Figure 15:
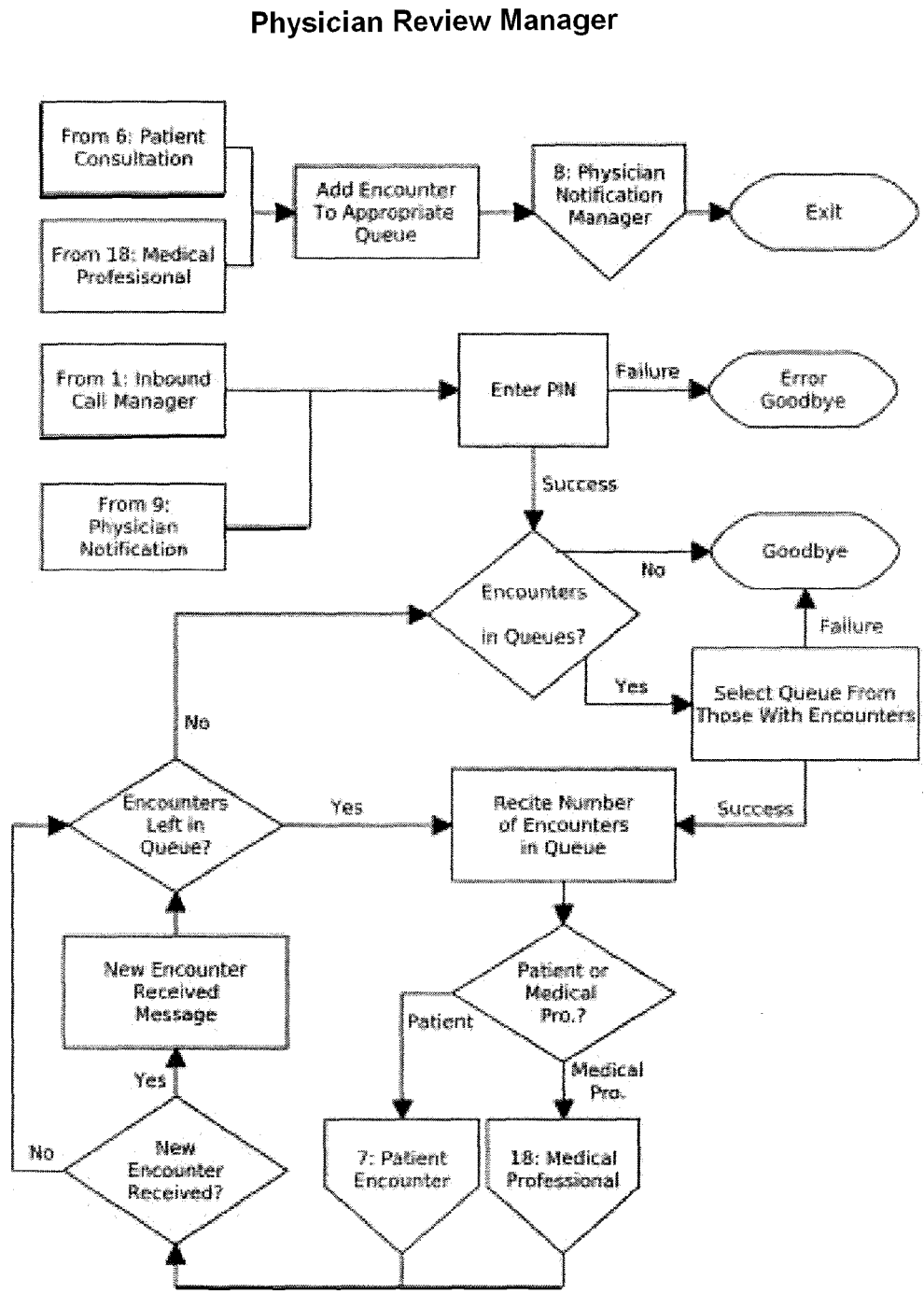
FIG. 15 is a flow chart for the Physician Review Manager.

The health care provider review manager 5M presents patient encounters to the health care provider. FIG. 15 schematically shows the Heath Care Provider Review Manager 5M. Module 5M can be accessed from four other modules and its behavior can differ depending on the module from which it is accessed.

When accessed from module 6M (patient consultation) or 18M (medical-professional consultation), module 5M generates an encounter record for that consultation, and adds it to the appropriate queue for that health care provider. There can be two queues: (1) one for encounters from medical professionals, and (2) a second for encounters from patients. Module 5M then accesses module 8M (health care provider notification manager), to start the process of notifying the health care provider that an encounter has been received.

When accessed from module 1M (inbound call manager) or 9M (health care provider notification), module 5M manages the a health care provider's review of encounters. The review of encounters is described below.

The first task is to "log in" the health care provider which can be by asking the health care provider to enter his PIN to confirm his identity. If the caller fails to enter the PIN of the health care provider who "owns" this telephone number, then the method and apparatus 10 terminates the call. Module 5M then checks whether the health care provider's queues have encounters spooled in them, and takes the following action: (1) If neither queue contains encounters, the module informs the health care provider of that fact, and terminates the call; (2) If one queue contains encounters, the module informs the health care provider of that fact, and start presenting the encounters to the health care provider; and (3) If both queues contain encounters, the module asks the health care provider to select the queue he wishes to review first.

Within a queue, encounters are presented in the order in which they were received. For each encounter from a medical professional, module 5M invokes module 18M, which manages the review of an individual medical-professional encounter. For each encounter from a patient, module 5M invokes module 7M.

After each encounter is processed, module 5M may tell the health care provider how many encounters remain in the queue. In one embodiment module 5M can go through sequentially each encounter without telling the health care provider how many encounters remain in the queue.

In one embodiment, while the health care provider was fulfilling an encounter, the method and apparatus 10 received another encounter of the type appropriate for that queue, module 5M can inform the health care provider of the new encounter.

In one embodiment, when all encounters have been reviewed, module 5M terminates the call.

In one embodiment module 5M can support voice recognition for navigating its commands and menu. This will allow "hands-free" navigation of the module; and, as health care providers gain experience in working with the method and apparatus, will greatly speed review of calls.

Module 6M: Patient Consultation

Figure 16:
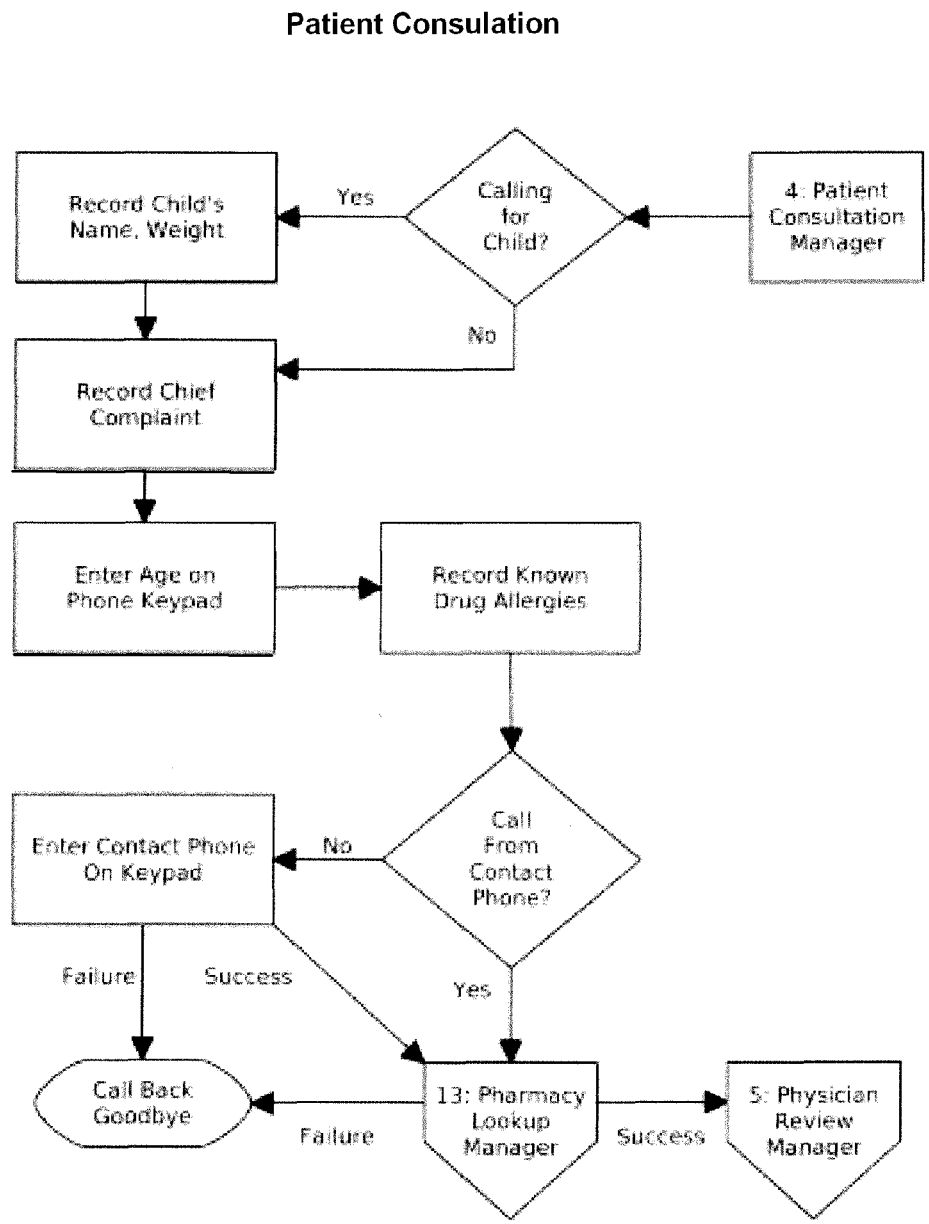
FIG. 16 is a flow chart for the Patient Consultation Manager.

Once a patient is identified and the method and apparatus 10 opens a new encounter, it invokes module 6M (the patient consultation module), to collect information from the patient. FIG. 16 schematically shows the Patient Consultation Module 6M which asks the patient whether he is calling for a child. If so, module 6M asks the caller to recite the child's name and weight (weight can be important in computing medication dosages for children). Module 6M can then ask for the following information: (1) chief complaint, recited; (2) patient's age, entered on keypad; and (3) known drug allergies, recited. The order in which these items of information are collected can change. Once the above listed items of information are collected, module 6M asks the patient if he can be called back on the phone from which the call was made. In an alternative embodiment caller identification can be used to provide a call back number for the calling in patient. If the answer is no, module 6M asks the patient to enter the telephone number at which he can be called back. Module 6M can then invoke module 13M (pharmacy lookup module) to walk the patient through selecting a pharmacy. If all the information is successfully collected, module 6M passes the call to module 5M (physician review manager), which queues this encounter for the physician's review. Additionally, module 6M can tell the patient to expect a telephone call, and terminates the call.

Module 7M: Review of Patient Encounter

Figure 17:
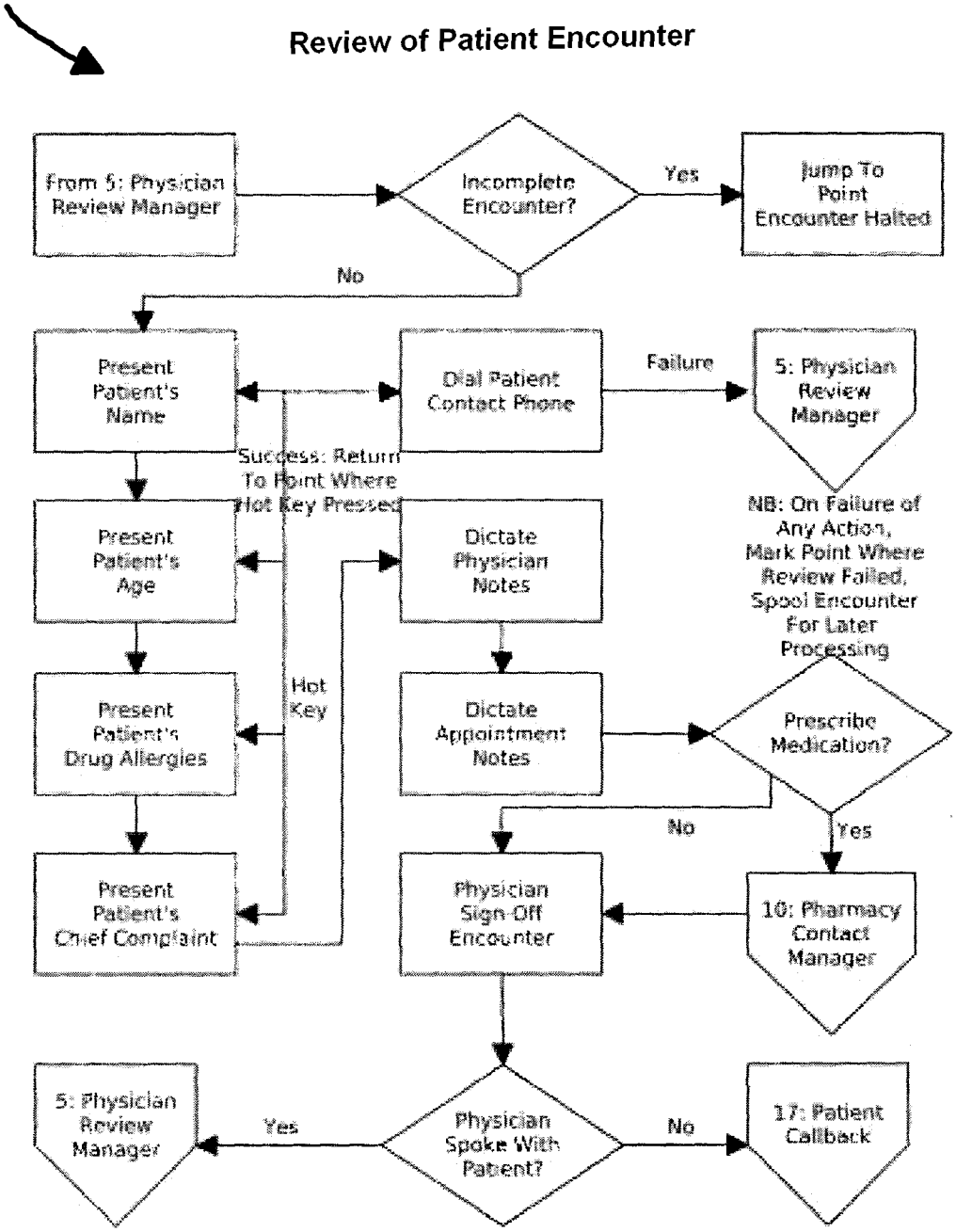
FIG. 17 is a flow chart for the Review of Patient Encounter Manager.

FIG. 17 schematically shows Module 7M Review of a Patient Encounter. Module 7M walks the health care provider through the review of a patient encounter. Module 7M first checks whether the event was "broken"—that is, whether it was only partially completed during an earlier call from the health care provider. An event can be broken for any of a number of reasons: for example, the health care provider's cell phone dropped the connection accidentally, or an attempt to dial a pharmacy to deliver a prescription failed because the line was busy. If the encounter was broken, the module informs the health care provider of that fact, and then resumes processing with the task at which the break occurred.

Module 7M then presents the patient's information: (i) Caller's name, (ii) If the patient is a child, the child's name and weight, (iii) Patient's age, (iv) Known drug allergies, and (v) Chief complaint. The method and apparatus 10 will have processed the recordings to remove dead air, and to compress the recordings in order to speed playback.

At any time during the recitation, the health care provider can press hot keys or speak a command to perform one of several tasks: (I) Skip the current item of information, (ii) Replay the current item of information, and (iii) Dial the patient at his contact number. If the call to the patient fails, for example because the patient's line is busy, the encounter is marked as broken and is returned to the health care provider's queue. If the call succeeds, then, upon conclusion of the call, the method and apparatus returns the health care provider to the point in the module at which he ordered the method and apparatus to dial the call.

In one embodiment every call dialed by the method and apparatus 10 is recorded automatically. When the call is connected, the method and apparatus 10 plays a message to both parties that informs them that the call is being recorded.

If the health care provider determines that the patient needs medication, the method and apparatus 10 transfers control of the call to module 10M (pharmacy contact manager)

Once the work is finished, the method and apparatus 10 asks the health care provider to confirm that the event is concluded. Once the health care provider does so, the method and apparatus 10 marks the encounter as closed.

Finally, the method and apparatus 10 checks whether the health care provider has spoken with the patient. If the health care provider has not, then the method and apparatus invokes module 17M (patient callback module) to spool an automated message to the patient. However, if the health care provider has spoken with the patient, the method and apparatus 10 returns immediately to module 5M (health care provider review manager).

In one embodiment module 6M will support voice recognition for navigating its commands and menu. This will allow "hands-free" navigation of the module; and, as health care providers gain experience in working with the method and apparatus, will greatly speed review of calls.

Module 8M: Health Care Provider Notification Manager

Figure 18:
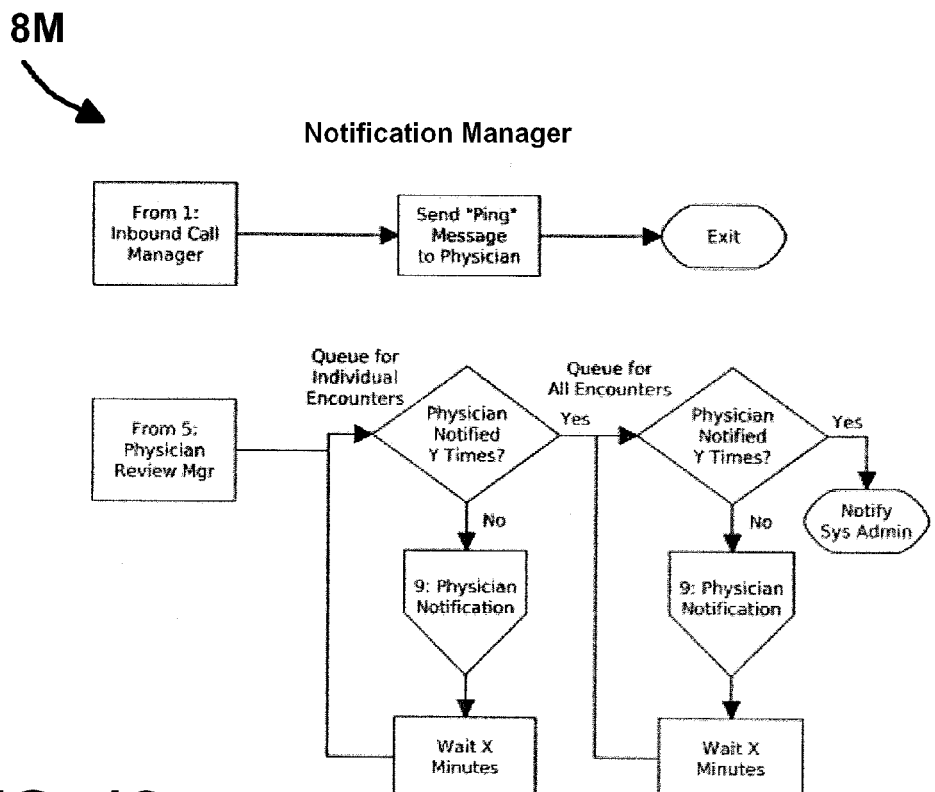
FIG. 18 is a flow chart for the Physician Notification Manager.

The health care provider notification manager, as its name suggests, is an automated module that manages the task of notifying the health care provider that he has one or more encounters queued for review. FIG. 18 schematically shows the Health Care Provider Notification Manager Module 8M.

There are two types of notification. In the first, which is received from module 1, the module "pings" the health care provider. That is, it sends the health care provider a message to confirm that calls are being accepted for him. The second type of notification is to inform the health care provider when his queue has one or more encounters waiting for fulfillment. The method and apparatus uses the following rules to manage notification: (1) There are two queues: one for notification of individual encounters, and a second, "reminder" queue for all encounters taken together and (2) When a call is first received, a notification message is sent to the health care provider immediately. Thereafter, for that encounter, Y messages are sent at intervals of X minutes; the values of Y and X are set by the health care provider. Each message is sent via the medium that the health care provider has chosen for that point in the notification process; (3) Afterward Y messages have been sent, then the notification for that encounter is forwarded to the "reminder" queue. This queue sends a message every X minutes for all encounters together, regardless of how many there are. If Y is set to zero, then all encounters are immediately grouped together in the "reminder" queue; and (4) After the health care provider has been "reminded" a preset number of times, the method and apparatus 10 assumes that something is wrong with the health care provider, and notifies the method and apparatus administrator to take remedial action. What is done will vary from one practice to the another, and may require consultation with a practice administrator.

Because the health care provider will have the ability to select how he is notified with each iteration of the notification cycle, the work of actually performing the notification is handed off to module 9M (health care provider notification module).

Module 9M: Health Care Provider Notification

Figure 19:
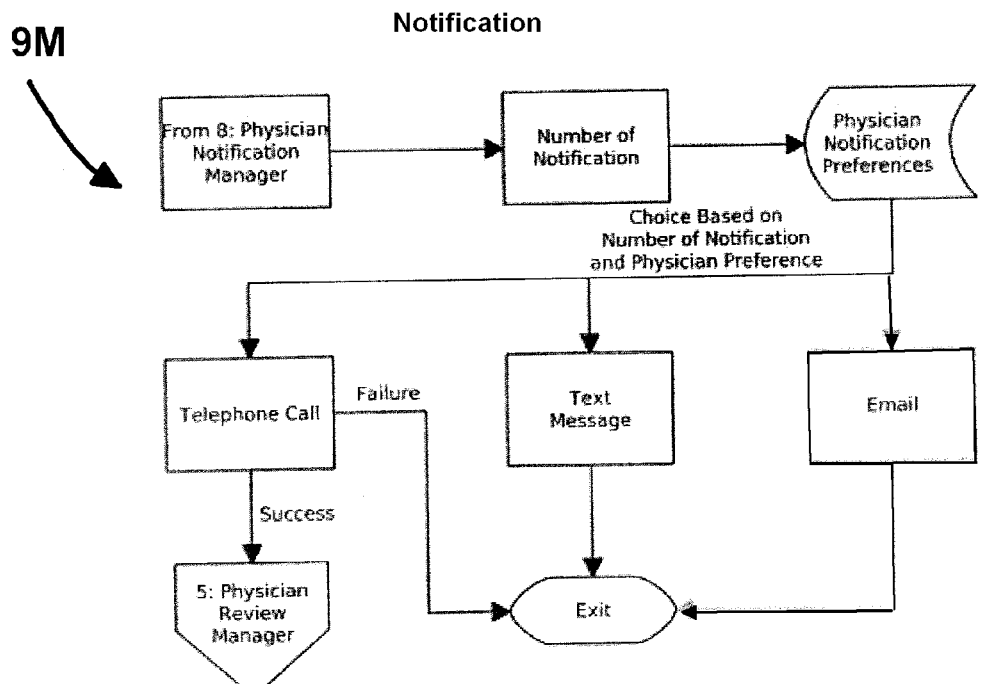
FIG. 19 is a flow chart for the Patient Notification Manager.

This module 9M actually performs the task of notifying the health care provider that he has encounter queued for fulfillment. FIG. 19 schematically shows the Health Care Provider Notification Module 8M.

The method and apparatus 10 first checks the number of times that the health care provider has been notified since he last called in. It then retrieves from the database the health care provider's preference for notification for that iteration, and uses that information to select the medium for notifying the health care provider.

In various embodiments, notification can be done via email, text message, or a telephone call. In a preferred embodiment text messaging will be unidirectional: the method and apparatus will send messages to the health care provider, but the health care provider will not be able to message the method and apparatus 10.

If the health care provider is contacted via telephone, he will have the option of reviewing calls immediately. If the health care provider chooses to do so, then the call will be forwarded to module 5M (health care provider review manager) to present the encounters to the health care provider.

Module 10M: Pharmacy Contact Manager

Figure 20:
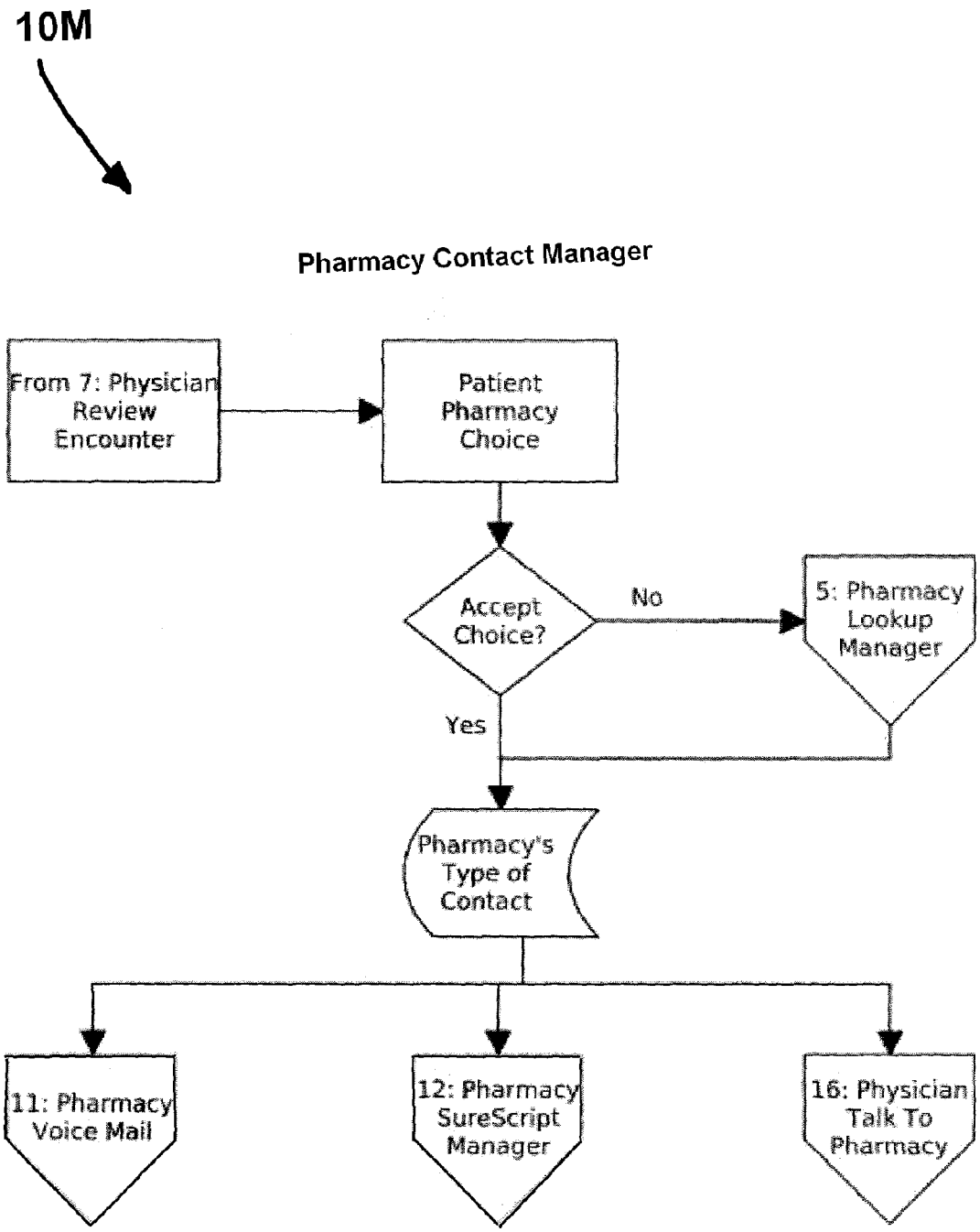
FIG. 20 is a flow chart for the Pharmacy Contact Manager.

The pharmacy contact manager module 10M manages health care providers' contacts with pharmacies. FIG. 20 schematically shows the structure of this module.

Module 10M looks up the pharmacy that the patient chose. If it is acceptable to the health care provider, then the contact can proceed; however, if it isn't (perhaps because the health care provider knows that the pharmacy is closed), the health care provider is routed to module 13M (the pharmacy lookup manager) to select another pharmacy.

Once the pharmacy is confirmed, the method and apparatus 10 looks up the method by which the pharmacy is to be contacted. If the pharmacy is to be contacted via voice mail or an electronic prescription service, the call is forwarded to the appropriate module, to recite the prescription; however, if the health care provider must speak directly to the pharmacy, the method and apparatus dials the pharmacy and connects the health care provider with the pharmacy once the call connects.

Module 11M: Pharmacy Voice Mail

Module 11M records the health care provider's recitation of the prescription, then automatically uploads it to the pharmacy's voice mail method and apparatus. Each voice-mail method and apparatus uses its own set of prompts and inputs, so each will require its own script in order to upload a recording of a prescription. In a preferred embodiment the voice-mail interface can service major chains, most of which use one voice-mail for all of their pharmacies.

Module 12M: Pharmacy Electronic Prescription Service System Manager

Module 12M records the health care provider's recitation of the prescription, analyzes the recitation with voice recognition, then uses the electronic prescription service system to transmit the prescription to the pharmacy in an automated fashion.

Module 13M: Pharmacy Lookup Manager

Figure 21:
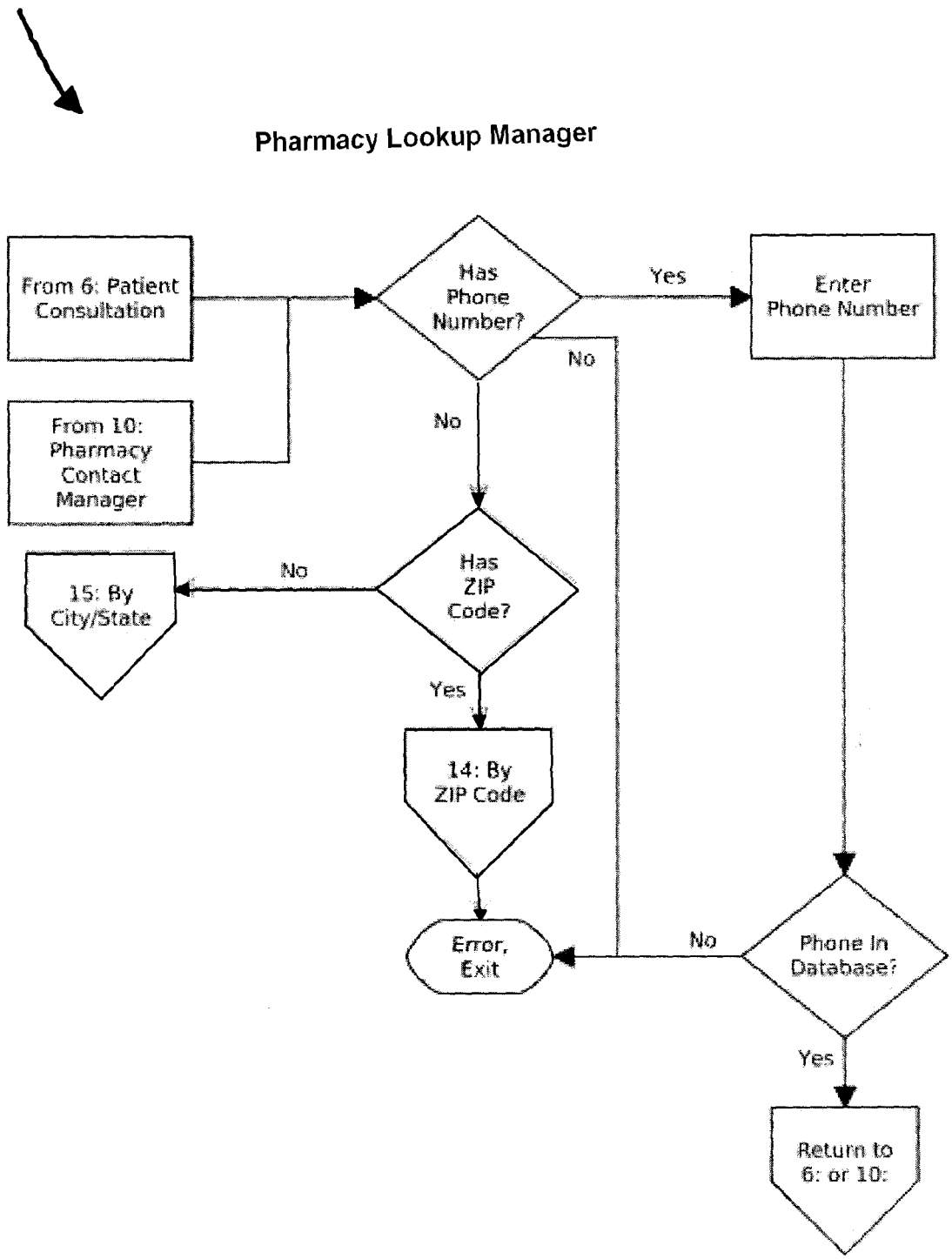
FIG. 21 is a flow chart for the Pharmacy Lookup Manager.

Module 13M manages the lookup of a pharmacy by a patient or health care provider. FIG. 21 schematically shows the structure of this module. The module first prompts the caller to enter the pharmacy's telephone number. If the telephone number that is entered matches one in the database, then it's done, and it returns to the module from which it was called.

However, if the caller does not know the pharmacy's telephone number, then the method and apparatus asks whether he knows the region's ZIP code. If the caller does know the ZIP code, then the method and apparatus 10 forwards the call to module 14M, the pharmacy lookup by ZIP code. If the caller does not know the ZIP code, then the method and apparatus forwards the call to module 15M, pharmacy lookup by city/state.

Module 14M: Pharmacy Lookup by ZIP Code

Module 14M asks the caller to enter a ZIP code his locale, then walks the caller through the process of selecting a pharmacy from among those in or near that ZIP code. Pharmacy lookup will be done by a database query that matches the center point of the ZIP code, as expressed in AT&T vertical/horizontal coordinates, with the location of each pharmacy, again as expressed in vertical/horizontal coordinates.

Module 15M: Pharmacy Lookup by City/State

Module 15M has the caller recite his city and state, then walks the caller through the process of selecting a pharmacy from among those in or near that city. Pharmacy lookup will be done by comparing the center point of the city, as expressed in AT&T vertical/horizontal coordinates, with the location of each pharmacy, again as expressed in vertical/horizontal coordinates.

Module 16M: Health Care Provider Talk to Pharmacy

Figure 23:
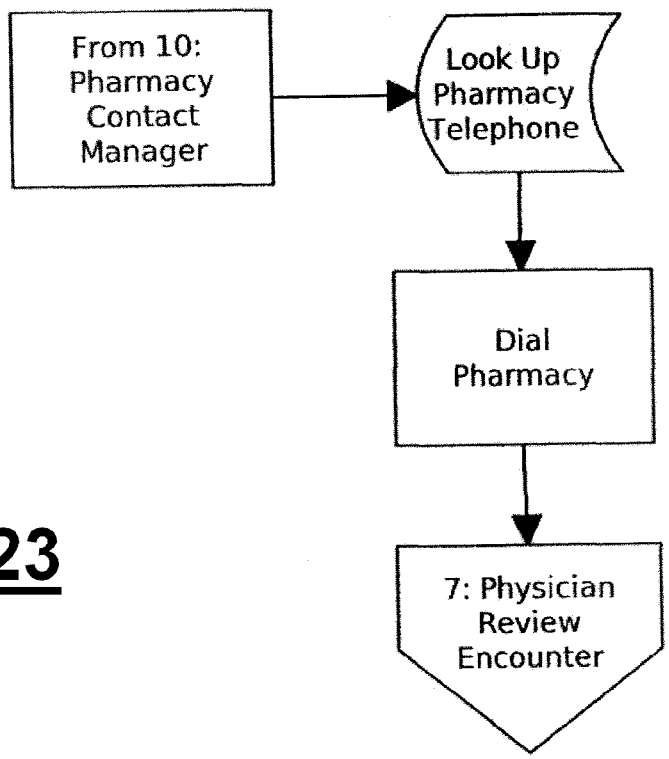
FIG. 23 is a flow chart for the Pharmacy Contact Manager.

Module 16M telephones the pharmacy so the health care provider can recite the prescription to the pharmacy. FIG. 23 schematically shows the structure of this module. The module looks up the telephone number that the patient or health care provider selected via modules 13 through 15, then dials a call to that pharmacy. In one embodiment every call dialed by the method and apparatus 10 is recorded automatically. When the call is connected, the method and apparatus 10 recites a message to both parties to inform them that the call is being recorded. Regardless of the outcome of dialing, success or failure, control of the call after dialing is returned to module 7M, so the health care provider can conclude his fulfillment of the encounter.

Module 17M: Patient Callback

Figure 22:
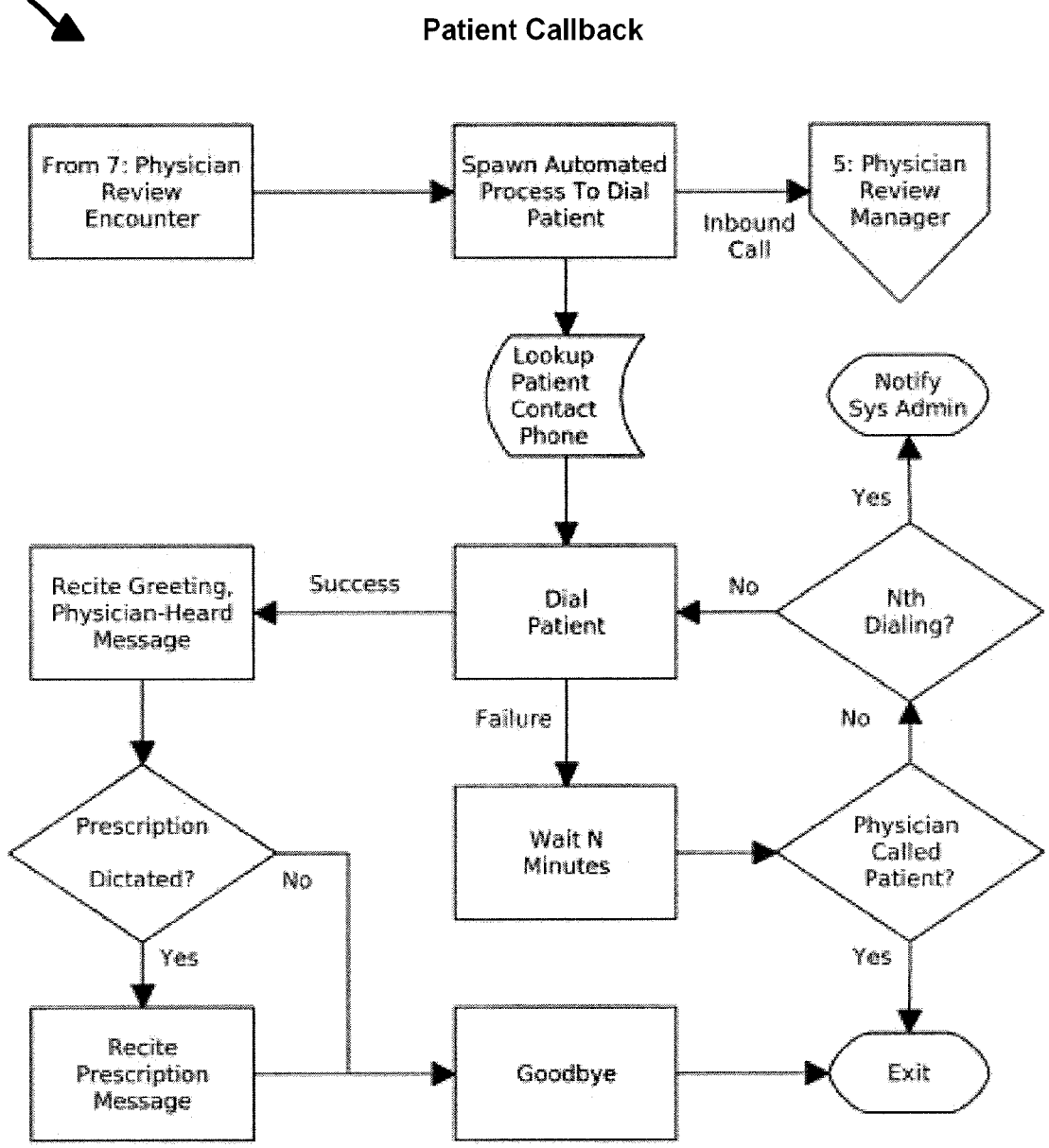
FIG. 22 is a flow chart for the Patient Callback Manager.

The patient callback module 17M invokes an automated process to contact the patient and inform him that the health care provider has reviewed his complaint. FIG. 22 schematically shows the structure of this module. Module 17M is invoked if the health care provider has not already spoken with the patient while reviewing the patient's complaint.

The method and apparatus 10 dials the patient's contact telephone number. Upon answering, it delivers an automated message stating that the health care provider has reviewed the case. If a prescription has been written for the patient, the method and apparatus 10 informs the patient of that fact. If the prescription is being sent to a pharmacy other than the one the patient selected, then the method and apparatus 10 tells the patient where the prescription has been sent.

If the method and apparatus cannot contact the patient within predetermined number of dialings (e.g., N dialings), then the method and apparatus administrator is notified.

If the method and apparatus 10 finds that the health care provider has spoken with the patient since the attempt to dial the patient, the method and apparatus halts attempts to dial the patient, because there is no more need to do so.

When it has completed all tasks associated with a patient transaction, the method and apparatus 10 marks the transaction as concluded. If, for any reason, it could not execute a task associated with a patient transaction, the method and apparatus 10 marks that transaction as incomplete. It logs the fact the transaction was incomplete, along with a description of the task or tasks that it failed to complete and a description of the nature of the failure. A summary of the transactions successfully complete and those that failed to be completed is then made available to method and apparatus administrators.

Module 18M: Medical Professional Consultation

Figure 24:
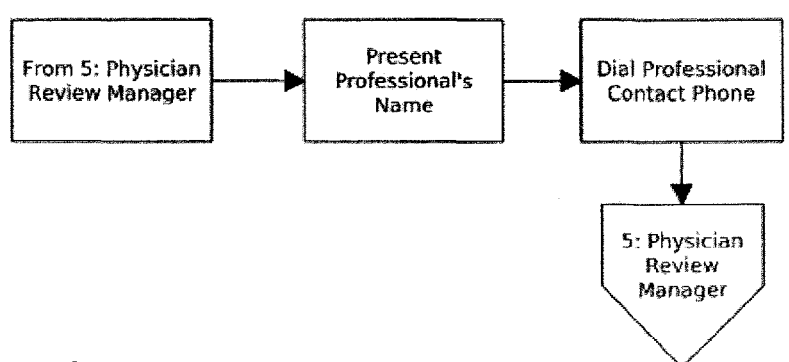
FIG. 24 is a flow chart for the Review of Encounter Manager.

Module 18M manages a health care provider's consultation with a medical professional. FIG. 24 schematically shows the structure of this module. Module 18M recites the medical-professional's name to the health care provider. It then attempts to dial the professional at the contact telephone number he entered in module 3M. The health care provider has the option of aborting dialing and marking this encounter as closed; the health care provider could do so if, say, he had already spoken with the professional and there was no need to talk with him/her again.

In one embodiment every call dialed by the method and apparatus 10 is recorded automatically. When the call is connected, but before it is bridged, the method and apparatus 10 plays a message to both parties to inform them that the call is being recorded. When the call has been completed, the method and apparatus 10 marks this encounter as closed, then returns the caller to module 5M, to continue review of the queue that manages encounters with medical professionals.

In one embodiment module 18M will support voice recognition for navigating its commands and menu. This will allow "hands-free" navigation of the module; and, as health care providers gain experience in working with the method and apparatus, will greatly speed review of calls.

The following is a list of reference numerals used in this application:

LIST FOR REFERENCE NUMERALS

| (Reference No.) | (Description) |
| --- | --- |
| 10 | method and apparatus |
| 200 | patient compiler process |
| 300 | health care provider process |
| 700 | event concluder |
| 750 | patient callback |
| 775 | provider callback |
| 800 | prescription transmission process |
| 900 | follow-up appointment process |
| 2000 | patient compiler flow chart |
| 2010 | step |
| 2020 | step |
| 2030 | step |
| 2040 | step |
| 2050 | step |
| 2060 | step |
| 2070 | step |
| 2080 | step |
| 2090 | step |
| 2100 | step |
| 2110 | step |
| 2120 | step |
| 2130 | step |
| 2140 | step |
| 2150 | step |
| 2160 | step |
| 2170 | step |
| 2180 | step |
| 2185 | step |
| 2190 | step |
| 2200 | step |
| 2210 | step |
| 2220 | step |
| 2230 | step |
| 2240 | step |
| 2250 | step |
| 2260 | step |
| 2270 | step |
| 2280 | step |
| 2300 | step |
| 2310 | step |
| 2320 | step |
| 2330 | step |
| 2340 | step |
| 2350 | step |
| 2360 | step |
| 2370 | step |
| 2380 | step |
| 2390 | step |
| 2400 | step |
| 2410 | step |
| 2420 | step |
| 2430 | step |
| 3000 | provider compiler flow chart |
| 3010 | step |
| 3020 | step |
| 3030 | step |
| 3040 | step |
| 3050 | step |
| 3060 | step |
| 3070 | step |
| 3080 | step |

-continued

LIST FOR REFERENCE NUMERALS

| (Reference No.) | (Description) |
|---|---|
| 3090 | step |
| 3100 | step |
| 3110 | step |
| 3120 | step |
| 3130 | step |
| 3140 | step |
| 3150 | step |
| 3160 | step |
| 3170 | step |
| 3180 | step |
| 3200 | step |
| 3210 | step |
| 3220 | step |
| 3230 | step |
| 3240 | step |
| 3250 | step |
| 3260 | step |
| 3270 | step |
| 3280 | step |
| 3290 | step |
| 3300 | step |
| 3310 | step |
| 3320 | step |
| 3330 | step |
| 3340 | step |
| 3350 | step |
| 3360 | step |
| 3370 | step |
| 3380 | step |
| 3390 | step |
| 3500 | step |
| 3510 | step |
| 3520 | step |
| 3530 | step |
| 3540 | step |
| 3550 | step |
| 3560 | step |
| 3570 | step |
| 3580 | step |
| 3590 | step |
| 3600 | step |
| 3610 | step |
| 3620 | step |
| 3630 | step |
| 3640 | step |
| 3650 | step |
| 3660 | step |
| 3670 | step |
| 3680 | step |
| 3690 | step |
| 3700 | step |
| 3710 | step |
| 3720 | step |
| 3730 | step |
| 3740 | step |
| 3750 | step |
| 3800 | step |
| 3810 | step |
| 3820 | step |
| 3830 | step |
| 7000 | event concluder flow chart |
| 7010 | step |
| 7020 | step |
| 7030 | step |
| 7040 | step |
| 7050 | step |
| 7060 | step |
| 7070 | step |
| 7080 | step |
| 7090 | step |
| 7100 | step |
| 7110 | step |
| 7120 | step |
| 7130 | step |
| 7140 | step |

-continued

LIST FOR REFERENCE NUMERALS

| (Reference No.) | (Description) |
|---|---|
| 7150 | step |
| 7160 | step |
| 7170 | step |
| 7180 | step |
| 7190 | step |
| 7200 | step |
| 7210 | step |
| 7220 | step |
| 7230 | step |
| 7240 | step |
| 7250 | step |
| 7260 | step |
| 7270 | step |
| 7280 | step |
| 7290 | step |
| 7300 | step |
| 7500 | step |
| 7510 | step |
| 7520 | step |
| 7530 | step |
| 7540 | step |
| 7560 | step |
| 7570 | step |
| 7580 | step |
| 7590 | step |
| 7600 | step |
| 7610 | step |
| 7620 | step |
| 7630 | step |
| 7640 | step |
| 7650 | step |
| 7660 | step |
| 7670 | step |
| 7680 | step |
| 7690 | step |
| 7700 | step |
| 7710 | step |
| 7720 | step |
| 7730 | step |
| 7740 | step |
| 7750 | step |
| 7760 | step |
| 7770 | step |
| 7780 | step |
| 7790 | step |
| 7800 | step |
| 7810 | step |
| 7815 | step |
| 8000 | prescription flow chart |
| 8010 | step |
| 8020 | step |
| 8030 | step |
| 8040 | step |
| 8060 | step |
| 8070 | step |
| 8080 | step |
| 8085 | step |
| 9000 | appointment notification flow chart |
| 9010 | step |
| 9020 | step |
| 9030 | step |
| 9040 | step |
| 9060 | step |
| 9070 | step |
| 9080 | step |
| 9090 | step |
| 9100 | step |
| 9110 | step |
| 9120 | step |
| 9130 | step |
| 9135 | step |
| 9140 | step |
| 10000 | provider activation flow chart |
| 10010 | step |
| 10020 | step |

-continued

LIST FOR REFERENCE NUMERALS

| (Reference No.) | (Description) |
|---|---|
| 10030 | step |
| 10040 | step |
| 10050 | step |
| 10060 | step |
| 10070 | step |
| 10080 | step |
| 10090 | step |
| 10100 | step |
| 10110 | step |
| 10120 | step |
| 10130 | step |
| 10140 | step |
| 10150 | step |
| 10160 | step |
| 10170 | step |

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

What is claimed is:

1. A method of providing indirect medical consultation comprising the steps of:
   (a) receiving a telephone call from a person seeking indirect medical consultation from a human health care provider;
   (b) during the telephone call of step "a", recording a set of information from the person, the set of information including
   a telephone number,
   a name of a patient,
   an oral description of the problems with the patient, and
   a selected pharmacy;
   (c) before contact between the person seeking indirect medical consultation and the health care provider, transmitting this information to the human health care provider who reviews the information, and
   providing an option for the health care provider to be in telephone contact
   with the person seeking indirect medical consultation;
   (d) after step "c",
   based on a command from the health care provider,
   telephoning the person seeking indirect medical consultation
   and
   placing the health care provider in telephone contact with the person;
   (e) after step "d",
   recording the telephonic conversation
   between the health care provider and the person seeking indirect medical consultation during the telephone call in step "d";
   (f) compiling a medical record with the information of steps "b" and "e" and
   transmitting the compiled medical record to the health care provider
   which compiled medical record includes the recorded telephonic conversation of step "e"; and
   (g) providing a computer, the computer performing steps "a" through "f".

2. The method of claim 1, wherein an option is provided for the oral portions of the compiled medical record to be transcribed.

3. The method of claim 1, wherein after step "c", but before step "d" the health care provider is electronically prompted to prepare a diagnosis.

4. The method of claim 3, wherein the diagnosis by the health care provider is electronically recorded as oral statements from the health care provider and which recorded oral statements are included in the compiled medical record of step "e".

5. The method of claim 1, wherein after step "c", but before step "d" the health care provider is electronically prompted to prepare a treatment plan including required therapy.

6. The method of claim 5, wherein the treatment plan by the health care provider is electronically recorded as oral statements from the health care provider and which recorded oral statements are included in the compiled medical record of step "e", and the method further includes recording a prescription from the health care provider and the prescription is transmitted to the pharmacy in step "b".

7. The method of claim 1, wherein after step "c" and before step "d", the health care provider is electronically prompted to issue a prescription.

8. The method of claim 7, wherein the prescription by the health care provider is electronically recorded as oral statements from the health care provider and which recorded oral statements are included in the compiled medical record of step "e".

9. The method of claim 1, wherein an insurance billing record is at least partially automatically prepared outside of the health care provider.

10. The method of claim 1, further comprising the step of the health care provider being prompted to directly contact the person in step "b."

11. A method of providing indirect medical consultation comprising the steps of:
   (a) receiving a request for an indirect medical consultation from a person seeking indirect medical consultation from a human health care provider;
   (b) during step "a", recording a set of information from the person, the set of information including
   a telephone number,
   a name of a patient,
   an oral description of the problems with the patient, and
   a preferred pharmacy;
   (c) before contact between the person seeking indirect medical consultation and the health care provider, transmitting this information to the human health care provider
   who reviews the information;
   (d) after step "c", based on a command from the health care provider,
   contacting the person seeking indirect medical consultation, and then recording a telephonic conversation between the health care provider and the person seeking indirect medical consultation wherein the health care provider obtains additional information from the information transmitted in step "c", and recording a prescription from the health care provider;
   (e) transmitting the prescription to the pharmacy in step "b";

(f) compiling a medical record with the information of steps "b" and "d" to the health care provider, which compiled medical record includes the recorded telephonic conversation of step "d";
(g) providing access to the compiled medical record to the health care provider; and
(h) providing a computer, the computer performing steps "a" through "g".

12. The method of claim 11, wherein in step "f", the health care provider is provided the option of downloading the compiled medical record.

13. The method of claim 11, wherein in step "f", the compiled medical record is sent to the health care provider through electronic mail.

14. The method of claim 11, wherein an option is provided for the oral portions of the compiled medical record to be transcribed.

15. The method of claim 11, wherein after step "c", the health care provider is electronically prompted to prepare a diagnosis.

16. The method of claim 15, wherein the diagnosis by the health care provider is electronically recorded as oral statements from the health care provider and which recorded oral statements are included in the compiled medical record of step "f".

17. The method of claim 11, wherein after step "c", the health care provider is electronically prompted to prepare a treatment plan including required therapy.

18. The method of claim 17, wherein the treatment plan by the health care provider is electronically recorded as oral statements from the health care provider and which recorded oral statements are included in the compiled medical record of step "f".

19. The method of claim 11, wherein after step "c" and before step "d", the health care provider is electronically prompted to issue a prescription, and which prescription is electronically recorded as oral statements from the health care provider and which recorded oral statements are included in the compiled medical record of step "f".

20. The method of claim 11, wherein an insurance billing record is at least partially automatically prepared outside of the health care provider.

21. The method of claim 11, wherein between steps "c" and "d", the health care provider is provided with the option of soliciting additional information from the person seeking indirect medical consultation.

22. The method of claim 21, wherein if the option of soliciting additional information is selected, then the health care provider is provided with the option of recording an oral request to the patient for additional information.

23. The method of claim 22, wherein the recorded request of additional information is transmitted to the person seeking indirect medical consultation.

24. The method of claim 23, wherein the person seeking indirect medical consultation is provided with the option of recording a response to the request for additional information.

25. The method of claim 23, wherein the request for additional information and the response are compiled into the compiled medical record of step "f."

26. The method of claim 11, further comprising the step of the health care provider being prompted to directly contact the person in step "b."

27. A method of providing indirect medical consultation comprising the steps of:
(a) receiving a telephone call from a person seeking indirect medical consultation from a human health care provider;
(b) during step "a", creating an encounter by recording a set of information for the person, the set of information including
a return telephone number,
a name of a patient, and
an oral description of the complaint;
(c) notifying the health care provider that the an encounter has been received;
(d) before contact between the person seeking indirect medical consultation and the health care provider, in response to being contacted by the health care provider transmitting the information of step "b" to the health care provider
who reviews the information;
(e) based on a command from the health care provider telephoning the person seeking indirect medical consultation and
placing the health care provider in contact with the person;
(f) recording the telephonic conversation
between the health care provider and the person seeking indirect medical consultation in step "e";
(g) compiling a medical record with the information of steps "b" and "e"and
transmitting the compiled medical record to the health care provider,
which compiled medical record includes
the recorded telephonic conversation of step "f"; and
(h) providing a computer, the computer performing steps "a" through "g".

28. The method of claim 27, wherein between steps "d" and "e", and before the health care provider has been in first contact with the person seeking indirect medical consultation, recording a series of oral questions from the health care provider, telephoning the person seeking indirect medical consultation and playing the series of recorded oral questions, recording the responses by the person seeking indirect medical consultation to the series of oral questions, and transmitting the recorded oral responses to the health care provider.

29. The method of claim 27, wherein before step (e), the health care provider is electronically prompted to prepare a diagnosis.

30. The method of claim 29, wherein the diagnosis by the health care provider is electronically recorded as oral statements from the health care provider and which recorded oral statements are included in the compiled medical record of step "h".

31. The method of claim 27, wherein before step "e", the health care provider is electronically prompted to prepare a treatment plan including required therapy.

32. The method of claim 31, wherein the treatment plan by the health care provider is electronically recorded as oral statements from the health care provider and which recorded oral statements are included in the compiled medical record of step "h".

33. The method of claim 27, wherein after step "f" and before step "h", the health care provider is electronically prompted to issue a prescription, and which prescription is electronically recorded as oral statements from the health care provider and which recorded oral statements are included in the compiled medical record of step "h".

34. The method of claim 27, wherein before step "e" and when not in contact with the person seeking indirect medical consultation, the health care provider is provided with the option of first soliciting additional information from the person seeking indirect medical consultation.

35. The method of claim 34, wherein if the option of soliciting additional information is selected based on a command from the health care provider, then the health care provider is provided with the option of recording a series of oral questions seeking additional information at a time before the health care provider is first placed in contact with the person seeking indirect medical consultation.

36. The method of claim 35, wherein, at a time when the health care provider is not in contact with the person seeking indirect medical consultation, the recorded series of oral questions is first transmitted to the person seeking indirect medical consultation.

37. The method of claim 36, wherein, when not in contact with the health care provider, the person seeking indirect medical consultation is first provided with the option of recording an oral response to the request for additional information.

* * * * *